(12) United States Patent
Michot et al.

(10) Patent No.: US 6,319,428 B1
(45) Date of Patent: Nov. 20, 2001

(54) PERFLUORINATED AMIDE SALTS AND THEIR USES AS IONIC CONDUCTING MATERIALS

(75) Inventors: Christophe Michot, Grenoble (FR); Michel Armand, Montreal (CA); Michel Gauthier, La Prairie (CA); Yves Choquette, Sainte-Julie (CA)

(73) Assignees: Hydro-Quebec, Montreal (CA); Centre National de la Recherche Scientifique, Paris (FR)

( * ) Notice: Subject to any disclaimer, the term of this patent is extended or adjusted under 35 U.S.C. 154(b) by 50 days.

(21) Appl. No.: 09/125,797

(22) PCT Filed: Dec. 30, 1997

(86) PCT No.: PCT/CA97/01013

§ 371 Date: Dec. 3, 1998

§ 102(e) Date: Dec. 3, 1998

(87) PCT Pub. No.: WO98/29388

PCT Pub. Date: Jul. 9, 1998

(30) Foreign Application Priority Data

Dec. 30, 1996 (CA) .................................................. 2194127
Mar. 5, 1997 (CA) .................................................. 2199231

(51) Int. Cl.[7] .............................. H01B 1/12; H01M 6/16; H01G 4/04

(52) U.S. Cl. ..................... 252/500; 429/199; 429/200; 429/245; 29/623.1; 564/96; 564/98; 561/27; 361/327

(58) Field of Search ................................. 252/500, 622; 429/316, 245, 200, 199; 29/623.1; 564/96, 98; 568/27; 526/92; 361/327

(56) References Cited

U.S. PATENT DOCUMENTS 3,793,079   2/1974   Brown et al. .
4,851,307   7/1989   Armand et al. .
5,072,040   12/1991  Armand .

(List continued on next page.)

FOREIGN PATENT DOCUMENTS 0 571 832    5/1993   (EP) .
  731 518  * 11/1996   (EP) .
95/26056  *  9/1995   (WO) .

(List continued on next page.)

OTHER PUBLICATIONS

Banks et al "N–AALOGENO Compounds . . . " Journal of Fluorine Chemistry, 46 (1990) 297–305.*

Potrov et al "Synthesis of Poly Fluoro–2–alleanesulfonyl–3, 3–dialkyloxaziridinos" Journal of Fluorine Chemistry, 68 (1994) 277–286.*

Lis et al "Synthesis and Antiarrhythmic Activity . . . " J. Med. Chem. 1987, 30, 696–704.*

*Primary Examiner*—Mark Kopec
(74) *Attorney, Agent, or Firm*—Hutchins, Wheeler & Dittmar

(57) ABSTRACT

The invention concerns ionic compounds in which the anionic load has been delocalized. A compound disclosed by the invention is comprised of an amide or one of its salts, including an anionic portion combined with at least one cationic portion $M^{+m}$ in sufficient numbers to ensure overall electronic neutrality; the compound is further comprised of M as a hydroxonium, a nitrosonium $NO^+$, an ammonium $—NH_4+$, a metallic cation with the valence m, an organic cation with the valence m, or an organometallic cation with the valence m. The anionic portion matches the formula $R_F—SO_x—N^-Z$, wherein $R_F$ is a perfluorinated group, x is 1 or 2, and Z is an electroattractive substituent. The compounds can be used notably for ionic conducting materials, electronic conducting materials, colorants, and the catalysis of various chemical reactions.

46 Claims, 2 Drawing Sheets

U.S. PATENT DOCUMENTS

| | | |
|---|---|---|
| 5,273,840 | 12/1993 | Dominey . |
| 5,446,134 | 8/1995 | Armand et al. . |
| 5,502,251 | 3/1996 | Pohmer et al. . |
| 5,514,493 | 5/1996 | Waddell et al. . |
| 5,609,990 | 3/1997 | Ha et al. . |
| 5,654,112 | 8/1997 | Itou et al. . |
| 5,691,081 | 11/1997 | Krause et al. . |
| 5,817,376 | 10/1998 | Everaerts et al. . |
| 5,874,616 | 2/1999 | Howells et al. . |
| 5,962,546 | 10/1999 | Everaerts et al. . |
| 6,063,522 | 5/2000 | Hamrock et al. ............... 429/200 |

FOREIGN PATENT DOCUMENTS

| | | |
|---|---|---|
| WO 96/24928 | 8/1996 | (WO) . |
| WO 96/24929 | 8/1996 | (WO) . |
| WO 97/23448 | 7/1997 | (WO) . |
| WO 97/35929 | 10/1997 | (WO) . |
| WO 97/35930 | 10/1997 | (WO) . |
| WO 98/50349 | 11/1998 | (WO) . |
| WO 00/10969 | 3/2000 | (WO) . |
| WO 00/11742 | 3/2000 | (WO) . |

* cited by examiner

PERFLUORINATED AMIDE SALTS AND THEIR USES AS IONIC CONDUCTING MATERIALS

BACKGROUND OF THE INVENTION

1. Field of the Invention

The present invention relates to ionic compounds in which the anionic charge is delocalized, and their uses.

2. Description of the Background

It is known and it is particularly interesting to introduce ionic groups in molecules or organic polymers having various functions. Coulombic stresses correspond, indeed, to the stronger interactions which are available at the molecular level, and the ionic groups modify in an utmost manner the molecules to which they are bonded. Coloring matters which are made soluble in water by means of sulfonate or carboxylate functions may be mentioned.

However, the groups of this types, $-CO_2^-1/mM^{m+}$ or $-SO_3^- 1/mM^{m+}$, are not dissociated, and they do not induce solubility in solvents other than water or certain highly polar protic solvents such as light alcohols, which considerably restrict the scope of their utilization.

On the other hand, salts of the compounds $[R_FSO_2-N-SO_2R_F]^- 1/mM^{m+}$ in which $R_F$ is a perfluorinated group and $M^{m+}$ is a cation of valence m+ are known, which are soluble and are dissociated in organic aprotic media or solvating polymers. It is however considered that the existence of two perfluoroalkylsulfonyl groups (in particular the existence of fluorine atoms on the α atom of carbon of each sulfonyl group) which exert an important attracting power on the electrons of the ionic charge, is a necessary condition to obtaining properties of solubility and dissociation. For example, the $pK_a$ of the acid $H[CF_3SO_2-N-SO_2CF_3]$ is only 1.95, which compares to that of the non-fluorinated acid $CH_3SO_3H$ ($pK_a=0.3$) and is clearly inferior to that of perfluorinated acid $CF_3SO_3H$ ($pK_a<-9$) because of the basic character of the central nitrogen atom with respect to the oxygen atom of sulfonic acids.

SUMMARY OF THE INVENTION

Surprisingly, the inventors have found that the excellent properties of solubility and dissociation of the ionic groups $-SO_2-N-SO_2-$ were maintained when a single sulfonated group has fluorine atoms on atoms which are adjacent to the sulfur atom, giving an extremely wide choice of functional molecules. In a manner also quite unexpected, it has been noted that it was possible for obtaining the same properties, to omit the group $-SO_2$ bound to the non-perfluorinated group provided that the group which is directly bound to nitrogen has a Hammett parameter σ* higher than 0.6. By way of comparison, the Hammett parameters σ* of a group $-SO_2-$ bound to a non-perfluorinated group is 3.5 and 4.55 for a group $CF_3SO_2-$.

The present inventors have also found that the sulfonyl $-SO_2-$ groups could be replaced, with minor variations of properties, by sulfinyl $-SO-$ or phosphonyl $-PO=$ groups.

It is consequently an object of the present invention to provide a family of ionic compounds having a good solubility and a good dissociation, without having to rely on complex modifications of the starting molecule. The precursors of the molecule of the invention are found in the form of derivatives of sulfonic acids or of amine groups on the one hand, and derivatives of perfluorosulfonyl types on the other hand, which for the most part are industrial products and/or are easily accessible. In addition, it should be noted that a decrease of the perfluorinated fraction in the compounds of the invention enables to reduce the production costs of said compounds and consequently the cost of the applications in which they are involved.

BRIEF DESCRIPTION OF THE DRAWINGS

A compound of the present invention is an ionic compound consisting of an amide or one of its salts, comprising an ionic part associated with at least a cationic part $M^{m+}$ in sufficient number to ensure an electronic neutrality to the assembly. It is characterized in that $M^{m+}$ is a hydroxonium, a nitrosonium $NO^+$, an ammonium $-NH_4^+$, a metallic cation having a valency m, an organic cation having a valency m, or an organo-metallic cation having a valency m, and in that the anionic part corresponds to the formula $R_F-SO_x-N^-Z$, in which:

the group $-SO_x-$ represents a sulfonyl group $-SO_2-$ or a sulfinyl group $-SO-$;

Figure 1:
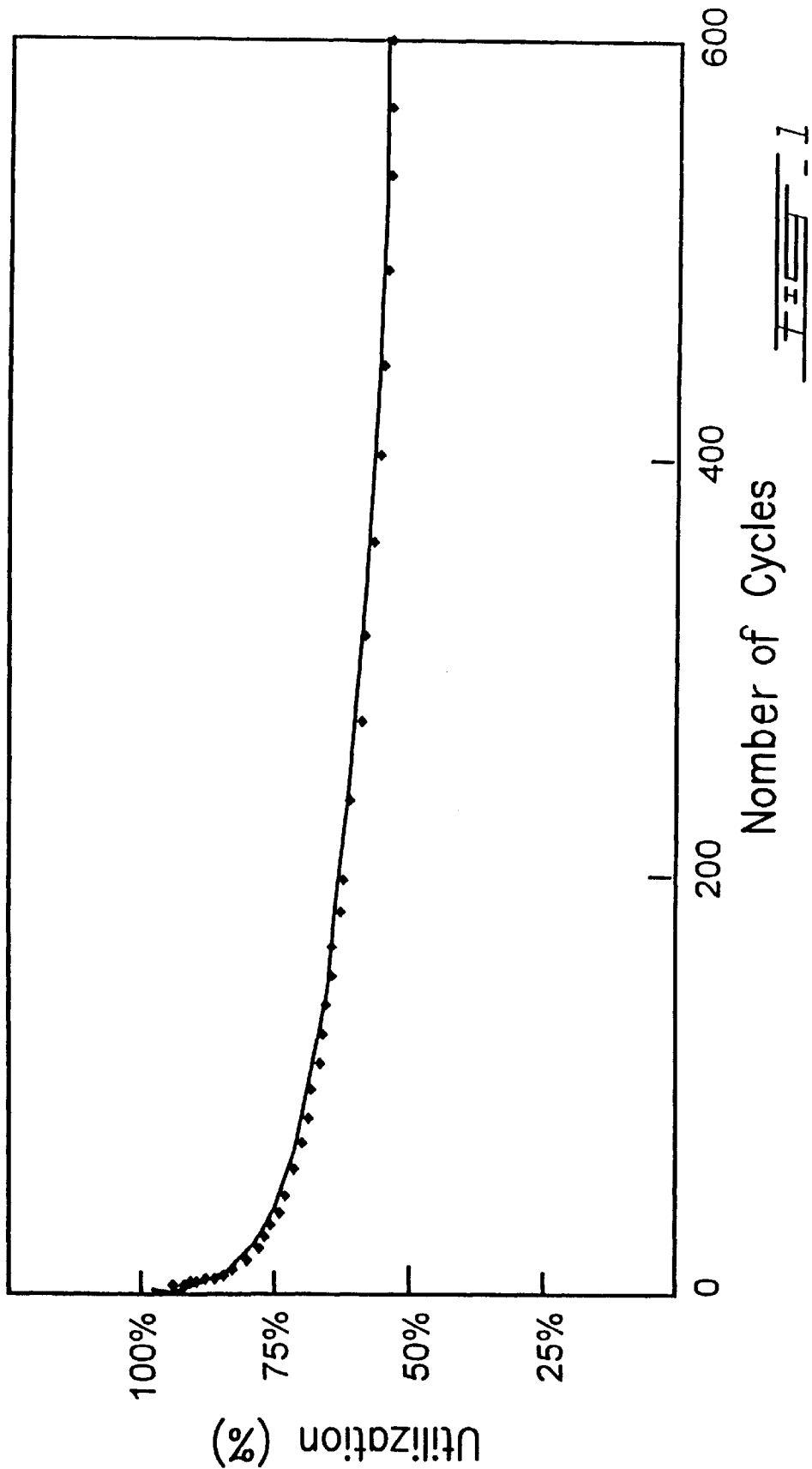

$R_F$ is a halogen or a perhalogenated alkyl, alkylaryl, oxa-alkyl, aza-alkyl or thia-alkyl radical, or a radical corresponding to one of the formulae $R_ACF_2-$, $R_ACF_2CF_2-$, $R_ACF_2CF(CF_3)-$ or $CF_3C(R_A)F-$ in which $R_A-$ represents a non-perhalogenated organic radial;

Z represents an electro-attractor radical having a Hammett parameter at least equal to that of a phenyl radical, and selected from:

j) $-CN$, $-NO_2$, $-SCN$, $-N_3$, $-CF_3$, $R'_FCH_2-$ ($R'_F$ being a pair of fluorinated radicals, preferably $CF_3-$), fluoroalkyloxy radicals, fluoroalkylthioxy radicals, jj) radicals comprising one or a plurality of aromatic nuclei possibly containing at least one nitrogen, oxygen, sulfur or phosphorus atom, said nuclei possibly being condensed nuclei and/or said nuclei possibly carrying at least one substitutent selected from halogens, $-CN$, $-NO_2$, $-SCN$, $-N_3$, $-CF_3$, $CF_3CH_2-$, $CF_2=CF-O-$, perfluoroalkyl groups, fluoroalkyloxy groups, fluoroalkylthioxy groups, alkyl, alkenyl, oxa-alkyl, oxa-alkenyl, aza-alkyl, aza-alkenyl, thia-alkyl, thia-alkenyl groups, polymer radicals and radicals having at least one cationic ionophoric group and/or at least one anionic ionophoric group;

it being understood that a substituent Z may be a monovalent radical, part of a multivalent radical carrying a plurality of groups $R_F-SO_x-N-$, or a segment of a polymer; or Z is a radical $R_D-Y-$ in which Y is a sulfonyl, sulfmyl or phosphonyl group and $R_D$ is a radical selected from the group consisting of:

a) alkyl or alkenyl radicals, aryl, arylalkyl, alkylaryl or alkenylaryl radicals, alicyclic or heterocyclic radicals, including polycyclic radicals;

b) alkyl or alkenyl radicals comprising at least one functional ether, thioether, amine, imine, carboxyl, carbonyl, hydroxy, silyl, isocyanate or thioisocyanate functional group;

c) aryl, arylalkyl, arylalkenyl, alkylaryl or alkenylaryl radicals, in which the aromatic nuclei and/or at least one substitutent of the nucleus comprises heteroatoms such as nitrogen, oxygen, sulfur;

d) radicals comprising condensed aromatic cycles which possibly comprise at least one heteroatom selected from nitrogen, oxygen, sulfur;

e) halogenated alkyl, alkenyl, aryl, arylalkyl, alkylaryl or alkenylaryl radicals in which the number of carbon atoms carrying at least one halogen is at most equal to the number of non-halogenated carbon atoms, the α carbon of group Y not being halogenated when Y is —SO$_2$—, said radicals possibly comprising functional ether, thioether, amine, imine, carboxyl, carbonyl, hydroxy, silylalkyl, silylaryl, isocyanate or isothiocyanate groups;

f) radicals R$_c$C(R') (R")—O— in which R$_c$ is a perfluorinated alkyl radical and R' and R" are independently from one another an hydrogen atom or a radical such as defined in a), b), c) or d) above [for example CF$_3$CH$_2$O—, (CF$_3$)$_3$CO—, (CF$_3$)$_2$CHO—, CF$_3$CH(C$_6$H$_5$)O—, —CH$_2$(CF$_2$)$_2$CH$_2$—];

g) radicals (R$_B$)$_2$N—, in which the radicals R$_B$ are identical or different and are as defined in a), b), c), d) and e) above, one of the R$_B$ could be an hydrogen atom or the two radicals R$_B$ together forming a bivalent radical which constitutes a cycle with N;

h) radicals constituted by a polymer chain;

i) radicals having one or more cationic ionophoric groups and/or one or more anionic ionophoric groups;

it being understood that a substituent R$_D$ could be a monovalent radical, part of a multivalent radical carrying a plurality of groups R$_F$—SO$_x$—N—Y—, or a segment of a polymer;

it being understood that when Y is a sulfonyl and when R$_D$ is a radical as defined in a), R$_F$ is R$_A$CF$_2$—, R$_A$CF$_2$CF$_2$—, R$_A$CF$_2$CF(CF$_3$)—, CF$_3$C(R$_A$)F— or a perhaloalkyl radical having 1 to 2 carbon atoms not favouring a phase separation due to the aggregation of the fluorinated segments.

In a compound of the present invention, the cation may be a metallic cation selected from cations of alkali metals, cations of alkali-earth metals, cations of transition metals, cations of tri-valent metals, cations of a rare earth. By way of example, Na$^+$, Li$^+$, K$^+$, Sm$^{3+}$, La$^{3+}$, Ho$^{3+}$, Sc$^{3+}$, Al$^{3+}$, Y$^{3+}$, Yb$^{3+}$, Lu$^{3+}$, Eu$^{3+}$ may be cited.

The cation may also be an organo-metallic cation, for example a metallocenium. By way of example, there may be mentioned the cations derived from ferrocene, titanocene, zirconocene, indenocenium or a metallocenium arene, cations of transition metals complexed with ligands of a phosphine type possibly having a chirality, organo-metallic cations having one or more alkyl or aryl groups co-valently fixed to an atom or a group of atoms, such as methylzinc, phenylmercury, trialkyltin or trialkyllead cations. The organo-metallic cations may be part of a polymer chain.

According to a variant of the invention, the compounds of the invention have an organic cation selected from the group consisting of R$_3$O$^+$ (oxonium), NR$_4$$^+$ (ammonium), RC(NHR$_2$)$_2$$^+$ (amidinium), C(NHR$_2$)$_3$$^+$ (guanidinium), C$_5$R$_6$N$^+$ (pyridinium), C$_3$R$_5$N$_2$$^+$ (imidazolium), C$_3$R$_7$N$_2$$^+$ (imidazolinium), C$_2$R$_4$N$_3$$^+$ (triazolium), SR$_3$$^+$ (sulfonium), PR$_4$$^+$ (phosphonium), IR$_2$$^+$ (iodonium), (C$_6$R$_5$)$_3$C+ (carbonium) cations. In a given cation, the radicals R may all be identical. However, a cation may also include radicals R which are different from one another. A radical R may be a H or it may be selected from the following radicals:

alkyl, alkenyl, oxa-alkyl, oxa-alkenyl, aza-alkyl, aza-alkenyl, thia-alkyl, thia-alkenyl, sila-alkyl, sila-alkenyl, aryl, arylalkyl, alkyl-aryl, alkenyl-aryl, dialkylamino and dialkylazo radicals;

cyclic or heterocyclic radicals possibly comprising at least one lateral chain comprising heteroatoms such as nitrogen, oxygen, sulfur;

cyclic or heterocyclic radicals possibly comprising heteroatoms in the aromatic nucleus;

groups comprising a plurality of aromatic or heterocyclic, condensed or non-condensed nuclei, possibly containing at least one nitrogen, oxygen, sulfur or phosphorus atom.

When an onium cation carries at least two radicals R which are different from H, these radicals may constitute together a cycle which is aromatic or non-aromatic, possibly enclosing the center carrying the cationic charge.

When the cationic part of a compound of the invention is an onium cation, it may be either in the form of an independent cationic group which is bound to the anionic part only by the ionic bond between the positive charge of the cation and the negative charge of the anionic part. In this case, the cationic part may be part of a recurring unit of a polymer.

An onium cation may also be part of the radical Z or the radical R$_D$ carried by the anionic centre. In this case, a compound of the invention constitutes a zwitterion.

When the cation of a compound of the invention is an onium cation, it may be selected so that it can introduce into the compound substituents permitting to confer specific properties to said compound. For example, the cation M$^+$ may be a cationic heterocycle with aromatic character, including at least one alkylated nitrogen atom in the cycle. By way of example, there may be cited an imidazolium, a triazolium, a pyridinium, a 4-dimethylamino-pyridinium, said cations possibly carrying a substituent on the carbon atoms of the cycle. Among these cations, those which give an ionic compound according to the invention in which the melting point is lower than 150° C. are particularly preferred. Such a compound having a low melting point is particularly useful for the preparation of materials with protonic conduction. A material with protonic conduction which is particularly preferred comprises a compound according to the invention in which the cation is formed by addition of a proton on the nitrogen of an imidazoline, an imidazole or a triazole, as well as the nitrogenated corresponding base in a proportion of 0.5 to 10 in molar ratio.

A compound of the invention in which the cation M is a cationic group having a bond —N═N—, —N═N$^+$, a sulfonium group, an iodonium group, or a substituted or non-substituted arene-ferrocenium cation, possibly incorporated in a polymeric network, is interesting insofar as it can be activated by a source of actinic energy of suitable wavelength. Particular examples of such compounds include those in which the cation is a diaryliodonium, dialkylaryliodonium, triarylsulfonium, trialkylaryl sulfonium, or phenacyl-dialkyl sulfonium radical which is substituted or non-substituted. The above cations may be part of a polymer chain.

The cation M of a compound of the invention may include a group 2,2'[azobis(2-2'-imidazolinio-2-yl)propane]$^{2+}$ or 2,2'-azobis(2-amidiniopropane)$^{2+}$. The compound of the invention is then capable of releasing, under the action of heat or an ionizing radiation, radicals which enable initiation of polymerization, cross-linking reactions or, in a general manner, chemical reactions involving free radicals. Moreover, these compounds are easily soluble in polymeric and monomeric organic solvents even of low polarity, contrary to the derivatives of anions of the type Cl$^-$ normally associated with this type of compounds. On the other hand, they have a negligible vapour pressure contrary to the other radical initiators of the peroxide or azo type, which is a considerable advantage for the preparation of thin polymer films, the volatility of the initiator having as a consequence a bad polymerization or cross-lining of the surface of the film.

In an embodiment of the invention, $R_F$ is a fluorine atom or a pair of halogenated alkyl radicals preferably having from 1 to 12 carbon atoms, or a pair of halogenated alkylaryl radicals preferably having from 6 to 9 carbon atoms. The pair of halogenated alkyl radicals may be a linear or branched radical. In particular, radicals in which the carbon atom which will be in a position with respect to the group —$SO_x$— carries at least one fluorine atom, may be cited. Examples of such radicals include $R_ACF_2$—, $R_ACF_2CF_2$—, $R_ACF_2CF(CF_3)$— or $CF_3C(R_A)F$— in which $R_A$ represents a non-perhalogenated organic radical, an alkyl group, an aryl group, an alkylaryl or arylalkyl group; a group comprising at least one ethylenic unsaturation and/or a condensable group and/or a dissociable group; a mesomorphous group; a chromophorous group; a self-doped electronic conductive polymer; a hydrolyzable alkoxysilane; a polymer chain carrying grafts including a carbonyl group, a sulfonyl group, a thionyl group or a phosphonyl group; a group capable of trapping free radicals such as a crowded phenol or a quinone; a dissociating dipole such as an amide, a sulfonamide or a nitrile; a redox pair such as a disulfide, a thioamide, a ferrocene, a pheno-thiazine, a bis(dialkylaminoaryl) group, a nitroxide or an aromatic imide; a complexing ligand; a zwitterion, an optically or biologically active amino acid or a polypeptide; a chiral group.

The choice of substituent Z enables to adjust the properties of a compound of the invention.

A particular family of compounds of the invention is the one in which Z represents a group $R_DY$—. The compounds in which Y is —$SO_2$— are especially preferred.

In an embodiment, $R_D$ is selected from alkyl, alkenyl, oxa-alkyl, oxa-alkenyl, aza-alkyl, aza-alkenyl, thia-alkyl or thia-alkenyl radicals having from 1 to 24 carbon atoms, or from aryl, arylalkyl, alkylaryl or alkenylaryl radicals having from 5 to 24 carbon atoms.

In another embodiment, $R_D$ is selected from alkyl or alkenyl radicals having from 1 to 12 carbon atoms and possibly comprising at least one heteroatom O, N or S in the main chain or in a lateral chain, and/or possibly carrying a hydroxy group, a carbonyl group, an amino group or a carboxyl group.

A substituent $R_D$ may be a polymer radical, for example an oligo(oxyalkylene) radical. The compound of the invention then appears in the form of a polymer carrying an ionic group —$[Y$—$N$—$SO_x$—$R_F]^-$, $M^+$.

$R_D$ may be a recurring unit of a polymer, for example an oxyalkylene unit or a styrene unit. The compound of the invention then appears in the form of an polymer in which at least part of the recurring units carry a lateral group on which an ionic group —$[Y$—$N$—$SO_x$—$R_F]^-$, $M^+$ is bonded. By way of example, a poly(oxyalkylene) in which at least certain oxyalkylene units carry a substituent —$[Y$—$N$—$SO_x$—$R_F]^-$, $M^+$, or a polystyrene in which at least certain styrene units carry a substituent —$[Y$—$N$—$SO_x$—$R_F]^-$, $M^+$, for example [styrenyl—$Y$—$N$—$S(O)_x$—$R_F]^-$, may be mentioned.

A particular category of compounds of the invention comprises the compounds in which the substituent $R_D$ has at least one anionic ionophoric group and/or at least one cationic ionophoric group. The anionic group may for example be a carboxylate (—$CO_2^-$), a sulfonate fiction (—$SO_3^-$), a sulfonimide function (—$SO_2NSO_2$—) or a sulfonamide function (—$SO_2N$—). The cationic ionophoric group may for example be an iodonium, sulfonium, oxonium, ammonium, amidinium, guanidinium, pyridinium, imidazolium, imidazolinium, triazolium, phosphonium or carbonium group. The cationic ionophoric group may totally or partially play the role of the cation M.

When $R_D$ includes at least ethylenic unsaturation and/or a condensable group and/or a group which is dissociable by thermal or photochemical means or by ionic dissociation, the compounds of the invention are reactive compounds which may be subject to polymerizations, cross-linkings or condensations, optionally with other monomers. They may also be used to fix ionophoric groups on the polymers carrying a suitable reactive function.

A substituent $R_D$ may be a mesomorphous group or a chromophorous group or a self-doped electronically conductive polymer or a hydrolyzable alkoxysilane.

A substituent $R_D$ may include a group capable of trapping free radicals, for example, a hindered phenol or a quinone.

A substituent $R_D$ may also include a bipolar dissociating agent, for example, an amide function, a sulfonamide function or a nitrile fictions.

A substituent $R_D$ may also include a redox couple, for example, a disulfide group, a thioamide group, a ferrocene group, a phenothiazine group, a bis(dialkylaminoaryl) group, a nitroxide group or an aromatic imide group.

A substituent $R_D$ may also include a complexing ligand or an optically active group.

Another category of compounds of the invention comprises compounds in which $R_D$—$Y$— represent an amino acid, or an optically or biologically active polypeptide.

According to a variant, a compound of the invention comprises a substituent $R_D$ which represents a radical having a valency v higher than 2, itself including at least one group $R_F$—$S(O)_x$—$N$—$Y$—. In this case, the negative charges present on the anionic part of the compound of the invention should be compensated by an appropriate number of cations or ionophorous cationic groups M.

When a compound of the present invention corresponds to the formula $R_F$—$S(O)_x$—$N$—Z, in which Z is an electroattractive group which is not bonded to the nitrogen which carries the negative charge by a group Y, Z is advantageously selected from the group consisting of —CN, —$OC_nF_{2n+1}$, —$OC_2F_4H$, —$SC_nF_{2n+1}$ and —$SC_2F_4H$, —O—$CF$=$CF_2$, —$SCF$=$CF_2$, n being a whole number from 1 to 8. Z may also be a radical $C_nF_{2n+1}CH_2$—, n being a whole number from 1 to 8, or among the heterocyclic compounds, in particular those derived from pyridine, pyrazine, pyrimidine, oxadiazole, thiadiazole, which are fluorinated or non-fluorinated. Z may also represent a recurring unit of a polymer. The compound of the invention is then in the form of a polymer in which at least part of the recurring units carry a lateral group on which an ionic group —[(N—$SO_x$—$R_F$)$^-$, $M^+$] is fixed. By way of example, a polymer comprising one of the following recurring units may be mentioned:

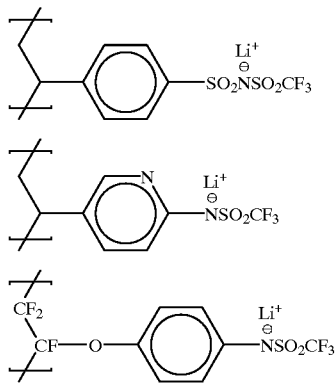

or a polyzwitterion of a conductive polymer which is a self-doped polyaniline in which the recurring unit is:

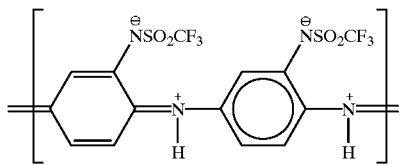

The compounds of the invention may be obtained by a process in which a compound $R_FSO_x$—L is reacted with a compound [A—N—Z]$^{n-m}$ nM$^{m+}$, $R_F$, x, M and Z being as previously defined, L representing an electronegative starting group such as a halogen, a N-imidazoyl radical, a N-triazoyl radical, a radical $R_FSO_{x+1}$— and A represents a cation M$^{m+}$, a trialkylsilyl group, a trialkylgermanyl group, a trialkyistannyl group or a tertiaiyalkyl group, in which the alkyl substituents have from 1 to 6 carbon atoms. By way of example, the reaction of a fluorosulfonyl fluoride with a bi-salt of cyanamide according to the following reaction scheme may be mentioned:

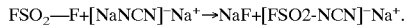

FSO$_2$—F+[NaNCN]$^-$Na$^+$→NaF+[FSO2-NCN]$^-$Na$^+$.

The reaction of a substituted aniline with trifluoromethanesulfonic anhydride may also be mentioned.

The compounds in which Z represents $R_D$Y— may be obtained by a process in which a compound $R_D$—Y—L is reacted with a compound [$R_FSO_x$—N—A]$^{n-}{}_m$nM$^{m+}$. By way of example of such a process, the reaction of a perfluorosulfonamide or one of its salts with a sulfonyl halide may be mentioned.

The use of a compound [A—N—Z]$^{n-}$m nM$^{m+}$ in which A is a tertiary alkyl group is advantageous, because such a group is a proton precursor by formation of the corresponding alkene. The use of a trialkylsilyl is especially interesting when the starting group is a fluorine atom, by reason of the very high stability of the bond F—Si.

When there is used a compound [A—N—Z]$^{n-}{}_m$ nM$^{m+}$ in which A is the proton, it is advantageous to carry out the reaction in the presence of a tertiary base or crowded base T capable of forming the salt L$^-$(HT$^+$) by combination of the proton, in order to promote the formation of the compound of the invention. The base may be selected from alkylamines (for example triethylamine, diisopropylamine, quinuclidine), 1,4-diazobicyclo[2,2,2]octane (DABCO); pyridines (for example pyridine, alkylpyridines, dialkylaminopyridines); imidazoles (for example N-alkylimidazoles, imidazo[1,1-a]pyridine); amidines (for example 1,5-diazabicyclo[4,3,0]non-5-ene (DBN), 1,8-diazabicyclo[5,4,0]undec-7-ene (DBU)); guanidines (for example tetramethyl guanidine, 1,3,4,7,8-hexahydro-1-methyl-2H-pyrimido[1,2-a]pyrinmidine (HPP).

By way of example of such a process, the process in which a sulfonyl chloride $R_DSO_2$Cl is reacted with a perfluorosulfonamide in the presence of DABCO may be mentioned.

A compound according to the invention may also be obtained by reacting perfluorosulfonic acid or one of its salts with a compound (R$^i$)$_3$P═N—Z in which the R$^i$ represent independently from one another an alkyl radical, an aryl radical or a dialkylamino radical. In the same manner, an acid $R_DSO_x$—OH or one of its salts may be reacted with a compound (R$^i$)$_3$P═N—SO$_x$R$_F$. By way of example, the reaction of a sodium alkylsulfonate with $R_FSO_2$N═P(C$_6$H$_5$)$_3$ may be mentioned.

The cation of a compound obtained according to either one of the processes described above may be replaced by known processes of cation exchange, either by precipitations or selective extractions, or by the use of ion exchange resins.

In addition, the substituent $R_D$ of a compound of the invention may be modified by means of known reactions. For example, a substituent $R_D$ which comprises an allyl group may be converted by reaction with a peroxide to give an epoxidized substituent $R_D$. A group —NHR may be converted into a vinylester group by reaction with a strong base such as potassium tert-butoxide, then with vinylchloroformate. The processes enabling to carry out these modifications and others are available to those skilled in the art. Of course, the functions carried by radical $R_A$ and R which could interfere with the reactions leading to the preparation of the compounds of the invention may be temporarily protected by means of known techniques. For example, an amine function may be protected by a group t-BOC (tertiobutoxycarbonyl) which is stable in the presence of bases T but which is easily removed by treatment in an acid medium.

The ionic compounds of the present invention comprise at least one ionophoric group on which substituents which can vary to a large extent are fixed. Taking into account the large choice possible for the substituents, the compounds of the invention enable the production of properties of ionic conduction in most of the organic media, liquids or polymers having even a low polarity. The applications are important in the field of electrochemistry, in particular for storing energy in primary or secondary generators, in supercapacitances, in combustible batteries and in electroluminescent diodes. The compatibility of the ionic compounds of the invention with polymers or organic liquids enable to induce noted antistatic properties, even when the content of ionic compound is extremely low. The compounds of the invention which are polymers, as well as polymer compounds obtained from the compounds of the invention having the property of polymerizing or co-polymerizing, show the properties mentioned above with the advantage of having an immovable anionic charge. This is why another object of the present invention resides in an ionically conductive material consisting of an ionic compound of the present invention in solution in a solvent.

In an embodiment, the ionic compound used for the preparation of an ionically conductive material is selected from the compounds in which the cation is ammonium, or a cation derived from a metal, in particular lithium or potassium, zinc, calcium, metals of rare earths, or an organic cation, such as a substituted ammonium, an imidazolium, a triazolium, a pyridinium, a 4-dimethylamino-pyridinium, said cations optionally carring a substituent on the carbon atoms of the cycle. The ionically conductive material thus obtained has an elevated conductivity and solubility in solvents, resulting from weak interactions between the positive charge and the negative charge. Its field of electrochemical stability is extended, and it is stable in reducing as well as oxidizing media. Moreover, the compounds which have an organic cation and a melting point lower than 150° C., in particular imidazolium, triazolium, pyridinium, 4-dimethylamino-pyridinium compounds have an intrinsic elevated conductivity, even in the absence of solvent, when they are in molten phase.

The materials with ionic conduction which incorporate a compound of the invention in which $R_F$ is a fluorine atom or a perhalogenated allyl radical having from 1 to 12 carbon atoms, or a perhalogenated alkylaryl radical having from 6 to 9 carbon atoms are interesting to the extent that the low interactions between the atoms of fluorine of the chain result in high solubility and conductivity, even in the case where the remainder of the molecule contains groups having a tendency to give strong interactions such as conjugated aromatic radicals or zwitterions.

The choice of a compound of the invention in which $R_F$ is selected from the radicals $R_ACF_2$—, $R_ACF_2CF_2$—, $R_ACF_2CF(CF_3)$— or $CF_3C(R_A)F$— enable it to very precisely adapt the properties of the ionically conductive material by selecting the substituent $R_A$ in an appropriate manner. In particular, they permit to rely, with a reduced number of fluorine atoms, on the properties of dissociation and of solubility inherent to the anionic charges of the perfluorinated systems. These groups are easily accessible from industrial products such as tetrafluoroethylene or tetrafluoropropylene. The reduced quantity of fluorine renders these compounds less susceptible to reduction by metals which are even electropositive, such as aluminum, magnesium or especially lithium.

The properties of the ionically conductive material may also be adapted by the choice of the substituent $R_D$.

The choice for $R_A$ or $R_D$ of an alkyl group, an aryl group, an alkylaryl group or an arylalkyl group, enables to introduce into the ionically conductive material properties of mesogene type, in particular allyl groups having from 6 to 20 carbon atoms, aryl-alkyl groups, in particular those containing the biphenyl entity which form phases of the liquid crystal type. Properties of conduction in phases of the liquid crystal, nematic, cholesteric or discotic types, are interesting for applications relating to optical posting or to reduce the mobility of anions in the electrolytes, in particular in polymer electrolytes, without affecting the mobility of the cations. This characteristic is important for applications in electrochemical generators, and particularly those involving lithium cations.

When the substituent $R_A$ is a mesomorphous group or a group comprising at least one ethylenic unsaturation and/or a condensable group and/or a group which is dissociable by thermal means, by photochemical means or by ionic dissociation, or when $R_D$ is a substituent containing one of these groups, the ionically conductive material easily forms polymers or copolymers which are polyelectrolytes, either intrinsically when the polymer carries solvating groups, or by addition of a polar solvent of a liquid or polymer type, or by mixture with such a solvent. These products have a conductivity which is solely due to the cations, which constitutes a property which is very useful in the applications of the electrochemical generator type. In low molar fraction in a copolymer, they produce antistatic properties which are stable and are little dependent on humidity, and promote the fixation of cationic coloring materials, this property being useful for textile fibres and lasers with coloring materials.

The presence of a substituent $R_A$ or $R_D$ which is a self-doped electronically conductive polymer improves the stability of the ionically conductive material as compared to outside agents. The conductivity is stable in time, even at elevated temperatures. In contact with metals, these materials give very low interface resistance and, in particular, protect ferrous metals or aluminum against corrosion.

When the substituent $R_A$ or $R_D$ is an hydrolyzable alkoxysilane, the ionically conductive material may form stable polymers by the simple mechanism of hydrolysis-condensation in the presence of water, thereby enabling treatment of oxide, silica, silicate, in particular glass surfaces to induce properties of surface conduction, antistatic properties, or to promote the adhesion of polar polymers.

When the substituent $R_A$ or $R_D$ is a group comprising a free radical trap such as a congested phenol or a quinone, the ionically conductive material has the following advantages and properties: it acts as an antioxidant with no volatility and being compatible with polar monomers and polymers, to which it additionally provides antistatic properties.

When the substituent $R_A$ or $R_D$ comprises a dissociating dipole such as an amide, a sulfonamide or a nitrile, the ionically conductive material has an improved conductivity in media with low or average polarity, in particular in solvating polymers, which enables to minimize, even to remove the addition of solvents or volatile plasticizing agents.

The presence of a substituent $R_A$ or $R_D$ which contains a redox couple such as a disulfide, a thioamide, a ferrocene, a pheno-thiazine, a bis(dialkylaminoaryl) group, a nitroxide, an aromatic imide, enables introduction into the ionically conductive material shuttle redox properties which are useful as an element for the protection and the equalization of the charge of electrochemical generators, in photoelectrochemical systems, in particular for converting light into electricity, in systems for modulating light of the electrochrome type.

The presence of a substituent $R_A$ or $R_D$ which is a complexing ligand in an ionically conductive material enables chelation of metallic cations, in particular those which possess an elevated charge (2, 3 and 4), in the form of a complex which is soluble in organic media, including aprotic media, and enable transportation of these cations in particular in the form of an anionic complex, in solvating polymers. The metallic cations of elevated charge are indeed immovable in solvating polymers. This type of complexing gives redox couples which are particularly stable, with certain cations of transition metals (Fe, Co . . . ) or certain rare earths (Ce, Eu . . . ).

The ionically conductive materials containing a compound of the invention in which $R_D$ is an alkyl or an alkenyl substituent which contains at least one heteroatom selected from O, N and S have a complexing and plasticizing property, in particular in polar polymers and especially polyethers. The heteroatoms N and S are selectively complexing for cations of transition metals, Zn and Pb.

When a substituent $R_D$ alkyl or alkenyl additionally carries an hydroxy group, a carbonyl group, an amino group, a carboxyl group, an isocyanate group or a thioisocyanate group, the ionic compound of the invention may give by polycondensation a polymer or copolymer and the ionically conductive material which contains such a polymer or copolymer shows polyelectrolyte properties.

The presence, in the ionically conductive material of the invention, of a compound in which $R_D$ is selected from radicals aryl, arylalkyl, alkylaryl or alkenylaryl, in which the lateral chains and/or the aromatic nuclei comprise heteroatoms such as nitrogen, oxygen, sulfur, improves dissociation and increases the possibility of forming complexes depending on the position of the heteroatom (pyridine), or of giving by duplicating oxidation conjugated polymers or copolymers (pyrrol, thiophene).

When the ionically conductive material contains a compound of the invention in which $R_D$ represents a recurring unit of a polymer chain, the material constitutes a polyelectrolyte.

A compound of the invention in which the substituent Z is selected from the group consisting of —$OC_nF_{2n+1}$, —$OC_2F_4H$, —$SC_nF_{2n+1}$ and —$SC_2F_4H$, —$OCF=CF_2$, —$SCF=CF_2$, n being a whole number from 1 to 8, is a precursor of stable monomers and polymers in particular towards oxygen even at temperatures higher than 80° C. when dealing with polymers. An ionically conductive material which contains such a compound is therefore particularly suitable as as electrolyte of a combustible battery.

An ionically conductive material of the present invention comprises an ionic compound of the invention in solution in a solvent.

The solvent may be an aprotic liquid solvent, a polar polymer or a mixture thereof.

The aprotic liquid solvent is selected for example among linear ethers and cyclic ethers, esters, nitriles, nitro derivatives, amides, sulfones, sulfolanes, alkylsulfamides and partially halogenated hydrocarbons. Particularly preferred solvents include diethylether, dimethoxyethane, glyme, tetrahydrofurane, dioxane, dimethyltetrahydrofurane, methylformate or ethylformate, propylene or ethylene carbonate, alkyl carbonates (such as dimethyl carbonate, diethyl carbonate and methylpropyl carbonate), butyrolactones, acetonitrile, benzonitrile, nitromethane, nitrobenzene, dimethylformamide, diethylformamide, N-methylpyrrolidone, dimethylsulfone, tetramethylene sulfone and tetraalkylsulfonamides having from 5 to 10 carbon atoms.

The polar polymer may also be selected from a cross-linked or non cross-linked solvating polymer, with or without grafted ionic groups. A solvating polymer is a polymer which includes solvating units containing at least one heteroatom selected from sulfur, oxygen, nitrogen and fluorine. By way of example of solvating polymers, there may be mentioned polymers with linear structure, comb or block type, which may or may not form a network, based on poly(ethylene oxide), or copolymers containing an ethylene oxide, propylene oxide or allylglycidylether unit, polyphorphazenes, cross-linked network based on polyethylene glycol cross-linked with isocyanates, or networks obtained by polycondensation and carrying groups which permit the incorporation of cross-inkable groups. Block copolymers in which certain blocks carry functions which have redox properties may also be mentioned. Of course, the above list is not limiting, and all the polymers having solvating properties may also be used.

An ionically conductive material of the present invention may a simultaneously comprise an aprotic liquid solvent selected from the above-mentioned aprotic liquid solvents and a polar polymer solvent comprising units containing at least one heteroatom selected from sulfur, nitrogen, oxygen and fluorine. It may comprise 2 to 98% liquid solvent. By way of example of such a polar polymer, polymers which mainly contain units derived from acrylonitrile, vinylidene fluoride, N-vinylpyrolidone or methyl methacrylate may be mentioned. The proportion of aprotic liquid in the solvent may vary from 2% (corresponding to a plasticized solvent) to 98% (corresponding to a gelled solvent).

An ionically conductive material of the present invention may additionally contain a salt commonly used in the prior art for preparing an ionically conductive material. Among the salts which may be used in admixture with an ionic compound according to the invention, a salt selected from the perfluoroalcanesulfonates, bis(perfluoroalkylsulfonyl) imides, bis(perfluoro-alkylsulfonyl)methanes and tris (perfluoroalkylsulfonyl)methanes is particularly preferred.

Of course, an jonically conductive material of the invention may additionally contain the additives known to be used with this type of material, for example mineral or organic charges in the form of a powder or fibres.

An ionically conductive material of the invention may be used as an electrolyte in an electrochemical generator. It is therefore an object of the present invention to provide an electrochemical generator comprising a negative electrode and a positive electrode, both being separated by an electrolyte, wherein the electrolyte is an ionically conductive material as defined above. According to a particular embodiment, such a generator comprises a negative electrode consisting of metallic lithium, or one of its alloys, optionally in the form of nanometric dispersion in lithium oxide, or a double nitride of lithium and a transition metal, or an oxide with low potential having the general formula $Li_{1+y+x/3}Ti_{2-x/3}O_4$ ($0 \leq x \leq 1, 0 \leq y \leq 1$), or carbon and carbonated products resulting from pyrolysis of organic materials. According to another embodiment, the generator comprises a positive electrode selected from vanadium oxide $VO_x$ ($2 \leq x \leq 2,5$), $LiV_3O_8$, $Li_yNi_{1-x}Co_xO_2$, ($0 \leq x \leq 1; 0 \leq y \leq 1$), magnesium spinels $Li_yMn_{1-x}M_xO_2$ (M=Cr, Al, V, Ni, $0 \leq x \leq 0,5; 0 \leq y \leq 2$), organic polydisulfides, FeS, $FeS_2$, ferric sulfate $Fe_2(SO_4)_3$, phosphates and phosphosilicates of iron and of lithium of olivine structure, or products wherein iron is substituted by manganese, used alone or in admixtures. The collector of the positive electrode is preferably aluminum.

An ionically conductive material of the present invention may also be used in a supercapacitance. Another object of the present invention is consequently a supercapacitance utilizing at least one carbon electrode with high specific surface, or an electrode containing a redox polymer, in which the electrolyte is an ionically conductive material as defined above.

An ionically conductive material of the present invention may also be used for the p or n doping of a polymer with electronic conduction and this use constitutes another object of the present invention.

In addition, an ionically conductive material of the present invention may be used as an electrolyte in an electrochrome device. An electrochrome device in which the electrolyte is an ionically conductive material according to the invention is another object of the present invention.

It has been noted that the strong dissociation of the ionic species of the compounds of the invention result in a stabilization of the carbocations, in particular those in which there is a conjugation with oxygen or nitrogen and, surprisingly in a strong activity of the proponic form of the compounds of the invention on certain monomers. It is also an object of the invention to provide for the utilization of the ionic compounds as photoinitiators which constitute sources of Brønsted acids, catalysts for the polymerization or cross-linking of monomers or prepolymers capable of cationic reaction, or as a catalysts for the modification of polymers.

The process of polymerization or cross-linking of monomers or prepolymers capable of cationic reaction is characterized in that there is used a compound of the invention as photoinitiator constituting a source of acid which catalyzes the polymerization reaction. The compounds according to the invention in which the cation is a group having a bond —N=N$^+$, —N=N—, a sulfonium group, an iodonium group, or an optionally substituted arene-ferrocenium cation, possibly incorporated in a polymeric skeleton, are particularly preferred.

The choice of substituent $R_F$ on the one hand, and of substituents $R_D$ or Z on the other hand, is made in a manner to increase the solubility of said compound in the solvents used for the reaction of the monomers or prepolymers, and as a function of the desired properties for the final polymer. For example, the choice of a non-substituted alkyl radicals gives solubility in low polar media. The choice of radicals comprising a group oxa or a sulfone gives solubility in polar media. The radicals including a sulfoxide group, a sulfone group, and a phosphine oxide group, a phosphonate group, respectively obtained by the addition of oxygen on the atoms of sulfur or phosphorus, may provide improved properties with respect to adhesion, glossiness, resistance to oxidation or UV to the polymer obtained. The monomers and polymers which may be polymerized or cross-linked by means of the photoinitiators of the present invention are those which may be subject to a cationic polymerization.

Among the monomers, those which include a cyclic ether function, a cyclic thioether function or a cyclic amino function, vinyl compounds (more particularly vinyl ethers), oxazolines, lactones and lactames may be mentioned.

Among the monomers of the cyclic ether or thioether type, ethylene oxide, propylene oxide, oxetane, epichlorhydrin, tetrahydrofurane, styrene oxide, cyclohexene oxide, vinylcyclohexene oxide, glycidol butylene oxide, octylene oxide, glycidyl ethers and esters (for example glycidyl methacrylate or acrylate, phenyl glycidyl ether, bisphenol A diglycidylether or its fluorinated derivatives), cyclic acetals having from 4 to 15 carbon atoms (for example dioxolane, 1,3-dioxane, 1,3-dioxepane) and spiro-bicyclo dioxolanes may be mentioned.

Among the vinyl compounds, vinyl ethers constitute a very important family of monomers which are subject to cationic polymerization. By way of example, there may be mentioned ethyl vinyl ether, propyl vinyl ether, isobutyl vinyl ether, octadecyl vinyl ether, ethyleneglycol monovinyl ether, diethyleneglycol divinyl ether, butanediol monovinyl ether, butanediol divinyl ether, hexanediol divinyl ether, ethyleneglycol butyl vinyl ether, triethyleneglycol methyl vinyl ether, cyclohexanedimenthanol monovinyl ether, cyclohexanedimethanol divinyl ether, 2-ethylhexyl vinyl ether, poly-THF-divinyl ether having a weight between 150 and 5000, diethyleneglycol monovinyl ether, trirethylolpropane trivinyl ether, aminopropyl vinyl ether, and 2-diethylaminoethyl vinyl ether.

Other vinyl compounds may include by way of example 1,1-dialkylethylenes (for example isobutene), aromatic vinyl monomers (for example styrene, α-alkylstyrene, such as α-methylstyrene, 4-vinylanisole, acenaphthene), N-vinyl compounds (for example N-vinylpyrolidone or N-vinyl sulfonamides).

Among the prepolymers, there may be mentioned the compounds in which the epoxy groups are carried by an aliphatic chain, an aromatic chain, or a heterocyclic chain, for example glycidyl ethers or bisphenol A which are ethoxylated by 3 to 15 ethylene oxide units, siloxanes having lateral groups of the type epoxycyclohexene-ethyl obtained by hydrosilylation of copolymers of dialkyl, alkylaryl or diaryl siloxane with methyl hydrogenosiloxane in the presence of vinylcyclohexene oxide, condensation products of the type sol-gel obtained from triethoxy or trimethoxy silapropylcyclohexene oxide, urethanes incorporating reaction products of monovinylether butanediol and an alcohol of a function higher than or equal to 2 with an aliphatic or aromatic di or tri isocyanate.

The process of polymerization according to the invention consists in mixing at least one monomer or prepolymer capable of cationic polymerization and at least one ionic compound of the invention, and subjecting the mixture obtained to actinic or β radiation. Preferably, the reaction mixture is subjected to irradiation after having been shaped as a thin layer having a thickness lower than 5 mm, preferably in the form of a thin film having a thickness lower than or equal to 500 μm. The duration of the reaction depends on the thickness of the sample and the power of the source at the active wavelength λ. It is deformed by the speed in front of the source, which is comprised between 300 m/min and 1 cm/min. Layers of fmal material having a thickness higher than 5 mm may be obtained by repeating many times the operation consisting of spreading a layer and treating it byu irradiation.

Generally, the quantity of photoinitiator used is between 0.01 and 15% by weight with respect to the weight of the monomer or prepolymer, preferably between 0.1 and 5% by weight.

An ionic compound of the present invention may be used as photoinitiator in the absence of solvent, for example when it is intended to polymerize liquid monomers in which the ionic compound used as photoinitiator is soluble or easily dispersible. This type of use is particularly interesting, since it permits to get rid of problems associated with solvents (toxicity, flammability).

An ionic compound of the present invention may also be used as photoinitiator in the form of a homogenous solution in a solvent which is insert during polymerization, which solution is ready to use and easily dispersible, in particular in the case where the mixture to be polymerized or cross-linked has a high viscosity.

As an example of inert solvent, there may be mentioned volatile solvents, such as acetone, methyl-ethyl ketone and acetonitrile. These solvents will merely be used for diluting the products to be polymerized or cross-linked (to make them less viscous, especially when dealing with a prepolymer). They will be eliminated by drying after polymerization or cross-linking. Non-volatile solvents may also be mentioned. A non-volatile solvent is also used for diluting the products that are intended to be polymerized or cross-linked, and to dissolve the salt $A^+X^-$ of the invention used as photoinitiator, however, it will remain in the material formed and will thus act as a plasticizing agent. By way of example, propylene carbonate, γ-butyrolactone, ether-esters of mono-, di-, tri- ethylene or propylene glycols, ether alcohol of mono-, di-, tri- ethylene or propylene glycols, plasticizing agents such as phthalic acid esters or citric acid esters may be mentioned.

According to another embodiment of the invention, there is used as solvent or diluent a compound which is reactive towards polymerization, which has a low molecular weight and low viscosity and which will act simultaneously as a polymerizable monomer and as solvent or diluent for more viscous monomers or prepolymers used jointly. After the reaction, these monomers which have been used as solvents will be part of the macromolecular network finally obtained, their integration being greater when dealing with bi-functional monomers. The material obtained after irradiation is now free of products having a low molecular weight and an appreciable vapour tension, or susceptible to contaminate objects with which the polymer is in contact. By way of example, a reactive solvent may be selected from mono- and di- vinyl ethers of mono-, di-, tri-, tetra- ethylene and propylene glycols, N-methylpyrolidone, 2-propenylether of propylene carbonate which is commercially available for example under the designation PEPC from ISP, New Jersey, United States.

To irradiate the reaction mixture, the irradiation may be selected from ultraviolet radiation, visible radiation, X-rays, γ rays and β radiation. When ultraviolet light is used as an actinic radiation, it may be advantageous to add to the photoinitiators of the invention photosensitizers intended to permit an efficient photolysis with wavelengths less energetic than those corresponding to a maximum of absorption of the photoinitiator, such as those emitted by industrial devices ($λ≈300$ nm with mercury vapour lamps in particular). Such additives are known, and by way of non-limiting example, there may be mentioned anthracene, diphenyl-9,10-anthracene, perylene, phenothiazine, tetracene, xanthone, thioxanthone, acetophenone, benzophenone, 1,3,5-triaryl-2-pyrazolines and derivatives thereof, in particular derivatives which are substituted on the aromatic nuclei by alkyl, oxa- or aza- alkyl radicals enabling among others to change the absorption wavelength. Isopropylthioxantone is a preferred example of photosensitizer when an iodonium salt according to the invention is used as a photoinitiator.

Among the various types of radiation mentioned, ultraviolet radiation is particularly preferred. On the one hand, it is easier to use than the other radiations mentioned above. On the other hand, photoinitiators are in general directly sensitive to UV rays and photosensitizers especially since the difference of energy ($\delta\lambda$) is lower.

The ionic compounds of the invention may also be used in association with initiators of radical types which are produced thermally or by the action of actinic radiation. It is thus possible to polymerize or cross-link mixtures of monomers or prepolymers containing functions in which the modes of polymerization are different, for example monomers or prepolymers which polymerize by free radical reaction and monomers or prepolymers which polymerize by cationic polymerization. This possibility is particularly advantageous for providing interpenetrated networks having different physical properties from those which would be obtained by a mere mixture of polymers originating from corresponding monomers. The vinyl ethers are not or are very little active by radical initiation. It is therefore possible, in a reaction mixture containing a photoinitiator according to the invention, a free radical initiator, at least one monomer of vinyl ether type and at least one monomer comprising non-activated double bonds such as those of the allyl groups, to carry out a separate polymerization of each type of monomer. On the other hand, it is known that monomers which are deficient in electrons, such as esters or amides of fumaric acid, maleic acid, acrylic or methacrylic acid, itaconic acid, acrylonitrile, methacrylonitrile, maleimides and derivatives thereof, are formed in the presence of electron enriched vinyl ethers, charge transfer complexes which give alternating polymers 1:1 by free radical initiation. An initial excess of vinyl monomers with respect to this stoichiometry enables preservation of polymerizable functions by pure cationic initiation. Triggering of the activity of a mixture of free radical initiator and cationic initiator according to the invention may be carried out simultaneously for the two reactants in the case for example of isolation with actinic radiation of a wavelength in which the photoinitiators of the invention and the free radical initiators selected are active, for example $\lambda$=250 nm. By way of example of initiators, the following commercial products may be mentioned: Irgacure 184®, Irgacure 651®, Irgacure 261®, Quantacure DMB®, Quarntacure ITX®.

It may also be advantageous to use the two types of polymerization in a sequential manner to form first prepolymers which are easy to produce and in which hardening, adhesiveness, solubility as well as cross-linking degree may be modified by initiating the activity of the cationic initiator. For example, a mixture of a thermo-dissociable free radical initiator and a cationic photoinitiator according to the invention enables to provide sequential polymerization and cross-linkings, first under the action of heat, then under the action of actinic radiation. In a similar manner, if a free radical initiator and a cationic photoinitiator according to the invention are selected, the first being photosensitive to longer wavelengths than the ones which initiate the photoinitiator according to the invention, there is obtained a cross-linking in two controllable steps. Free radical initiators may for example be Irgacure 651®, enabling initiation free radical polymerizations at wavelengths of 365 nm.

It is also an object of the invention to use ionic compounds of the invention for reactions of chemical amplification of photoresists for microlithography. During such a use, a film of a material comprising a polymer and an ionic compound of the invention is subject to irradiation. The irradiation causes the formation of the acid by replacement of the cation M with a proton, which catalyzes the decomposition or transformation of the polymer. After decomposition or transformation of the polymer on the parts of the film which have been irradiated, the formed monomers or the polymer which has been converted are eliminated and what remains is an image of the non-exposed parts. For this particular application, it is advantageous to use a compound of the invention which is in the form of a polymer consisting essentially of styrenyl recurring units having an ionic substituent $R_F$—$SO_x$—$N^-$—. These compounds enable to produce, after photolysis, products which are non-volatile, and therefore non-odorous when dealing with sulfides. Among the polymers which may thus be modified in the presence of a compound of the invention, there may be mentioned for example polymers containing ester groups or tertioalkyl arylether groups, for example poly (phthaldehydes), polymers of bisphenol A and a diacid, polytertiobutoxycarbonyl oxy-styrene, polytertiobutoxy-a-methyl styrene, polyditertiobutyifiimarate-co-allyltrimethylsilane and polyacrylates of a tertiary alcohol, in particular tertiobutyl polyacrylate. Other polymers are described in J. V. Crivello et al, Chemistry of Materials 8, 376–381, (1996).

The ionic compounds of the present invention, which have a high thermal stability, have numerous advantages with respect to the known salts of the prior art. They have initiation and propagation speeds which are comparable or higher than those obtained by means of coordination anions of the type $PF_6^-$, $AsF_6^-$ and especially $SbF_6^-$. In addition, the coefficient of diffusion of the anion $R_F$—$SO_x$—$N^-$— is higher than the one of hexafluorometallate anions or tetrafluoroborate anions or phenylborate anions. These properties are explained by the delocalization of the negative charge and the flexibility of the anion around the bond S—N.

In the compounds of the present invention, the pairs of ions have a very high dissociation, which enables the expression of the intrinsic catalyst properties of the cation $M^{m+}$, in which the active orbits are easily exposed to the substrates of the reaction, especially in various media. Most of the important reactions of organic chemistry may thus be carried out under easy conditions, with excellent yields, and facilitate the separation of the catalyst from the reaction mixture. The appearance of asymmetric induction by the use of an ionic compound according to the invention which carries a chiral group is particularly important because of its generality and its ease of application. It should be noted that the chiral perfluorinated molecules $[R_FSO_2$—$N$—$SO_2R_F]^-$, $1/mM^{m+}$ are unknown and would only present a negligible optical activity because of the low polarizable character of the perfluorinated groups. Consequently, it is another object of the present invention to use compounds of the invention as catalysts in Friedel and Craft reactions, Diels and Alder reactions, aldolization reactions, additions of Michael, allylation reactions, reactions of pinacolic coupling, reactions of glycosilation, reactions of openings of oxetane cycles, reactions of methathesis of alcenes, polymerization of the Ziegler-Natta type, polymerizations of the type methathesis by opening of the cycle and polymerizations of the type methathesis of acyclic dienes. The preferred ionic compounds of the invention for use as catalyst in the reactions mentioned above are those in which the cation is selected from lithium, magnesium, copper, zinc, tin, trivalent metals, including rare earths, platinoids, their organometallic couples, in particular metallocenes.

The compounds of the invention may also be used as a solvent for carrying out chemical, photochemical, electrochemical, photoelectrochemical reactions. For this particular use, ionic compounds in which the cation is an imidazolium, a triazolium, a pydridinium or a 4-dimethylamino-pyridinium are preferred, said cation optionally carrying a substituent on the carbon atoms of the cycle. The compounds being used in liquid form, those which have a melting point lower than 150° C., more particularly lower than 100° C. are particularly preferred.

The inventors have also found that the anionic charge carried by the group $R_F$—$SO_x$—$N^-Z$ exerts a stabilizing effect on electronic conductors of the conjugated polymer type, and that the use of a compound in which the substituent Z comprises a long alkyl chain would cause these polymers to be soluble in the usual organic solvents, even in doped state. Grafting of these charges on the polymer itself gives polymers in which the global charge is cationic, which are soluble in organic solvents and provide, in addition to their stability, properties of anti-corrosiveness towards metals, such as aluminum and ferrous metals. It is also an object of the present invention to provide electronically-conductive materials comprising an ionic compound of the present invention in which the cationic part is a polycation consisting of a "p" doped conjugated polymer. The preferred ionic compounds for this application are those in which the substituent Z contains at least one alkyl chain having from 6 to 20 carbon atoms. By way of example, the compounds in which Z is $R_D Y$—, $R_D$ being an alkyl radical, may be mentioned. There may also be mentioned compounds in which $R_F$ is $R_A CF_2$—, $R_A CF_2 CF_2$—, $R_A CF_2 CF(CF_3)$— or $CF_3 C(R_A)F$— in which $R_A$— represents an alkyl radical. Additionally, compounds in which Z represents an aromatic nucleus carrying an alkyl radical may also be mentioned.

Coloring materials of cationic type (cyanines) are used more and more frequently as sensitizers of photographic films, for the optical storing of information (optical disks which are accessible in writing), for lasers. The tendency of these conjugated molecules to be stacked over one another when they are in solid phases limits their use, because of the variations of the optical properties with respect to the isolated molecule. The use of ionic compounds of the invention for the manufacture of cationic coloring materials in which the counter ions, eventually fixed to this same molecule, correspond to the functions of the invention, enables to reduce the phenomenons of aggregation, including in solid polymer matrices, and to stabilize these coloring materials. It is another object of the invention to provide a composition of colouring material, characterized in that it contains an ionic compound according to the invention. The particularly preferred ionic compounds of this application are those in which the negative charge(s) of the ionic group $R_F$—$SO_x$—$N^-$—Z are either fixed to the molecule of the colouring material, or they constitute the counter-ion of the positive charges of the colouring material. By way of example of such compounds, the following compounds may be mentioned:

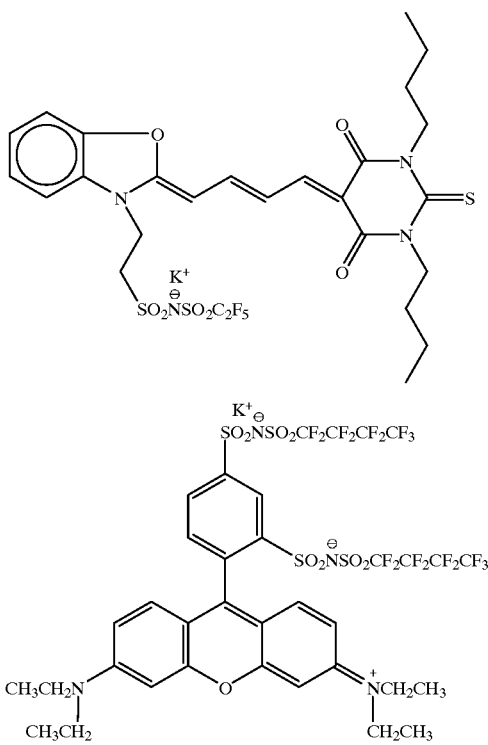

The present invention is illustrated by the following examples, however, it is not limited thereto.

Examples 1 to 7 describe the preparation of some compounds used as reactants for the synthesis of the ionic compounds of the present invention. Examples 8 to 78 illustrate the preparation of compounds according to the invention and their uses.

EXAMPLE 1

Trifluoromethanesulfonamide

To a suspension under strong stirring of 140.53 g (1.8 moles) of ammonium carbamate $H_2NCO_2NH_4$ (commercially available from Aldrich) in 11 of dichloromethane at 0° C., there is added drop-wise during 2 hours 282.13 g (1 mole) of trifluoromethanesulfonic anhydride $(CF_3SO_2)_2O$ (commercially available from Aldrich) diluted in 250 ml of dichloromethane. Carbon dioxide evolved according to the following reaction:

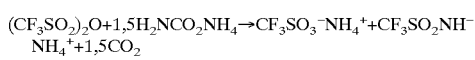

After 3 hours at 0° C., the reaction is continued for 24 hours at room temperature, and dichloromethane was evaporated and the product was reclaimed with 400 ml of water. The addition of 250 ml of a solution of hydrochloric acid 4 M has permitted release of trifluoromethanesulfonamide $CF_3SO_2NH_2$ which was extracted with three fractions of 200 ml of ether. After drying the ether phase (600 ml) with magnesium sulfate, the product was recovered after evaporation of ether and purified by sublimation under secondary vacuum at 60° C. There is obtained 137.16 g of trifluoromethanesulfonamide $CF_3SO_2NH_2$ (92% yield) having a purifity characterized by a proton and fluorine RMN higher than 99%.

The corresponding sodium salt was prepared by reacting trifluoromethanesulfonamide with sodium carbonate Na$_2$CO$_3$ in water (20% in excess). After evaporation of water and drying, the product obtained was reclaimed in acetonitrile and the excess of carbonate was removed by filtration. After evaporation of acetonitrile and drying, there is obtained a quantative amount of sodium salt of trifluoromethanesulfonamide CF$_3$SO$_2$NHNa.

Microanalysis has given: H, 0.52; (0.59); C, 7.22; (7.02); N, 8.41 (8.19); F, 33.82; (33.32); Na, 13.21; (13.44); S, 18.65 (18.74).

The lithium salt CF$_3$SO$_2$NHLi and potassium salt CF$_3$SO$_2$NHK have been obtained by a similar process, by replacing sodium carbonate respectively with lithium carbonate and potassium carbonate.

EXAMPLE 2

Fluorosulfonamide

The compound was prepared under similar conditions to those described in Example 1, by replacing the trifluoromethanesulfonamide CF$_3$SO$_2$NH$_2$ by 182.11 g (1 mole) of fluorosulfonic anhydride (FSO$_2$)$_2$O (commercially available from SST Corporation) previously purified by vacuum distillation. There is obtained 80.25 g of fluorosulfonamide FSO$_2$NH$_2$ (81% yield), having a purity characterized by a proton and fluorine RMN higher than 99%. The corresponding sodium salt was prepared by dosing an aqueous solution at 0° C. of fluorosulfonamide FSO$_2$NH$_2$ with a titrated solution of sodium hydroxide until reaching the neutralization point determined by pH-metry. After lyophilization and drying under vacuum during 24 hours, the sodium salt of fluorosulfonamide FSO$_2$NHNa was recovered quantitatively.

Microanalysis has given: H, 0.78; (0.83); N, 11.32; (11.57); F, 15.12; (15.69); Na, 18.66; (18.99); S, 26.01; (26.48).

The salts of lithium FSO$_2$NHLi and of potassium FSO$_2$NHK have been obtained by a similar process, by replacing sodium hydroxide respectively by lithium hydroxide and potassium hydroxide.

EXAMPLE 3

Pentafluoroethanesulfonyl chloride

In 600 ml of ether cooled to −78° C. under argon, 60 g (244 mmoles) of pentafluoroethyl iodine C$_2$F$_5$I (commercially available from Strem Chemicals) were condensed. Under stirring, there is then added 153 ml of a solution 1.6 M of methyllithium in ether (244 mmoles), (commercially available from Fluka). After 5 minutes, there was introduced ≈20 g (≈312 mmoles) of sulfur dioxide SO$_2$ into the solution, the reaction was continued during 2 hours at −78° C. Then, the solution was allowed to reach room temperature during 2 hours, and after 1 hour at room temperature, the solvents were evaporated. After drying, 44.51 g of lithium pentafluoroethanesulfinate C$_2$F$_5$SO$_2$Li (96% yield) were recovered.

A flow of chlorine Cl$_2$ was then allowed to pass in 200 ml of water containing 28.5 g (150 mmoles) of lithium pentafluoroethanesulfinate C$_2$F$_5$SO$_2$Li. Rapidly, there appeared a second phase, denser than water which was extracted with fractions of 25 ml of anhydrous dichloromethane. After drying the organic phase with magnesium sulfate, 26.55 g of pentafluoroethanesulfonyl chloride C$_2$F$_5$SO$_2$Cl (81% yield) were recovered by fractionate distillation. The product has a purity characterized by a fluorine RMN fluorine higher than 99%.

EXAMPLE 4

Perfluorobutanesulfonamide

To 30.21 g (100 mmoles) of perfluoro-1-butanesulfonyl fluoride C$_4$F$_9$SO$_2$F (commercially available from Aldrich) and 8.91 g (100 mmoles) of ethyl carbamate C$_2$H$_5$O$_2$CNH$_2$ in 100 ml of anhydrous tetrahydrofurane at 0° C., there is added in portions 1.75 g (220 mmoles) of 95% lithium hydride LiH at 95% (commercially available from Aldrich). After stirring for 72 hours under argon, the reaction mixture was centrifuged and filtered to remove the precipitate of lithium fluoride LiF and the excess of lithium hydride. The solvent was thereafter evaporated and the product obtained was reclaimed in 100 ml of water. After adding 3.5 g (200 mmoles) of lithium hydroxide monohydrate, the reaction mixture was heated to a reflux overnight to hydrolyze the ester function. After cooling, the reaction mixture was given a pH ≈1 by addition of a solution of hydrochloric acid 10 M in order to remove the carboxyl function which is present, and it was extracted with three fractions of 50 ml of ether after 24 hours of stirring. After drying of the organic phase with magnesium sulfate and evaporation, 27.2 g of perfluoro-1-butanesulfonamide C$_4$F$_9$SO$_2$NH$_2$ (91% yield) having a purity characterized by a proton and fluorine RMN higher than 99%, were recovered after drying under vacuum.

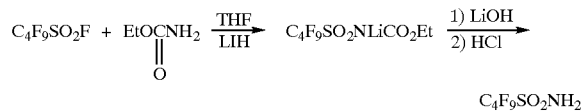

The corresponding sodium salt was prepared by reacting perfluoro-1-butanesulfonamide with sodium carbonate Na$_2$CO$_3$ in water (20% in excess). After evaporating water and drying, the product obtained was reclaimed in tetrahydrofurane and the excess of carbonate was removed by filtration. After evaporation of tetrahydrofiirane and drying, the sodium salt of perfluoro-1-butanesulfonamide C$_4$F$_9$SO$_2$NHNa was obtained quantitatively.

Microanalysis has given: H, 0.25; (0.31); C, 15.35; (14.96); N, 4.63; (4.36); F, 54.1; (53.25); Na, 7.36; (7.16); S, 10.35; (9.98).

The lithium and potassium salts were obtained by a similar process, by replacing lithium carbonate respectively with sodium carbonate and potassium carbonate.

EXAMPLE 5

Pentafluoroethanesulfonamide 10.93 g of pentafluoroethanesulfonyl chloride C$_2$F$_5$SO$_2$Cl, prepared as in Example 3, were added slowly to 50 ml of a 1 M solution of sodium bis(trimethylsilyl)amide ((CH$_3$)$_3$Si)$_2$NNa in tetrahydrofurane (50 mmoles, commercially available from Aldrich) at −20° C.

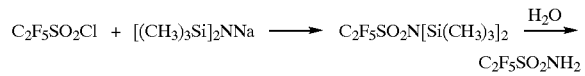

After 2 hours at −20° C., the solvent was evaporated and the product was reclaimed in 50 ml of water, the pH was brought to ≈2 and the aqueous phase was extracted with two fractions of 20 ml of ether. After drying the organic phase with magnesium sulfate, the recovered product was sublimated under vacuum. After 24 hours, 6.17 g of pentafluoroethanesulfonamide $C_2F_5SO_2NH_2$ (62% yield) having a purity characterized by a proton and fluorine RMN higher than 99% were recovered on a cold finger.

The corresponding sodium salt was prepared by reacting perfluoroethanesulfonamide with sodium carbonate $Na_2CO_3$ in water (20% in excess). After evaporating water and drying, the product obtained was reclaimed in tetrahydrofurane and the excess of carbonate was removed by filtration. After evaporating tetrahydrofurane and drying, the sodium salt of perfluoroethanesulfonamide $C_2F_5SO_2NHNa$ was obtained quantitatively.

Microanalysis has given: H, 0.42; (0.46); C, 10.35; (10.87); N, 6.73; (6.34); F, 42.01; (42.97); Na, 10.89; (10.4); S, 14.25; (14.5).

Salts of lithium and potassium were obtained by a similar process, by replacing sodium carbonate respectively with lithium and potassium carbonate.

EXAMPLE 6

Potassium Triflinate

To a suspension in 50 ml of anyhydrous acetonitrile at −18° C. of 22.64 g (100 mmoles) of the bi-potassium salt of 2,2-dimercapto-1,3,4-thiadiazole (commercially available from Aldrich), there is added 17.36 g (103 mmoles) of trifluoromethanesulfonyl chloride $CF_3SO_2Cl$. After 48 hours while stirring at room temperature, the reaction mixture was filtered to remove potassium chloride and the poly(2,2-dimercapto-1,3,4-thia-diazole) formed during the reaction according to the following reaction scheme:

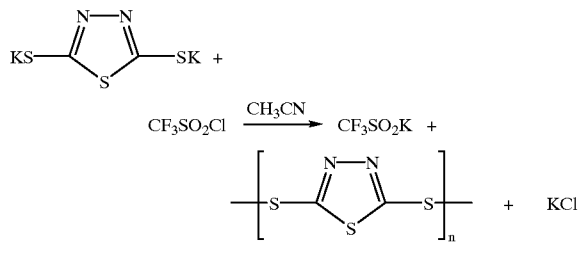

After evaporating the solvent and drying under vacuum at room temperature during 24 hours, 16.3 g of potassium triflinate $CF_3SO_2K$ (95% yield) were recovered with a purity characterized by a fluorine RMN higher than 98%.

Microanalysis has given: C, 6.72; (6.98); F, 32.6; (33.11); S, 18.32; (18.62); K, 22.29; (22.71).

EXAMPLE 7

3-sulfonyl-1,2,4-triazine chloride 28.83 (300 mmoles) of 3-amino-1,2,4,-triazine (commercially available from Aldrich) were added to a mixture under stirring of 100 ml of concentrated hydrochloric acid and 30 ml of glacial acetic acid. The reaction mixture was brought to −10° C. and 22.42 g (325 mmoles) of sodium nitrite $NaNO_2$ in 35 ml of water were added slowly. The diazotation reaction was allowed to proceed for 1 hour. At the same time, a flow of sulfur dioxide $SO_2$ was passed through a frit in 300 ml glacial acetic acid until saturation. Following this, 7.5 g of copper chloride (I) CuCl were added and the addition of suiffir dioxide was continued until the colour of the reaction mixture went from yellow-green to blue-green. After having brought the temperature of the reaction mixture to lower than 10° C., the previously prepared diazonium was added during 30 min. A small amount of ether was added to decrease the quantity of foam which is formed after each addition. After the end of diazonium addition, the reaction mixture was poured into 1 liter of a mixture of water and ice (1:1). After melting of the ice, a yellow oil was separated in a decanting flask, and the aqueous phase was extracted with two fractions of 100 ml ether. After adding the ether phase to the oil which has been collected, the solution was washed with a concentrated solution of sodium bicarbonate until reaching neutrality, and then with water, and fmally it was dried with magnesium sulfate. After evaporation of the solvent, 35.1 g of 3-sulfonyl-1,2,4-triazine (65% yield) having a purity characterized by proton and fluorine RMN higher than 98% were collected after vacuum distillation.

Microanalysis has given: C, 20.6; (20,1); H, 0.6; (1.1); N, 23.6; (23.4); S, 17.6; (17.9); Cl, 19.3; (19.7).

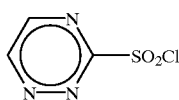

EXAMPLE 8

3-chloropropanesulfonyl(trifluoromethanesulfonyl)-imide 17.7 g (100 mmoles) of 3-chloropropanesulfonyl chloride $Cl(CH_2)_3SO_2Cl$ and 37.44 g (200 mmoles) of potassium trifluoromethanesulfonamide $CF_3SO_2NHK$ were reacted at 0° C. in 50 ml of tetrahydrofurane anhydride. After 3 hours at 0° C., and 24 hours at room temperature, tetrahydrofurane was evaporated and the product was crystallized in 40 ml of water, recovered by filtration and dried. There were obtained 23.6 g of the potassium salt of trirluoromethanesulfonyl(3-chloropropanesulfonyl)-imide $Cl(CH_2)_3SO_2NKSO_2CF_3$ (72% yield) having a purity characterized by proton and fluorine RMN higher than 99%.

Microanalysis has given: H, 1.76; (1.85); C, 14.23; (14.66); N, 4.56; (4.27); F, 17.78; (17.39); S, 19.09; (19.56); Cl, 10.28; (10.82); K, 11.45; (11.93).

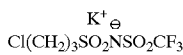

By a similar process, the potassium salt of fluorosulfonyl (3-chloropropane-sulfonyl)imide (65% yield) was obtained from the potassium salt of fluorosulfonamide obtained in Example 2 and the potassium salt of pentafluroethane-sulfonyl(3-chloropropanesulfonyl)imide (82% yield) was obtained from the potassium salt of pentafluorosulfonamide obtained in Example 5.

Lithium salts were obtained in quantitative yields by treatment of the potassium salts in anhydrous tetrahydrofurane with a stoichiometric quantity of anhydrous lithium chloride, filtration of the reaction medium, evaporation of the solvent and drying under vacuum.

These three salts are soluble in most of the usual organic solvents (tetrahydrofurane, acetonitrile, dimethylformamide, ethyl acetate, glymes, . . . ) and in aprotic solvating polymers such as poly (ethylene oxide). In this latter solvent at a concentration O/K of 14/1, they have an ionic conductivity greater than $10^{-3}$ S.cm$^{-1}$ at a temperature of 100° C.

These salts may be easily grafted on different substrates including a site which is sufficiently nucleophilic such as an alcoholate, an amide or a methylide.

EXAMPLE 9

2,2,2-trifluoroethanesulfonyl (trifluoromethanesulfonyl)imide

To a solution in 30 ml of anhydrous acetonitrile at 0° C. of 9.13 g (50 mmoles) of 2,2,2-trifluoroethanesulfonyl CF$_3$CH$_2$SO$_2$Cl (commercially available from Aldrich) and 7.45 g (50 mmoles) of trifluoromethanesulfonamide CF$_3$SO$_2$NH$_2$, 7.91 g (100 mmoles) of anhydrous pyridine were added drop-wise. After 2 hours at 0° C., the reaction was continued during 48 hours at room temperature. The reaction mixture was then filtered to remove the pyridinium hydrochloride formed. The reaction mixture was then stirred during 48 hours with 5.79 g (50 mmoles) of lithium phosphate Li$_3$PO$_4$. After filtration, evaporation of the solvent and drying, 14.6 g of the lithium salt of trifluoromethanesulfonyl (2,2,2-trifluoroethane-sulfonyl) imide CF$_3$CH$_2$SO$_2$NLiSO$_2$CF$_3$ (97% yield) were obtained.

Microanalysis has given: H, 0.72; (0.67); Li, 2.48; (2.3); C, 11.56; (11.97); N, 4.88, (4.65); F, 38.02; (37.86); S, 21.56; (21.3).

This salt has a conductivity of $2.3 \times 10^{-4}$ S.cm$^{-1}$ at 60° C. in poly (ethylene oxide) at a concentration of O/Li of 12/1.

It has a proton presenting an acid character enabling to give reactions of nucleophilic substitution in the presence of a base with, for example, alkyl or acid halides.

EXAMPLE 10

N-methyl-sulfonyl(trifluoromethanesulfonyl)imide

Under argon, there is added drop-wise during 2 hours 100 ml of a 2M is solution of methylamine CH$_3$NH$_2$ (200 mmoles), (commercially available from Aldrich) in tetrahydrofurane to a solution, at −20° C. under strong stiffing, of 13.5 g (100 mmoles) of sulfiryl chloride SO$_2$Cl$_2$ in 50 ml of anhydrous dichloromethane. After 3 hours at −20° C., the reaction mixture was subjected to centrifugation to remove the precipitate of methylammonium hydrochloride CH$_3$NH$_3{}^+$Cl$^-$ formed. After evaporation of tetrahydrofurane, the remaining liquid was distilled under vacuum. There are obtained 12.82 g of N-methyl-chlorosulfonamide ClSO$_2$NH(CH$_3$) (95% yield) having a purity characterized by a proton RMN higher than 98%.

6.48 g (50 nmuoles) of N-methyl-chlorosulfonamide were then reacted in 30 ml of anhydrous tetrahydrofurane with 7.45 g (50 mmoles) of trifluoromethanesulfonamide, and with 11.22 g (100 mmoles) of 1,4-diazabicyclo[2.2.2]octane (DABCO). After 48 hours, the reaction mixture was filtered to remove the DABCO hydrochloride precipitate formed. After evaporation of the solvent, the product obtained was reclaimed in 20 ml of ethanol and 40.91 g (100 mmoles) of potassium acetate were added. The precipitate was then formed. After recrystallization, filtration and drying, 9.95 g of potassium trifluoromethanesulfonyl(N-methylsulfonyl) imide CF$_3$SO$_2$NKSO$_2$NH(CH$_3$) (71% yield) were recovered, in which the purity characterized by proton and fluorine RMN is higher than 98%.

Microanalysis has given: H, 1.31; (1.44); C, 8.38; (8.57); N, 9.85; (9.99); F, 20.89; (20.34); S, 22.35; (22.88); K, 13.52; (13.95).

By a similar process, the potassium salt of trifluoromethanesulfonyl(N-ethyl-sulfonyl)imide was obtained from ethylamine and the potassium salt of trifluoromethanesulfonyl(N-propyl-sulfonyl)inde was obtained from propylamine.

The lithium salts were prepared quantitatively by ionic exchange between the potassium salts and lithium chloride in anhydrous tetrahydrofurane.

These compounds have a labile proton permitting to give reactions of nucleophilic substitution in the presence of a base with alkyl and acid halides for example.

EXAMPLE 11

5-formyl-2-furanesulfonyl(trifluoromethanesulfonyl) imide

To 9.91 g (50 mmoles) of the sodium salt of 5-formyl-2-furanesulfonic acid (commercially available from Aldrich) in 30 ml of anhydrous dimethylformamide at 0° C., 6.35 g (50 mmoles) of oxalyl chloride ClCOCOCl in solution in 20 ml of anhydrous dichloromethane were added slowly, then, after 2 hours at 0° C., 18.72 g (100 mmoles) of the potassium salt of trifluoromethanesulfonamide CF$_3$SO$_2$NHK were added. This reaction was continued for 48 hours at room temperature, and the solvent was evaporated and the product obtained was crystallized in 40 ml of water. After filtration and drying, 10.88 g of the potassium salt of trifluoromethanesulfonyl(5-formyl-2-furane-sulfonyl)imide (63% yield) having a purity determined by fluorine and proton RMN higher than 99% were recovered.

Microanalysis has given: H, 1.01; (0.88); C, 20.55; (20.87); N, 4.15; (4.06); F, 16.91; (16.51); S, 18.17; (18.57); K, 11.76; (11.32).

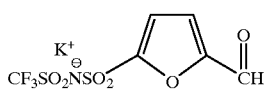

By the same process, the potassium salt of fluorosulfonyl (5-formyl-2-furane-sulfonyl)imide was obtained.

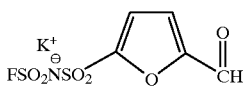

The aldehyde function enables grafting of this salt on substrates containing a group capable of reacting with this function, for example, an amino group or a double bond.

EXAMPLE 12

Allylsulfonyl(trifluoromethanesulfonyl)imide

To 14.41 g (100 mmoles) of the sodium salt of 2-propene-sulfonic $CH_2=CHCH_2SO_3Na$ in suspension in 60 ml of anhydrous acetonitrile at $-20°$ C., 11.9 g (100 mmoles) of thionyl chloride $SOCl_2$ diluted in 20 ml of benzene were added drop-wise during 2 hours. The mixture was allowed to stand overnight at $-20°$ C., and it was centrifuged to remove sodium chloride formed and the solvents were evaporated by means of a rotary evaporator provided with a membrane pump. The liquid obtained was then distilled under vacuum in a short column to give 10.97 g of 2-propene-sulfonyl $CH_2=CHCH_2SO_2Cl$ (78% yield) characterized by a proton RMN. 7.03 g (50 mmoles) of this compound were then reacted with 18.72 g (100 mmoles) of potassium trifluoro-methanesulfonamide $CF_3SO_2NHK$ in 60 ml of an anhydrous acetonitrile at $0°$ C. during 2 hours, followed by a reaction period at room temperature for 24 hours. After evaporation of the solvent, the product was recrystallized in 20 ml of water. After filtration and drying, 17.22 g of the potassium salt of trifluoromethane-sulfonyl(2-propenesulfonyl)imide $CH_2=CHCH_2SO_2NKSO_2CF_3$ (66% yield) having a purity characterized by a proton and fluorine RMN higher than 98%.

Microanalysis has given: H, 1.68; (1.73); C, 16.22; (16.49); N, 4.6; (4.81); F, 19.12; (19.57); S, 22.29; (22.01); K, 13.23; (13.42).

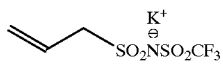

According to the same process, the potassium salt of pentafluoroethanesulfonyl(2-propene-sulfonyl)imide (69% yield) was obtained from the potassium salt of pentafluoro-ethanesulfonamide obtained in Example 5.

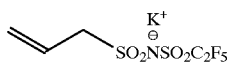

These salts have the characteristic of homo-or copoly-merizing by a polymerization which is initiated by free radical polymerization or by means of an olefin polymer-ization catalyst of the Ziegler-Natta type, such as a zircanocene, and more generally, they are characterized by being able to undergo chemical reactions inherent to ethyl-enic bonds.

EXAMPLE 13

3,4-epoxypropane-1-sulfonyl (trifluoromethanesulfonyl)imide

To 11.65 g (40 mmoles) of the potassium salt of trifluoromethanesulfonyl(2-propenesulfonyl)imide, obtained in Example 12, in 100 ml of water, there were added 6.9 g (40 mmoles) of 3-chloroperoxybenzoic acid obtained according to the procedure described by Schwartz & Blumbergs (J. Org. Chem., (1964), 1976). After 1 hour of strong stirring, the solvent was evaporated and the residue was recrystallized in 15 ml ethanol. After filtration and drying, 7.5 g of the potassium salt of 2,3-epoxy-propane-1-sulfonyl(trifluoromethane-sulfonyl)imide (61% yield) having a purity characterized by proton and fluorine RMN higher than 98% were recovered.

Microanalysis has given: H, 1.84; (1.64); C, 15.2; (15.63); N, 4.99; (4.56); F, 18.01; (18.55); S, 20.15; (20.87); K, 12.01; (12.72).

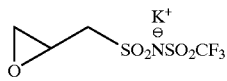

According to the same procedure, there is obtained the potassium salt of a 2,3-epoxypropane-1-sulfonyl (pentafluoroethanesulfonyl)imide from the potassium salt of pentafluoroethanesulfonyl(2-propene-sulfonyl)imide obtained in Example 12.

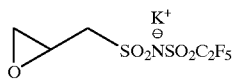

Lithium salts were obtained by treating potassium salts in anhydrous tetrahydrofurane with the stoichiometric quantity of anhydrous lithium chloride, filtration of the reaction mixture, evaporation of the solvent and drying under vacuum.

These salts may be homo- or copolymerized by means of a polymerization initiated by anionic or cationic means. More generally, they may undergo chemical reactions which are inherent to oxetanes.

The homopolymer of 2,3-epoxypropane-1-sulfonyl (trirluoromethane-sulfonyl)imide was prepared by polymer-ization in tetrahydrofurane which was initiated by anionic polymerization with potassium tert-butoxide, then the poly-salt of lithium was prepared by ionic exchange with anhy-drous lithium chloride. The latter has a conductivity in a gelled medium (21% by weight of polyacrylonitrile, 38% ethylene carbonate, 33% propylene carbonate, 8% homopolymer) of $1.1 \times 10^{-3}$ S.cm$^{-1}$ at $30°$ C. The cationic transport number of this electrolyte is 0.82. Moreover, this homopolymer is soluble in most of the usual organic sol-vents (tetrahydrofurane, acetonitrile, dimethylformamide, ethyl acetate, glymes, . . . ) and in aprotic solvating poly-mers.

EXAMPLE 14

Vinylsulfonyl(trifluoromethanesulfonyl)imide

To a solution at $0°$ C. and under argon of 8.15 g (50 mmoles) of 2-chloro-1-ethane-sulfonyl chloride $ClCH_2CH_2SO_2Cl$ (commercially available from Aldrich) and 7.45 g (50 mmoles) of trifluoromethanesulfonamide $CF_3SO_2NH_2$ in 25 ml of anhydrous tetrahydrofurane, there is added drop-wise during 30 min, a solution of 16.83 g (150 mmoles) of DABCO diluted in 25 ml of anhydrous tetrahy-drofurane. After the end of the addition of the base, the reaction is continued during 2 hours at $0°$ C., and then for 24 hours at room temperature. The reaction mixture was then filtered to remove the DABCO hydrochloride formed. Then, 2.12 g of anhydrous lithium chloride (50 mmoles) were added, the reaction mixture was stirred during 24 hours, and it is again filtered to remove the DABCO hydrochloride formed. After evaporation of tetrahydrofurane and drying, 11.89 g of the lithium salt of trifluoromethanesulfonyl (vinylsulfonyl)imide $CH_2=CHSO_2NLiSO_2CF_3$ (98% yield) were recovered having a purity which is characterized by a proton and fluorine RMN higher than 98%.

Microanalysis has given: H, 1,.28; (1.23); Li, 2.78; (2.83); C, 14.91; (14.7); N, 5.82; (5.71); F, 22.5; (23.25); S, 25.8; (26.16).

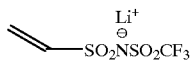

According to the same process, the lithium salt of perfluorobutanesulfonyl)vinyl-sulfonyl)imide (99% yield) was obtained from the perfluorobutanesulfonamide obtained in Example 4.

These salts may be homo- or copolymerized by a polymerization which is initiated by free radical polymerization. More generally, they may undergo chemical reactions which are inherent to activated vinyl bonds, in particular additions of Michael, with for example an alcoholate.

EXAMPLE 15

7,8-octene-3,6-oxa-1-sulfonyl(trifluoromethane-sulfonyl)imide

To 2.2 g (25 mmoles) of ethylene glycol vinyl ether $CH_2=CHO(CH_2)_2OH$ in 60 ml of anhydrous dimethylfonnamide, there is added 6.13 g (25 mmoles) of the lithium salt of vinylsulfonyl-(trifluoromethanesulfonyl) imide, obtained in Example 14, 5.87 g of anhydrous potassium carbonate $K_2CO_3$ (42.5 mmoles) and 330 mg (1.25 mmoles) of a crown ether, 18-Crown-6 (acting as complexing agent of the potassium cation). The reaction mixture was then stirred under argon at 85° C. After 48 hours, the reaction mixture was filtered on a fitted glass of porosity No. 3, and the solvent was evaporated under reduced pressure. After drying, the compound was recrystallized in 10 ml of water containing 1.86 g (25 mmoles) of anhydrous potassium chloride KCl. After filtration and drying, 5.66 g of the potassium salt of 7,8-octene-3,6-oxa-1-sulfonyl (trifluoromethane-sulfonyl)imide (62% yield) having a purity characterized by a proton and fluorine RMN higher than 98% was recovered.

Microanalysis has given: H, 3.12; (3.03); C, 23.26; (23.01); N, 3.77; (3.83); F, 15.89; (15.6); S, 17.12; (17.55); K, 10.23; (10.7).

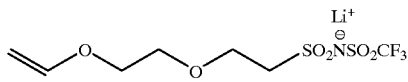

There is obtained a quantitative yield of the lithium salt by treatment of the potassium salt in anhydrous tetrahydrofurane with the stoichiometric quantity of anhydrous lithium chloride, filtration of the reaction mixture, evaporation of the solvent and drying under vacuum.

This salt may be homopolymerized by cationic polymerization. It may also be copolymerized by cationic polymerization, optionally by polymerization which is alternated with an unsaturated monomer. More generally, it may undergo chemical reactions which are characteristic of alkyl vinyl ethers.

The homopolymer prepared by polymerization in anhydrous acetonitrile initiated by cationic polymerization with bis(trifluoromethanesulfonyl)imide has a conductivity at a concentration of 0.8 M in a mixture of dirnethylcarbonate and ethylene carbonate (2:1) of $6\times10^{-3}$ S.cm$^{-1}$ at 30° C. Moreover, this homopolymer is soluble in most of the known organic solvents (tetrahydrofurane, acetonitrile, dimethylformamide, ethyl acetate, glymes, . . . ) and in the aprotic solvating polymers such as poly (ethylene oxide).

EXAMPLE 16

4-styrenesulfonyl(trifluoromethanesulfonyl)imide

In 100 ml of anhydrous tetrahydrofurane under argon at 0° C., 20.27 g (10 mmoles) of 4-styrenesulfonyl chloride $CH_2=CHC_6H_4SO_2Cl$ (commercially available from Monomer-Polymer & Dajac Laboratories) were reacted with 14.91 g (10 mmoles) of trifluoromethane-sulfonamide $CF_3SO_2NH_2$ and 22.44 g (20 mmoles) of (DABCO). After 2 hours at 0° C. and 48 hours at room temperature, the solution was filtered to remove the DABCO hydrochloride formed, and it was thereafter treated with 424 mg (10 mmoles) of anhydrous lithium chloride, which is stored and weighed in a glove box. Immediately, a precipitate of DABCO hydrochloride was formed and the reaction mixture was then again filtered after stirring for 6 hours. After evaporation and drying under vacuum, during 24 hours at room temperature, 31.16 g of the lithium salt of trifluoromethane-sulfonyl(4-styrenesulfonyl)imide were recovered which have a purity characterized by a proton and fluorine RMN higher than 97%.

Microanalysis has given: H, 2.4; (2.2); Li, 2.56; (2.16); C, 33.15; (33.65); N, 4.79; (4.36); F, 17.14; (17.74); S, 19.51; (19.96).

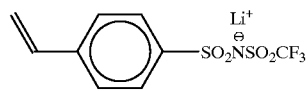

According to the same process, lithium salts of fluorosulfonyl(4-styrenesulfonyl)-imide (98% yield) were prepared from the fluorosulfonamide obtained in Example 2, of pentafluoroethanesulfonyl(4-styrenesulfonyl)imide (97% yield) from the pentafluoroethanesulfonamide obtained in Example 5 and of perfluorobutanesulfonyl(4-styrenesulfonyl)imide (99% yield) from the perfluorobutanesulfonamide obtained in Example 4.

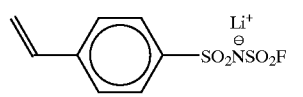

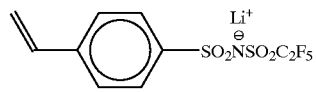

-continued

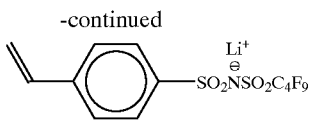

These salts may be homo- or copolymerized by polymerization initiated by anionic, cationic and more particularly free radical means. They may also be grafted on a polymer matrix such as vinylidene polyfluoride by irradiation.

The homopolymers obtained by free radical polymerization in deaerated water, initiated by cyanovaleric acid at 60° C. are soluble in the usual organic solvents and in aprotic solvating polymers. In poly(ethylene oxide) at a concentration O/Li of 16/1, these salts have a conductivity ≈6×10$^{-4}$ S.cm$^{-1}$ at 100° C. Moreover, in a concentrated solution in acetone (≈1 M as lithium cation), these homopolymers may be used as catalysts in Diels-Alder reactions, and in this way they act as chemical micro-reactors.

EXAMPLE 17

5-(4-methylene-1,3-dioxolane)-2-furanesulfonyl (trifluoromethanesulfonyl)imide 5.18 g (15 mmoles) of the potassium salt of trifluoromethanesulfonyl(5-formyl-2-furanesulfonyl)imide, 1.66 g (15 mmoles) of 3-chloro-1,2-propanediol ClCH$_2$CH(OH)CH$_2$(OH) (commercially available from Aldrich) and ≈1 mg of p-toluenesulfonic acid monohydrate were mixed in 30 ml of toluene. An azeotropic distillation was then carried out until the appearance of water in the Dean-Stark ceased to be observed. After evaporation of the solvent, the product obtained was recrystallized in 10 ml of water. After filtration and drying, 5.13 g of the potassium salt of 5-(4-methylene-1,3-dioxolane)-2-furanesulfonyl(trifluoromethane-sulfonyl)imide (82% yield) were recovered, and this product had a purity determined by proton and fluorine RMN higher than 98%.

Microanalysis has given: C, 26.65; (26.93); H, 1.89; (1.76); N, 3.99; (3,.49); S, 15.28; (15.98); F, 13.8; (14.2); K, 9.41; (9.74).

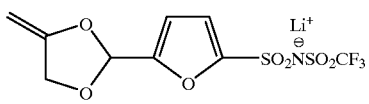

A quantitative yield of the lithium salts was obtained by treatment of the potassium salt in anhydrous tetrahydrofurane with a stoichiometric quantity of anhydrous lithium chloride, filtration of the reaction mixture, evaporation of the solvent and drying under vacuum.

This salt may be homo- or copolymerized by a polymerization initiated by cationic or free radical means. The homopolymer of this salt was obtained by photopolymerization, which is initiated by cationic means through irradiation of tris(4-methylphenyl)sulfonium hexafluoroantimonate with a U.V. lamp during 10 min at 36° C. It has a conductivity at a concentration of 0.5 M in tetraethylsulfamide (C$_2$H$_5$)$_2$NSO$_2$N(C$_2$H$_5$) of 4×10$^{-3}$ S.cm$^{-1}$ at 20° C.

EXAMPLE 18

1-acryloyl-2,2,2-trifluoroethanesulfonyl-(trifluoro-methanesulfonyl)imide

By operating in a glove box under argon, 7.53 g (25 mmoles) of the lithium salt of trifluoromethanesulfonyl(2,2,2-trifluoro-ethanesulfonyl)imide CF$_3$CH$_2$SO$_2$NLiSO$_2$CF$_3$, prepared as in Example 9, were solubilized in 15 ml of anhydrous tetrahydrofurane. After adjusting the temperature of this solution to −20° C., 50 ml of a 1 M solution (25 mmoles) in tetrahydrofurane of sodium bis(trimethylsilyl)amide ((CH$_3$)$_3$Si)$_2$NNa (commercially available from Aldrich) were added. After 15 min, there is slowly added 2.26 g (25 mmoles) of acryloyl chloride CH$_2$=CHCOCl previously purified by distillation under vacuum; The reaction was continued during 2 hours at −20° C., and the reaction mixture was filtered to remove the precipitate of sodium chloride. The solvent was then evaporated and there is obtained after drying under vacuum at room temperature 8.7 g (98% yield) of the lithium salt of trifluoromethanesulfonyl(1-acryloyl-2,2,2-trifluoroethanesulfonyl)imide CH$_2$=CHCOCH(CF$_3$)SO$_2$NLiSO$_2$CF$_3$ having a purity characterized by a proton and fluorine RMN higher than 98%.

Microanalysis has given: H,1.26; (1.14); Li, 1.69; (1.95); C, 20.06; (20.29); N, 3.79; (3,.94); F, 32.33; (32.1); S, 18.26; (18.05).

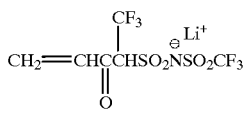

This salt may be homo- or copolymerized by photopolymerization in the presence of a photo-sensitizer.

There is prepared a mixture containing this salt (16 weight %), a poly(ethylene glycol) dimethacrylate having a molar weight of 600 g/mole (81 weight % commercially available from Aldrich), particles of silica having a specific surface of 300 m$^2$/g (3 weight %, Aerosil, commercially available from Degussa AG) and xanthone. This solution was deposited with a reel on a glass plate covered with a layer of tungsten trioxide WO$_3$ and a conductive sub-layer of tin oxide. There is obtained a membrane which is optically transparent in the visible range and which adheres on the support by photopolymerization initiated by irradiation by means of U.V. lamp during 10 min at 32° C. Then, an electrochrome system was prepared by assembling in a glove box a counter-electrode consisting of the deposit on a glass plate of a layer of hydrogenated iridium oxide H$_x$IrO$_2$ and a sublayer of tin oxide. This electrochrome has given a variation of the optical absorption from 80% (discoloured state) to 30% (coloured state) and good performances in cycling. is thus possible to produce a number of cycles of coloring/discoloring greater than 20,000.

EXAMPLE 19

3-maleimidopropanesulfonyl(trifluoromethane-sulfonyl)imide

To a solution of 2.43 g of maleimide (25 mmoles) in 20 ml of anhydrous tetrahydrofurane there were added by portions 215 mg of lithium hydride LiH (27 mmoles). After 1 hour, a potassium salt of trifluoromethanesulfonyl(3-chloropropane-sulfonyl)imide prepared as in Example 8 was added to the filtered solution. The reaction was continued during 24 hours at 60° C., and the reaction mixture was filtered to remove the potassium chloride KCl precipitate, the solvent was evaporated and the product was dried. There is thus obtained 8.37 g (94% yield) of the lithium salt of trifluoromethanesulfonyl(3-maleimido-propanesulfonyl)imide (—COCH=CHCO—)N(CH$_2$)$_3$SO$_2$NLiSO$_2$CF$_3$ having a purity characterized by a proton and fluorine RMN≈96%.

Microanalysis has given: H 2.15 (2.26); Li 2.15 (1.95); C 26.72 (26.97); N 7.66 (7.86); F 16.54 (16); S 18.25 (18).

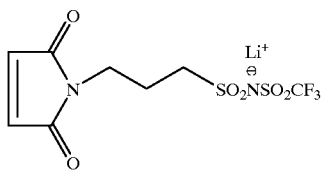

According to the same process, the lithium salt of pentafluoroethanesulfonyl(3-maleimido-propanesulfonyl) imide (98% yield) was obtained from the potassium salt of pentafluoroethane-sulfonyl(3-chloropropanesulfonyl)imide obtained in Example 8.

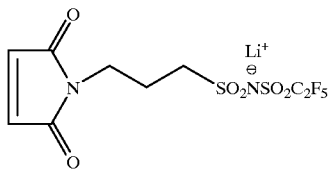

These salts may be homopolymerized by free radical or anionic polymerization or can be copolymerized by anionic or free radical polymerization optionally by polymerization alternated with an electron donor monomer (N-vinyl-2-pyrrolidone, N-vinyl formamide, vinyl ether, . . . ).

The homopolymer prepared by polymerization in anhydrous tetrahydrofurane at −78° C., initiated by anionic polymerization with sec-butyllithium, is soluble in the usual organic solvents (tetrahydrofurane, acetonitrile, dimethylformamide, ethyl acetate, glymes, . . . ) and in aprotic solvating polymers such as poly (ethylene oxide).

EXAMPLE 20

2-(triethoxysilyl)ethanesulfonyl(trifluoromethane-sulfonyl)imide

In a Parr chemical reactor, there is introduced a solution of 9.36 g (50 mmoles) of the potassium salt of trifluoromethanesulfonamide $CF_3SO_2NHK$ and 264 mg of a potassium cation complexing crown ether, 18-Crown-6, in 60 ml of anhydrous acetonitrile. After closing the reactor, flushing with argon was carried Gout during 15 min before isolating it. There were then introduced 6.41 g (50 mmoles) of sulfur dioxide $SO_2$ (commercially available from Fluka) and, after 10 min, 9.52 g (50 mmoles) of vinyltriethoxysilane (commercially available from Fluka) in solution in 20 ml of anhydrous acetonitrile. After 6 hours at room temperature, the temperature of the reactor was raised to 40° C. and was kept at that temperature during 48 hours, and the solvent was evaporated. After drying under vacuum, the product was stored under argon. A quantitative yield of the potassium salt of trifluoromehanesulfonyl(2-triethoxysilyl)ethane-sulfonyl)imide having a purity characterized by a fluorine and proton RMN higher than 99% was recovered.

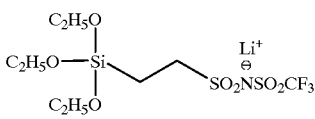

Microanalysis has given: H 4.79 (4.34); K 8.27 (8.85); C 24.99 (24.48); N 3.89 (3.17); F 12.15 (12.91); Si 6.75 (6.36); S 14.33 (14.52).

The lithium salt was obtained by ionic exchange with lithium chloride in tetrahydrofurane.

The corresponding acid was obtained by co-crushing in an agate mortar, under a glove box, the potassium salt with three equivalents (150 mmoles) of anhydrous ammonium hydrogen sulfate $HSO_4NH_4$ (commercially available from Aldrich). Then, by secondary sublimation under vacuum at 40° C., trifluoromethanesulfonyl(2-(triethoxy-silyl) ethanesulfonyl)imide was recovered after 24 hours on a cold finger at a temperature of −40° C.

These salts enable formation of organosilicon networks by a mechanism of hydrolysis-polycondensation. They also permits seeding of glass base materials (fibre, glazing, . . . ) in order to modify their surface.

In addition, homopolymers or copolymers may be obtained with various alkoxysilanes in a protic medium, optionally in the presence of a catalyst (acid, base, fluoride, . . . ).

A copolymer was prepared by polycondensation of the potassium salt of trifluoromethanesulfonyl-(2-triethoxysilyl)ethanesulfonyl)imide with O-[20(trimethoxysilyl)ethyl]-O'-methylpolyethylene glycol of molecular weight 5,000 (commercially available from Shearwaters Polymers) (5:1 molar) in a water/methanol mixture by using as catalyst trifluoromethanesulfonyl(2-(triethoxysilyl)ethane-sulfonyl)imide. After a few hours, the solution was concentrated. Then, a pad of activated charcoal, previously de-gassed, having a specific surface of 1,500 $m^2/g$ (commercially available from Actitex), was impregnated with the viscous liquid obtained. After drying, this operation was repeated to improve the impregnation. After having maintained the impregnated pad during 1 week in a dryer at 50° C., two buttons having a diameter of 2 cm were cut out by stamping. A sheet of cigarette paper (commercially available from Bolioré Technologies) was then impregnated with a viscous liquid identical to the one used to impregnate the carbon pad. This sheet was placed between the two in buttons of impregnated carbon pad which were used as carbon electrodes. After 1 week in a dryer at 50° C., and 2 days under vacuum at 60° C., there is obtained a "all-solid" electrochemical supercapacitance. This supercapacitance has given the following performances at 40° C.: a density of energy of 15 Wh/l (or a capacity of 96 F/g of carbon for an electrode), a maximum power of 700 W/kg and good results in cycling (more than 10,000 cycles of charge/discharge between 0 and 2V). Such a supercapacitance is particularly interesting in the field of electronics because of the absence of volatile liquids.

A solution of the potassium salt of trifluoromethanesulfonyl-(2-(triethoxysilyl)ethanesulfonyl) imide with O-[2-(triethoxysilyl)ethyl]-O'-methyl-polyethylene glycol having a molecular weight of 5,000 (commercially available from Shearwaters Polymers) (3:1 molar) was prepared in a mixture of water/methanol. A glass plate pickled with nitric acid and dried at 100° C. was thereafter soaked in the solution for a few minutes. After rinsing with methanol and drying, a surface conductivity of $3 \times 10^{-5}$ S (square) was measured which is sufficient to give antistatic properties to the surface of the glass.

EXAMPLE 21 bis[3-(trimethoxysilyl)propyl]aminosulfonyl (trifluoro-methanesulfonyl)imide 5.96 g (40 mmoles) of trifluoromethane-sulfonamide $CF_3SO_2NH_2$ and 8.97 g (40 mmoles) of DABCO in 60 ml of anhydrous dichloromethane were cooled at $-30°$ C. 5.4 g (40 mmoles) of sulfuryl chloride $SO_2Cl_2$ and 12.54 g (40 mmoles) of bis[3-(trimethoxysilyl)propyl]amine of formula $[(CH_3O)_3Si(CH_2)_3]_2NH$ were then added drop-wise. The mixture was stirred during 4 hours at $-30°$ C., and for 24 hours at room temperature. 1.7 g of anhydrous lithium chloride LiCl were then added, the reaction mixture was stirred during 24 hours, and filtered to removed the precipitate of DABCO hydrochloride. After evaporation of the solvent and drying under vacuum, 21.88 g (98% yield) of the lithium salt of bis[3-(trimethoxysilyl)propyl]aminosulfonyl (trifluoro-methanesulfonyl) having a purity characterized by a fluorine and proton RMN higher than 98% were recovered.

Microanalysis has given: H, 5.32; (5.41); Li, 1.56; (1.24); C, 27,.66; (27.95); N, 5.22; (5.01); F, 10.56; (10.2); Si, 10.26; (10.06); S, 11.67; (11.48).

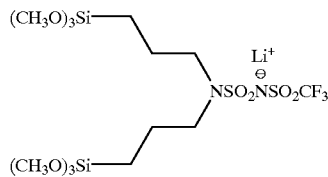

This compound has properties analogous to those of the compound of Example 20 and may be used for the same applications.

This compound was polycondensed in a water/methanol mixture, utilizing a drop of concentrated hydrochloric acid as catalyst. After a few hours, the solvents were evaporated and the viscous liquid obtained was poured on a Teflon® plate. After one week in a dryer at 50° C., the material obtained was dried under vacuum at 100° C. during 48 hours, and crushed under argon until obtaining a particle size of the order of 1 micron. A composite electrolyte was then prepared by mixing this powder with poly (ethylene oxide) of molecular weight $M_w 32\ 3.10^5$ in acetonitrile. After having poured this dispersion in a glass ring and having evaporated the acetonitrile, there is obtained a film of composite electrolyte having a good mechanical behaviour, a thickness of 220 μm. This electrolyte has an ionic conductivity greater than $10^{-5}\ S^1.cm^{-1}$ at 60° C. The cationic transport number is 0.92.

EXAMPLE 22

N-methyl-N-vinylester-sulfonyl(trifluoromethane-sulfonyl)imide

To 7.01 g (25 mmoles) of the potassium salt of trifluoromethanesulfonyl(N-methylsulfonyl)imide $CF_3SO_2NKSO_2NH(CH_3)$, prepared as in Example 10, in solution in 15 ml of anhydrous tetrahydrofurane, there was slowly added under argon 25 ml of a 1 M solution in tetrahydrofurane of potassium tert-butoxide $(CH_3)_3COK$ (25 mmoles, commercially available from Aldrich). After a few minutes, 2.66 g (25 mmoles) of vinylchloroformate $CH_2=CHO_2CCl$ (commercially available from Lancaster), previously distilled under vacuum, were added. The reaction is continued during 24 hours at room temperature. The reaction mixture was then filtered to remove the precipitate of potassium chloride, the solvent was evaporated and the product was dried under vacuum. There is obtained 8.58 g (98% yield) of the potassium salt of triuoromethanesulfonyl-(-methyl-N-vinylester-sulfonyl)imide $CF_3SO_2NKSO_2N$ $(CH_3)CO_2CH=CH_2$.

Microanalysis has given: H, 1.56; (1.73); C, 17.56; (17.14); N, 8.37; (8); F, 17.01; (16.27); S, 18.56; (18.3); K, 11.46; (11.16).

The lithium salt was obtained with quantitative yield by treating the potassium salt in anhydrous tetrahydrofurane with the stoichiometric quantity of anhydrous lithium chloride, filtration of the reaction mixture, evaporation of the solvent and drying under vacuum.

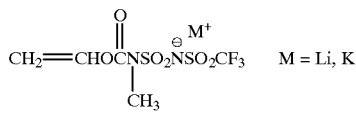

This salt may be homo- or copolymerized by means of a polymerization initiated by free radical.

There is produced a film of polymer electrolyte, having a thickness of 30 μm, consisting of the lithium salt in solution in a poly (ethylene oxide) matrix having ethylenic unsaturations, at a concentration O/Li=26/1, and containing 1% by weight of cyanovaleric acid and 3% by weight of silica having a specific surface of 300 m²/g (Aerosil, commercially available from Degussa AG). This polymer was obtained by polycondensation of polyethylene glycol of a molecular weight 1,000 with 3-chloro-2-chloromethyl-1-propene according to the procedure described by Alloin & al. (J. Power Sources, (1995), 26, 34–39). On the other hand, on a sheet of aluminum, a composite electrode having a thickness of 90 μm containing 45% by volume of vanadium dioxide ($V_2O_5$), 5% by volume of Kejenblack® K600 (commercially available from Akzo) as an additive of electronic conduction, and 50% by volume of a polymer electrolyte of the same composition as the one described above, was prepared. In a glove box under argon, the film of polymer electrolyte was then deposited on the composite electrode, the film being covered with a film of lithium with a thickness of 30 μm, deposited on a sheet of aluminum. The temperature of the assembly was then adjusted to 60° C. during 24 hours by applying a slight pressure. There is thus obtained an electrochemical generator with fixed anions, the lithium salt co-cross-linking with the double bonds of the polymer matrix. This generator gave a satisfactory result during cycling at 70° C. (72% of the capacity after 10 cycles at the 500th cycle of charge/discharge). Performances during calls for power were also improved.

EXAMPLE 23

4-perfluorovinyloxyphenylsulfonyl (pentafluorosulfonyl)imide

Under argon, at 9.95 g (50 mmoles) of pentafluoroethanesulfonamide $C_2F_5SO_2NH_2$ in solution in 40 ml of anhydrous tetrahydrofurane at $-20°$ C., 10 ml of a 10 M solution of butyllithium in hexane $C_4H_9Li$ (100 mmoles) were slowly added. After 2 hours, 14.63 g of (3-(1,1,2,2- tetrafluoroethoxy)benzene sulfonyl chloride (50 mmoles), prepared from (3-(1,1,2,2-tetrafluoroethoxy)aniline according to the general process described in Example 7, were added. The reaction was continued during 24 hours at −20° C., and 50 ml of a 10 M solution of butyllithium in hexane $C_4H_9Li$ (50 mmoles) were added. After 2 hours, the temperature was allowed to rise to ambient and the solvents were evaporated. The product was reclaimed in 30 ml of ethanol and recrystallized after addition of 4.91 g (50 mmoles) of potassium acetate $CH_3COOK$. After filtration and drying, 17.25 g of the potassium salt of pentafluoroethanesulfonyl(3-(1,1,2-tri-fluorovinyloxy) benzenesulfonyl)imide (78% yield) having a purity characterized by a proton and fluorine higher than 98% were obtained.

Microanalysis has given: H, 1.1; (0.85); C, 25.62; (25.37); N, 2.69; (2.96); F, 33.1; (32.11); S, 13.16; (13.55); K, 8.95; (8.26).

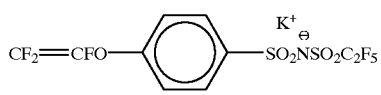

According to the same process, the potassium salt of trifluoromethane-sulfonyl(3-(1,1,2-trifluorovinyloxy) benzenesulfonyl)imide (98% yield) was obtained from trifluoromethanesulfonamide.

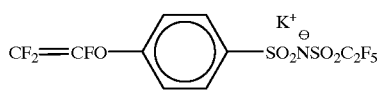

The corresponding acids were obtained by ether extraction of acidified aqueous solutions of various potassium salts. Lithium salts were obtained by treating different acids with lithium carbonate $Li_2CO_3$.

These salts may be homo- or copolymerized by free radical initiated polymerization.

A porous textile made from GORE-TEX® with a thickness of 100 μm, commercialized by Gore, was impregnated with a concentrated solution of trifluoromethane-sulfonyl(3-(1,1,2-trifluorovinyloxy)-benzene-sulfonyl)imide oxide in dichloromethane containing cyanovaleric acid as polymerization initiator. After evaporation of the solvent, the acid was homopolymerized within the textile matrix by increasing the temperature of the product under argon to 60° C. during 24 hours. The membrane thus obtained was used as electrolyte in a test cell of a polymer electrolyte battery with combustible hydrogen/oxygen. The life span obtained with this membrane was longer than 1,000 hours, with good power performances. This membrane may also be used for the Friedel-Crafts heterogeneous catalysis of the acylation reaction of toluene with benzoyl chloride.

EXAMPLE 24

2,2-fluorovinylsulfonyl(trifluoromethane-sulfonyl) imide

Under argon, to a solution of 6.02 g (20 mmoles) of the lithium salt of trifluoromethane-sulfonyl(2,2,2-trifluoroethanesulfonyl)imide obtained in Example 9, in 40 ml of anhydrous tetrahydrofurane at −20° C., there was slowly added 10 ml of a 2 M solution of butyllithium in cyclohexane $C_4H_9Li$ (20 mmoles, commercially available from Aldrich). After 2 hours at −20° C., the reaction mixture was centrifuged to remove the precipitate of lithium fluoride which has appeared during the reaction. After evaporation of the solvents and drying, the lithium salt of 2,2-fluorovinylsulfonyl(trifluoro-methanesulfonyl)imide having a purity determined by a proton and fluorine RMN higher than 99% was recovered with quantitative yield.

Microanalysis has given: H, 0.47; (0.36); Li, 2.71; (2.47); C, 12.51; (12.82); N, 4.72; (4.98); F, 33.54; (33.79); S, 22.65; (22.81).

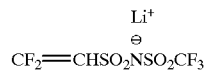

This salt may be homo- or copolymerized by a free radical initiated polymerization.

The homopolymer prepared by polymerization in anhydrous tetrahydrofurane at 66° C., initiated by free radical with 1,1'-azobis(cyclohexane-carbonitrile), is soluble in the usual organic solvents (tetrahydrofurane, acetonitrile, dimethylformamide, ethyl acetate, glymes, . . . ) and in aprotic solvating polymers such as poly (ethylene oxide). In an aqueous solution at 25° C., it has a conductivity of $9.3 \times 10^{-3}$ S.cm$^{-1}$ at a concentration of 0.5 M. It gives antistatic properties to coatings containing same.

EXAMPLE 25

Dimethylaminosulfonyl(trifluoromethanesulfonyl) imide

To a solution at 0° C. and under argon of 14.36 g (100 mmales) of sulfamoyl chloride $(CH_3)_2NSO_2Cl$ (commercially available from Aldrich) and 14.91 g of trifluoromethanesulfonamide $CF_3SO_2NH_2$ (100 mmoles) in 60 ml of anhydrous tetrahydrofurane, there is added 22.44 g (200 mmoles) of DABCO in solution in 20 ml of anhydrous tetrahydrofurane at 0° C. After 2 hours at 0° C., the reaction was continued during 24 hours at room temperature. The precipitate of DABCO hydrochloride was removed by filtering on a fitted glass of porosity No. 4. Then, there is added 4.24 g (100 mmoles) of anhydrous lithium chloride, the reaction mixture was stirred during 24 hours, and it was again filtered to remove the DABCO hydrochloride formed. After evaporation of tetrahydroflirane and drying, 25.17 g (96% yield) of the lithium salt of trifluoromethanesulfonyl-(dimethylaminosulfonyl)imide $Me_2NSO_2NLiSO_2CF_3$ having a purity characterized by a fluorine and proton RMN higher than 99% was recovered.

Microanalysis has given: H, 2.34; (2.31); Li, 2.52; (2.65); C, 13.96; (13.65); N, 10,.75; (10.69); F, 21,.25; (21.74); S, 24.35; (24.46).

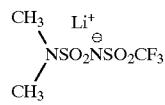

According to the same process, the lithium salt of pentafluoroethanesulfonyl(dimethyl-aminosulfonyl)imide (98% yield) was prepared from the pentafluoroethanesulfonamide obtained in Example 5.

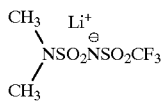

These salts have an excellent solubility in the usual organic solvents (tetrahydrofurane, acetonitrile, dimethylformamide, ethyl acetate, glymes, . . . ) and in aprotic solvating polymers such as poly (ethylene oxide). In this latter solvent, at a concentration O/Li=12/1, the lithium salt of trifluoromethanesulfonyl(dimethylaminosulfonyl)imide has a anionic conductivity of $1.2 \times 10^{-4}$ S.cm$^{-1}$ at 60° C. The concentrated solutions of the salts in acetone may be utilized as catalyst for Diels-Alder reactions.

A lithium-polymer generator was produced by utilizing a metallic lithium anode, an electrolyte made of a terpolymer of ethylene oxide, allylglycidylether and methylglycidylether containing the lithium salt of trifluoromethanesulfonyl(dimethylaminosulfonyl)imide at a concentration O/Li=20/1, and a composite cathode based on vanadium oxide (40% by volume), carbon black (5% by volume) and an electrolyte identical to the one described above (50% by volume). This generator has given a cycling profile at 60° C. which is equivalent to the one obtained by utilizing one of the more currently known salts for this application, lithium bis(trifluoromethanesulfonyl)imide (LiTFSI).

EXAMPLE 26

Dimethylaminosulfonyl(trifluoromethanesulfonyl)imide

To a solution kept at 0° C. and under argon containing 14.36 g (100 mmoles) of sulfamoyl chloride (CH$_3$)$_2$NSO$_2$Cl (commercially available from Aldrich) and 14.91 g of trifluoromethanesulfonamide CF$_3$SO$_2$NH$_2$ (100 mmoles) in 60 ml of anhydrous tetrahydrofurane, there is added 22.44 g (200 mmoles) of DABCO in solution in 20 ml of anhydrous tetrahydrofurane at 0° C. After 2 hours at 0° C., the reaction was continued during 24 hours at room temperature. The precipitate of DABCO hydrochloride was removed by filtration on a flitted glass of porosity No. 4. After evaporation of tetrahydrofirane and drying, the product was solubilized in 25 ml of ethanol. There is then added 9.81 g (100 mmoles) of potassium acetate CH$_3$COOK, then the precipitate obtained with ethanol reflux was recrystallized. After cooling, filtration and drying, 24.13 g (82% yield) of the potassium salt of trifluoromethanesulfonyl-(dimethylaminosulfonyl)imide Me$_2$NSO$_2$NKSO$_2$CF$_3$ having a purity characterized by a fluorine and proton RMN higher than 99% were recovered.

Microanalysis has given: H, 2.21; (2.05); C, 12.56; (12.24); N, 9.78; (9.52); F, 19.89; (19.37); S, 21.56; (21.79); K, 13.11; (13.28).

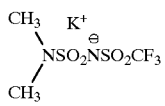

By the same process, the potassium salt of perfluorobutanesulfonyl(dimethyl-aminosulfonyl)imide (85% yield) was obtained from perfluorobutanesulfonamide obtained in Example 4.

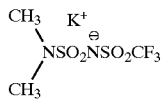

The potassium salt of trifluoromethanesulfonyl)-dimethylaminosulfonyl)imide has a melting point of 188° C. It has a conductivity in poly (ethylene oxide) at a concentration O/K=12/1 at 60° C. of $5.10^{-4}$ S.cm$^{-1}$.

The conductivity of a mixture of the potassium salt and the lithium, salt obtained in Example 25, in a ratio K/Li=2/1 and for a total concentration in alkaline cation O/(Li+K)= 14/1 in poly (ethylene oxide) was also determined. This conductivity is identical to the one determined for the potassium salt alone, which indicates a mechanism of vehicular transport of lithium in the complex electrolyte by the anions which thus travel in the form of an anionic complex, which has little interaction with the basic solvent. This type of conductivity is very favourable to the operation of lithium generators and more particularly polymer electrolyte generators, since performances during calls for power are improved.

EXAMPLE 27

Dimethylaminosulfonyl(trifluoromethanesulfonyl)imide of 2,2'-azobis (2-methylpropionamidine)

5.89 g (20 mmoles) of the potassium salt of trifluoromethanesulfonyl(dimethylaminosulfonyl)imide Me$_2$NSO$_2$NKSO$_2$CF$_3$, prepared according to Example 26, were placed in solution in 10 ml of water. Under stirring, 2.71 g of 2,2'-azobis(2-methylpropionamidine) hydrochloride [=NC(CH$_3$)$_2$C(=NH)NH$_2$]$_2$.2 HCl (10 mmoles, commercially available from Aldrich) in solution in 10 ml of water were added. There is immediately formed a precipitate which was collected by filtration. After drying under vacuum at room temperature, 4.36 (96% yield) of 2,2'-azobis (2-methylpropionamidine) dimethylaminosulfonyl (trifluoromethanesulfonyl)imide [=NC(CH$_3$)$_2$C(=NH)NH$_2$]$_2$.2 Me$_2$NSO$_2$NHSO$_2$CF$_3$ were recovered.

This salt is a free radical polymerization initiator which is soluble in most usual organic solvents (tetrahydroflirane, acetonitrile, dimethylformamide, ethyl acetate, glymes, . . . ) and in aprotic solvating polymers, contrary to 2,2'-azobis (2-methylpropionamidine) hydrochloride.

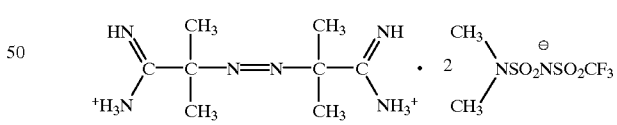

An acetonitrile solution of 1 part of this initiator and 100 parts of a polymer containing ethylenic unsaturations was prepared. This polymer was obtained by polycondensation of polyethylene glycol of molecular weight 1,000 with 3-chloro-2-chloromethyl-2-propene according to the procedure described by Alloin et al. (Solid States Ionics, (1993), 60, 3). The viscous solution obtained was poured on a polypropylene film (PP). After evaporation of the solvent, the polymer film of a thickness of 110 μm on PP was stored for one week in a glove box under argon for drying. Cross-linking was then initiated by raising the temperature of the film to 60° C. After 1 night, there is obtained a film having good mechanical properties and a low rate of substances that can be extracted (lower than 1%). The solubility of the initiator used in the polymer matrix therefore enables to give an efficient and homogeneous cross-linking. Moreover, this initiator is not volatile, contrary for example to 2,2'-azobisisobutyronitrile, and the quantity added may be optimized to the best for each type of polymerization.

EXAMPLE 28

Dialkylaminosulfonyl(trifluoromethanesulfonyl) imide 15.85 g (200 mmoles) of dibutylamine $(C_4H_9)_2NH$ in solution in 50 ml of anhydrous tetrahydrofurane were treated with 27.83 g (200 mmoles) of sulfur trioxide complexed with trimethylamine $(CH_3)_3NSO_3$. After stirring for 24 hours at room temperature, the solvent was evaporated and the product was reclaimed in 40 ml of methanol. After having added 19.63 g (200 mmoles) of potassium acetate $CH_3CO_2K$ and re-crystallizing the precipitate obtained, there is recovered after filtration and drying 32.66 g of the potassium salt of sulfonic acid of dibutylamine $(C_4H_9)_2NSO_3K$ (66% yield). To 12.37 g of this salt (50 mmoles) in 50 ml of tetrahydrofurane at 0° C., 6.35 g (50 mmoles) of oxalyl chloride ClCOCOCl, and after 2 hours at 0° C., 18.72 g (100 mmoles) of the potassium salt of trifluoromethane-sulfonamide $CF_3SO_2NHK$ were added slowly. The reaction was continued for 48 hours at room temperature, and the solvent was evaporated and the product obtained was recrystallized in 50 ml of water. After filtration and drying, 14.38 g of the potassium salt of trifluoromethanesulfonyl(dibutyl-aminosulfonyl)imide $(C_4H_9)_2NSO_2NKSO_2CF_3$ (76% yield) having a purity characterized by a proton and fluorine RMN higher than 99% were recovered.

Microanalysis has given: H, 4.65; (4.79); C, 28.23; (28.56); N, 7.1; (7.4); F, 15.52; (15.06); S, 16.45; (16.94); K, 10.52; (10.33).

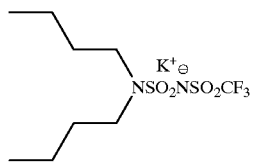

By a similar process, potassium salts of amides carrying a diethyl substituent $(C_2H_5)_2NSO_2NKSO_2CF_3$ (66% yield) were prepared from diethylamine, and amides carrying a di-2-ethylhexyl substituent $[C_4H_9—CH(C_2H_5)—CH_2]_2NSO_2NKSO_2CF_3$ (70% yield) was prepared from di-2-ethylhexylamine, with purities characterized by proton and fluorine RMN higher than 98%.

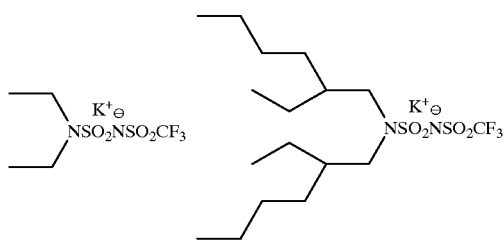

By a similar process, the different potassium salts of fluorosulfonyl-(dialkylaminosulfonyl)imides were prepared from the fluorosulfonamide obtained in Example 2, the potassium salts of pentafluoroethanesulfonyl(dialkyl-aminosulfonyl)imides were prepared from the pentafluoro-ethanesulfonamide obtained in Examiner 5 and potassium salts of perfluorobutanesulfonyl(dialkyl-aminosulfonyl) imides $(C_4H_9)_2NSO_2NKSO_2C_4F_9$ were prepared from the perfluorobutanesulfonamide obtained in Example 4.

By ionic exchange in acetone between the potassium salt of trifluoromethane-sulfonyl(di-2-ethylhexylaminosulfonyl) imide with an infrared coloring material of the cyanine family, 3,3'-diethylthiatricarbocyanine (commercially available from Aldrich) followed by re-precipitation in water, it was possible to obtain after filtration and drying the compound 3,3'-diethylthiatricarbo-cyanine of di-2-ethylhexylaminosulfonyl(trifluoro-methanesulfonyl)imide.

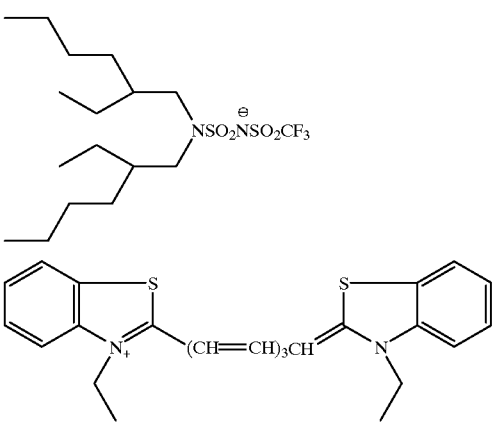

This salt is very soluble in low polar solvents such as dichloromethane or methylene chloride as well as in polymer matrices with low polarity such as methyl polymethacrylate.

It was also possible to note a very distinct decrease of the aggregation of cationic colouring materials between one another because of the "plasticizing" character of the groups di-2-ethylhexylamino, which is an advantage insofar as the phenomenon of aggregation brings a winding of the optical absorption bands which is prejudicial to the precision of the operation of systems utilizing these colouring materials, in particular optical disks for storing information.

EXAMPLE 29

Dimethylaminosulfonyl (trifluoromethanesulfonyl) imide imidazolium 14.71 g (50 mmoles) of the potassium salt of trifluoromethanesulfonyl(dimethylaminosulfonyl)imide $(CH_3)_2NSO_2NKSO_2CF_3$ prepared according to Example 26, were co-crushed in an agate mortar under a glove box with 17.27 g (150 mmoles) of ammonium hydrogenosulfate $HSO_4NH_4$ (commercially available from Aldrich). By sublimation under secondary vacuum at 80° C., there is recovered on a cold fmger after 24 hours 11.2 g (87% yield) of trifluoromethanesulfonyl(dimethylaminosulfonyl)imide $(CH_3)_2NSO_2NHSO_2CF_3$ having a purity characterized by a fluorine and proton RMN higher than 99%.

To a solution in 15 ml of ether containing 1.36 g of imidazole (20 mmoles), there is added 5.12 g of this acid (20 mmoles), and after 24 hours under stirring, a precipitate formed is recovered by filtration on a fitted glass of porosity No. 3. After drying, a quantitative amount of the imidazolium salt of trifluoromethanesulfonyl-(dimethylaminosulfonyl)imide was recovered.

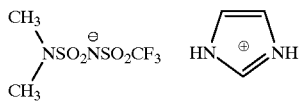

A crushing under a glove box of a molar mixture of 7 imidazoles for 2 imidazolium salts has enabled to give a compound having a melting temperature lower than ambient. This molten salt has an elevated protonic conductivity which is higher than $10^{-3}$ S.cm$^{-1}$ at 60° C. It is possible to obtain a polymer electrolyte, which is an anhydrous protonic conductor by adding poly (ethylene oxide), preferably of high molecular weight or which can later be cross-linked, to the molten salt without detrimentally affecting the conductivity. These polymer electrolytes are particularly interesting for the preparation of systems for the modulation of light such as electrochrome glass panes including electrochrome systems containing coloring materials.

There is obtained a membrane which is optically transparent in visible light and having a good mechanical behaviour by utilizing a polymer electrolyte made of 80% by weight of molten salt and 20% by weight of poly (ethylene oxide) of molecular weight $M_w=5.10^6$. There was then produced an electrochrome system under glove box by utilizing this electrolyte enclosed between a first electrode consisting of the deposit on a glass plate of a layer of hydrogenated iridium oxide $H_xIrO_2$ and a conductive sub-layer of tin oxide and a second electrode consisting of a layer of tungsten trioxide $H_xIrO_2$ and a conductive sub-layer of tin oxide. This electrochrome led to a variation of the optical absorption from 80% (discolored state) to 30% (colored state) and good performances in cycling (more than 20,000 cycles of coloring/discoloring).

An electrochrome was also produced by dissolving two complimentary coloring materials in such a molten salt: in a glove box, 1.62 g (5 mmoles) of the imidazolium salt of trifluoromethanesulfonyl(dimethylaminosulfonyl)imide and 1.02 g of imidazole (15 mmoles) were crushed together. Then, to the molten salt, there was added 16.5 mg (50 μmoles) of green leucomalachite (colorless reduced state) and 29.5 mg (50 μmoles) of the salt of 3-(4,5-dimethyl-thiazolyl-2-yl)-2,5-diphenyl-2H-tetrazolium (MTT) and trifluoromethanesulfonyl(dimethyl-aminosulfonyl)imide (colorless oxidized state, obtained by ionic exchange in water starting from the bromide.). Then, there was added 5% by weight of poly (ethylene oxide) of molecular weight $M_w=3.10^5$. The salt obtained was placed between 2 glass plates covered with a conductive layer of tin oxide ($SnO_2$). After pressing under vacuum to homogenize the deposit and sealing it to make it impervious, there is obtained a coloring material base electrochrome system. After having sealed the product obtained to make it impervious, a potential of 1,300 mV was applied on the outside by means of a potentiostat. The system then became colored, and the oxidized form of green malachite and the reduced form of MTT each has an intense absorption band in the visible range. By applying a potential of –500 mV, a relatively rapid discoloring of the system (lower than 60 s) was noted. Such an electrochrome system is easy to prepare, even for systems of large sizes (higher than m$^2$) which utilize glass or a suitably treated polymer as conductive transparent electrode. Moreover, the energy which is necessary to maintain coloration is relatively low, lower than 1 W/m$^2$.

EXAMPLE 30

Dimethylaminosulfonyl(trifluoromethanesulfonyl) imide

To 2.56 g of trifluoromethanesulfonyl(dimethyl-aminosulfonyl)imide $(CH_3)_2NSO_2NHSO_2CF_3$ (10 mmoles), obtained as in Example 29, in solution in 10 ml of water, there is added 763 mg (1.67 mmoles) of anhydrous lanthanum carbonate $La_2(CO_3)_2$. After stirring overnight, water was evaporated and the lanthanum salt of trifluoromethanesulfonyl(dimethylaminosulfonyl)-imide $[(CH_3)_2NSO_2NSO_2CF_3]_3La$ was recovered in quantitative yield after drying.

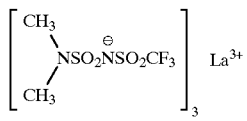

This salt is highly soluble in the usual organic solvents (tetrahydrofurane, acetonitrile, dimethylformamide, ethyl acetate, glymes, . . . ) It is also capable of interaction with solvents with low polarities such as dichloromethane, which interaction is better than that of the lanthanum salt of bis(trifluoromethane-sulfonyl)imide. It may be used as a catalyst in Diels-Alder reactions.

EXAMPLE 31

Dialkylaminosulfonyl(trifluoromethanesulfonyl) imide

To 3.78 g (10 mmoles) of the potassium salt of trifluoromethanesulfonyl(dimethylaminosulfonyl)imide $(CH_3)_2NSO_2NKSO_2CF_3$, obtained in Example 26, in solution in 10 ml of anhydrous nitromethane, there is added in a glove box, 1.17 g of nitrosonium tetra-fluoroborate $NOBF_4$ (10 mmoles, commercially available from Aldrich). After 1 hour, the reaction mixture was filtered to remove the insoluble potassium tetrafluoroborate, and there is thus obtained a solution 1 M of trifluoromethanesulfonyl-(dimethylaminosulfonyl)imide $(CH_3)_2NSO_2N(NO)SO_2CF_3$ in nitromethane.

By a similar process, a 1 M solution in nitromethane of the nitrosonium salt of trifluoromethanesulfonyl(dibutyl-aminosulfonyl)imide $(C_4H_9)C_2NSO_2N(NO)SO_2CF_3$, was prepared from the potassium salt of trifluoromethanesulfonyl-(dibutylaminosulfonyl)imide (obtained in Example 28) and another 1 M solution in nitromethane of the nitrosonium salt of trifluoromethane-sulfonyl(N,N-di-2-ethylhexylaminosulfonyl)imide $(C_4H_9CH(C_2H_5)CH_2)_2N(NO)SO_2CF_3$, was prepared from the potassium salt of trifluoromethanesulfonyl-(N,N-di-2-ethylhexylanlinosulfonyl)imide (obtained in Example 28).

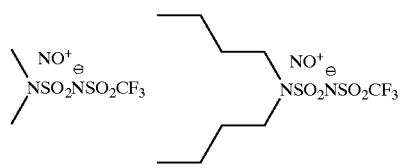

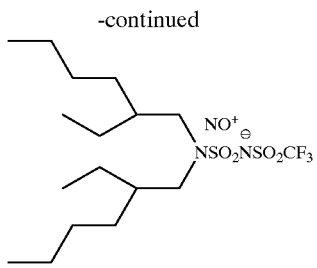

These salts are particularly interesting for doping conjugated polymers (polythiophene, polypyrrole, . . . ) to which they give a notable electronic conductivity.

Three deposits of stereoregular poly(3-hexyl-thiophene) (commercially available from Aldrich) were prepared on glass plates from a chloroform solution. After drying, these deposits were doped with one of the salts in solution in nitromethane. After doping, the three poly(3-hexylthiophene) films had an electronic conductivity higher than 1 S.cm$^{-1}$ independently of the doping salt. Stability in humid medium of the conductivity was improved with an increase of the length of the alkyl segments. These deposits are useful for preparing masks in the semi-conductor industry.

EXAMPLE 32

Dialkylaminosulfonyl(trifluoromethanesulfonyl) imide 5.96 g (40 mmoles) of trifluoromethane-sulfonamide $CF_3SO_2NH_2$ and 9.9 ml of pyridine in 60 ml of anhydrous dichloromethane were cooled at −20° C. 5.4 g (40 mmoles) of sulfuryl chloride $SO_2Cl_2$ diluted in 10 ml of anhydrous dichloromethane and 8.1 g (80 mmoles) of dipropylamine $(C_3H_7)_2NH$ were then added drop-wise. The mixture was stirred for 1 hour at −20° C. and during 24 hours at room temperature. The reaction mixture was then filtered, and the solvent was evaporated. The product which was recovered was reclaimed in 50 ml of water, acidified at a pH≈2 with a solution of hydrochloric acid 4 M, the aqueous phase was extracted twice with 20 ml of ether, the organic phase was dried with magnesium sulfate, and ether was evaporated. After sublimation of the compound obtained under secondary vacuum at 40° C., 10 g of trifluoromethanesulfonyl (dipropylaminosulfonyl)imide (80% yield) having a purity characterized by a fluorine and proton RMN higher than 98% were recovered.

The lithium salt was prepared by pH-metry dosing the acid in solution in water with a titrated solution of lithium hydroxide. After evaporating water and drying under vacuum at 60° C. during 24 hours, the lithium salt of trifluoromethanesulfonyl(dipropylaminosulfonyl)-imide $(C_3H_7)_2NSO_2NLiSO_2CF_3$ was recovered in quantitative yield in the form of a white powder.

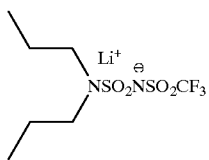

Microanalysis has given: H, 4.33; (4.43); Li, 2.01; (2.18); C, 26.59; (26.42); N, 8.69; (8.8); F, 17.33; (17.91); S, 20.46; (20.15).

According to the same process, the lithium salt of trifluoromethanesulfonyl(N-methyl-N-ethyl aminosulfonyl) imide $CH_3(C_2H_5)NSO_2NLiSO_2CF_3$ was prepared by the same process and it has a purity determined by a proton and fluorine RMN higher than 99% with a yield of 76%.

These salts are soluble in most of the usual organic solvents (tetrahydrofurane, acetonitrile, dimethylformamide, ethyl acetate, glymes, . . . ) and in aprotic solvating polymers such as poly (ethylene oxide).

The lithium salt of trifluoromethanesulfonyl-(dipropylaminosulfonyl)imide has a conductivity of 1.4× $10^{-4}$ S.cm$^{-1}$ in poly (ethylene oxide) at a concentration O/Li=12/1 and the cationic transport number is 0.42.

EXAMPLE 33

3-(trifluoromethyl)phenyl(trifluoromethane-sulfonyl) amide

To 48.34 g of 3-(trifluoromethyl)aniline (300 mmoles) in 250 ml of anhydrous dichloromethane at 0° C., there is added drop-wise during 2 hours, 28.21 g of trifluoromethanesulfonic anhydride $(CF_3SO_2)_2O$ (100 mmoles) diluted in 100 ml of anhydrous dichloromethane, and the reaction was continued during 24 hours at room temperature. After evaporation of dichloromethane, the product obtained was reclaimed in 300 ml of water, then acidified with 25 ml of a 4 M solution of hydrochloric acid. The aqueous solution was then extracted by means of three fractions of 50 ml of ether, the organic phases were combined and dried with magnesium sulfate. After evaporation of ether and drying, the product obtained was purified by sublimation under secondary vacuum at 40° C. After 24 hours, 25 g of trifluoromethanesulfonyl(3-(trifluoromethyl) phenyl)amide m-$CF_3C_6H_4NHSO_2CF_3$ (85% yield) were recovered on a cold finger in the form of a white solid crystalline product having a purity characterized by a fluorine and proton RMN higher than 99%.

Microanalysis has given: H, 1.65; (1.72); C, 32.53; (32.77); N, 4.62; (4.78); F, 38.12; (38.88); S, 10.72; (10.94).

The lithium salt was prepared by treating the acid obtained with lithium phosphate $Li_3PO_4$ during 48 hours in acetonitrile. After filtration of the reaction mixture, evaporation of the solvent and drying under vacuum at 60° C. during 24 hours, the lithium salt of trifluoromethanesulfonyl (3-(trifluoromethyl)phenyl) amide m-$CF_3C_6H_4NLiSO_2CF_3$ was obtained in quantitative yield.

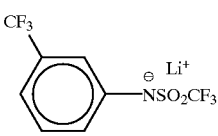

Sodium and potassium salts were obtained by a similar process, while replacing lithium phosphate respectively with sodium and potassium phosphate.

In the same manner, trifluoromethanesulfonyl(3-5-bis (trifluoromethyl)-phenyl)arnide (I) was prepared from 3-5-bis(trifluoro-methyl)aniline, trifluoromethanesulfonyl(4-trifluoromethoxy)phenyl)amide (II) was prepared from trifluoromethanesulfonyl(4-trifluoromethoxy)aniline, trifluoromethanesulfonyl(4-aminopyridine)amide (III) was prepared from 4-aminopyridine and trifluoromethanesulfonyl(2,2,2-trifluoroethyl)amide (IV) was prepared from 2,2,2-trifluoroethylamine, as well as corresponding lithium, sodium and potassium salts.

(I)

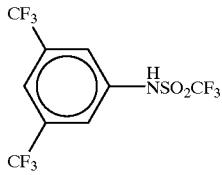

(II)

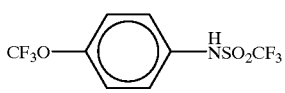

(III)

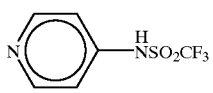

(IV)

For all these salts, derivatives of the type fluorosulfonyl were obtained by utilizing fluorosulfonic anhydride ($FSO_2$)$_2O$ (commercially available from SST Corporation) instead of trirluoromethanesulfonic anhydride.

These salts are soluble in most of the usual organic solvents (tetrahydrofurane, acetonitrile, dimethylformamide, ethyl acetate, glymes, . . . ) and in aprotic solvating polymers such as poly (ethylene oxide). They have an oxidation potential higher than 4 V towards a lithium anode. The salts of lithium or potassium, or mixtures thereof, may therefore be used for preparing electrolytes (liquids, gels or polymers) for lithium batteries which utilize a cathode material having a potential of end of recharge lower than 4 V ($TiS_2$, $V_2O_5$, $Fe(PO_4)_2$). Tin salts (II) may be used for catalyzing aldolic condensations.

EXAMPLE 34

Trifluoro-methane-sulfonyl (2-trifluoromethyl-1,3,4-thiadiazole-5-amino)amide

By operating in a glove box under argon, to 16.91 g (100 mmoles) of 2-amino-5-trifluoromethyl-1,3,4-thiadiazole (commercially available from Aldrich) in solution in 100 ml of anhydrous tetrahydrofurane at −30° C., there is added drop-wise 100 ml of a 1 M solution of dibutylmagnesium ($C_4H_9)_2Mg$ (100 mmoles, commercially available from Aldrich) in heptane. After 4 hours at −30° C., 16.85 g (100 mmoles) of trifluoromethanesulfonyl chloride $CF_3SO_2Cl$ were added slowly. The reaction is continued during 2 hours at −30° C., then for 24 hours at room temperature. The solvents were then evaporated, the product was reclaimed in water and extracted with ether after acidifying the aqueous solution. The compound obtained after evaporation of ether was sublimated under secondary vacuum at 40° C., and 25.73 g of trifluoromethanesulfonyl(5-trifluoromethyl-1,3,4-thiadiazole)amide (86% yield) were thus recovered on a cold finger after 24 hours.

Microanalysis has given. H, 0.39; (0.33); C, 15.29; (15.95); N, 13.28; (13.95); F, 38.3; (37.85); S, 20.62; (21.29).

The lithium salt was obtained by treating the acid with lithium carbonate $Li_2CO_3$ in water.

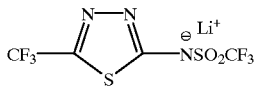

This salt is soluble in most usual organic solvents (tetrahydrofurane, acetonitrile, dimethylformamide, ethyl acetate, glymes, . . . ) and in aprotic solvating polymers such as poly (ethylene oxide).

This salt has an oxidation potential in a mixture of ethylene carbonate and dimethylcarbonate (2:1), at a concentration of 1 M, higher than 4V towards a lithium anode.

EXAMPLE 35

Trifluoro-methane-sulfonyl (2-trifluoromethyl-thiadiazole-5-aminosulfonyl)imide

First, 5-trifluoromethyl-2,3,4-thiadiazole-2-sulfonyl chloride was prepared from 2-amino-trifluoromethyl-1,3,4-thiadiazole (commercially available from Aldrich), following the procedure described in Example 7.

Then, by a procedure similar to the one used in Example 25 for the synthesis of the lithium salt of dimethylaminosulfonyl(trifluoromethanesulfonyl)imide, the lithium salt of trifluoromethanesulfonyl(5-trifluoromethyl-1,3,4-thiadiazole-5-sulfonyl)ide was synthesized. The product obtained has a purity determined by proton and fluorine RMN higher than 98%.

Microanalysis has given: Li, 1.36; (1.9); C, 13.29; (12.9); N, 11.88; (11.3); F, 31.4; (30.7); S, 26.46; (25.9).

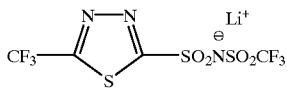

This salt is soluble in most usual organic solvents (tetrahydrofurane, acetonitrile, dimethylformamide, ethyl acetate, glymes, . . . ) and in aprotic solvating polymers such as poly (ethylene oxide).

This salt has an oxidation potential, at a concentration of 0.5 M in acetonitrile, higher than 4.5 V towards a lithium anode. It may be used for Li-Ion batteries with liquid or gel electrolytes. Thus, a battery was assembled by utilizing an anode consisting of coke carbon (80% by volume) mixed with vinylidene polyfluoride (PVDF, commercially available from Montedison) as binder (20% by volume), an electrolyte compound of a mixture of ethylene carbonate and dimethylcarbonate (2:1), gelled with PVDF, containing this salt at a concentration of 1 M and a composite cathode consisting of carbon black (6% by volume), $Li_2MnO_4$ (75% by volume) and PVDF as binder (20% by volume). This generator has given good performances in cycling at 25° C. (1,000 cycles of charge/discharge between 2 and 4.7 V by maintaining about 50% of the capacity at the first cycle).

EXAMPLE 36

Trifluoro-methane-sulfonyl(2-trifluoromethyl-thiadiazole-5-aminosulfonyl)amide

In 20 ml of anhydrous acetonitrile under stirring, 2.29 g (10 mmoles) of trichloromelamine (commercially available from Fluka) were treated with 5.16 g of potassium triflinate in the presence of 6.37 g of potassium phosphate $K_3PO_4$ (30 mmoles). After 72 hours under stirring, the solvent was evaporated and the residue was recrystallized in 40 ml of water. After filtration and drying, 10.69 g (56% yield) of a potassium trisalt of tris-[1,3,5-trifluoromethanesulfonamide]-2,4,6-tri-azine with a purity determined by a proton and fluorine RMN higher than 99%.

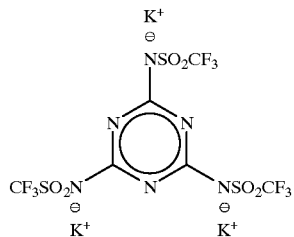

Microanalysis has given: C, 11.52; (11.32); N, 13.61; (13.2); F, 26.99; (26.86); S, 15.01; (15.11); K, 18.21; (18.43).

The trisalt of lithium was obtained by ionic exchange with lithium chloride LiCl in tetrahydrofurane.

The lithium salt is soluble in most of the usual organic solvents (tetrahydrofurane, acetonitrile, dimethylformamide, ethyl acetate, glymes, . . . ) and in aprotic solvating polymers such as poly (ethylene oxide). In this latter solvent containing the lithium salt at a concentration O/Li=12/1, the cationic transport number is 0.52 at 60° C.

The tri-salt of tetrabutylammonium was obtained by treatment of the lithium tri-salt with tetrabutylammonium chloride (5% in excess) in water. The precipitate obtained was thereafter recovered by extraction with dichloromethane, the dichloromethane solution was washed with water, and evaporated. The tri-salt tris-[1,3,5-trifluoromethanesulfonamide]-2,4,6-triazine tri-tetrabutylammonium was recovered in quantitative yield. An addition of 3.5% by weight of this compound to a poly (acrylonitrile-co-butadiene) copolymer containing ≈20% by weight of acrylonitrile gives antistatic properties to the copolymer.

EXAMPLE 37

Trifluoromethanesulfonyl(1,1,1,3,3,3-hexafluoro-2-propanoxysulfonyl)imide 5.96 g (40 mmoles) of trifluoromethanesulfonamide $CF_3SO_2NH_2$ and 9.9 ml of pyridine in 60 ml of anhydrous dichloromethane were cooled to −15° C. 5.4 g (40 mmoles) of sulfuryl chloride $SO_2Cl_2$ diluted in 10 ml of anhydrous dichloromethane were added drop-wise, and this was followed by 6.72 g (40 mmoles) of 1,1,1,3,3,3-hexafluoro-2-propanol $(CF_3)_2CHOH$. The mixture was stirred for 1 hour at −15° C., and during 12 hours at room temperature. The reaction mixture was thereafter filtered, and the solvent was evaporated. The product which was recovered was reclaimed in 50 ml of water, acidified with 10 ml of a hydrochloric acid solution 4 M; the aqueous phase was extracted twice with 20 ml of ether, the organic phase was dried with magnesium sulfate and ether was evaporated by means of a rotary evaporator. After sublimation under secondary vacuum at 40° C. of the compound obtained, 13.9 g of trifluoromethanesulfonyl-(1,1,1,3,3,3-hexafluoro-2-propanoxysulfonyl)imide (92% yield) having a purity characterized by a fluorine and proton RMN higher than 98% were recovered.

Microanalysis has given: H, 0.46; (0.53); C, 12.35; (12.67); N, 3.76; (3.69); F, 44.3; (45.09); S, 16.23; (16.91).

An aqueous solution of the lithium salt was obtained by treating the acid with lithium carbonate $Li_2CO_3$ in water. Then, by addition of 1-ethyl-3-methyl-1H-imidazolium chloride (10% in excess, commercially available from is Aldrich), a liquid phase of higher density than water was obtained. This phase was recovered by extraction with dichloromethane. After evaporation of dichloromethane and drying under vacuum at 40° C. of the liquid obtained, the molten salt of trifluoromethanesulfonyl(1,1,1,3,3,3-hexafluoro-2-propanoxysulfonyl)imide 1-ethyl-3-methyl-1H-imidazolium was recovered (91% yield).

This molten salt has a conductivity of $3.91 \times 10^{-3}$ S.cm$^{-1}$ and a freezing point lower than −20° C. Its large range of redox stability enables it to be a particularly interesting electrolyte for electrochemical generators such as lithium batteries, supercapacitances, systems for modulating light and photovoltaic cells.

An electrochemical photovoltaic cell was prepared by assembling a system made of two electrodes separated by a vacuum space 30 μm thick. The first electrode was coated with a layer of nanoparticles of titanium dioxide $TiO_2$ 0.25 μm thick on which the 1,3-phenylsulfonamide-N,N'-trifluoro-methanesulfonyl rhodamine B obtained in Example 25 was adsorbed as a sensitizer. The space between the electrodes was filled with an electrolyte made of the molten salt in which 10% by weight of methylhexyl imidazolium and 10 mmoles of iodine were solubilized. The short circuit current of this cell is 103 μA.cm$^{-2}$ and its voltage in open circuit was 552 mV.

EXAMPLE 38

Cyano(perfluorobutanesulfonyl)imide

To 5.16 g (60 mmoles) of cyanamide di-sodium (commercially available from Aldrich) in 30 ml of dimethoxyethane at 0° C., there is added 15.1 g of perfluorobutanesulfonyl fluoride (50 mmoles) at 0° C. After 3 hours at 0° C., and 24 hours at room temperature, the reaction mixture was centrifuged and filtered to remove the excess of cyanamide and the sodium fluoride formed. The product obtained was reclaimed in 20 ml of methanol after evaporation of dimethoxyethane, and 4.91 g of anhydrous potassium acetate $CH_3COOK$ (50 mmoles) were added. The precipitate which was formed is recrystallized, and recovered by filtration. After drying, 12.5 g of potassium perfluorobutanesulfonyl (cyano)imide $C_4F_9SO_2NKCN$ (69% yield) were obtained in the form of a white powder having a purity characterized by a fluorine and proton RMN higher than 97%.

Microanalysis has given: C, 16.18; (16.58); N, 7.23; (7.73); F, 47.98; (47.21); S, 8.12; (8.85); K, 11.2; (10.79).

In the same manner, potassium salts of cyano (fluorosulfonyl)imide (I) were prepared from fluorosulfonyl chloride ClSO$_2$F, cyano(trifluoromethanesulfonyl)imide (II) was prepared from trifluoromethanesulfonyl chloride CF$_3$SO$_2$Cl and cyano(pentafluoroethanesulfonyl)irnide (III) was prepared from pentafluoroethanesulfonyl chloride C$_2$F$_5$SO$_2$Cl.

 (I)

 (II)

 (III)

The lithium salts were prepared in quantitative yield by ionic exchange between the potassium salt and lithium chloride in anhydrous tetrahydrofurane.

These salts are soluble in most of the usual organic solvents (tetrahydrofurane, acetonitrile, dimethylformamide, ethyl acetate, glymes, . . . ) and in aprotic solvating polymers such as poly (ethylene oxide). In this latter solvent, it has a conductivity higher than $2\times10^{-4}$ S.cm$^{-1}$ at 60° C. for a concentration O/Li=12/1.

An electrochemical supercapacitance was prepared by utilizing a 1 M solution of each of the above potassium salts in acetonitrile as electrolytes and carbon/aluminum composites as electrodes. For each supercapacitance, the electrodes with a thickness of 150 μm were placed on both sides of a microporous polyethylene 40 μm thick impregnated with a potassium salt and the complete system was sealed in a glove box in a button shaped battery housing. Good performances were obtained with these supercapacitances (more than 100,000 cycles of charge/discharge between 0 and 2.5 V for a density of energy higher than 25 W/l and a delivered power higher than 1,500 W/l.

EXAMPLE 39

Alkylsulfonyl(trifluoromethanesulfonyl)imide 7.83 g (50 mmoles) of butanesulfonyl chloride C$_4$H$_9$SO$_2$Cl in (solution in 30 ml of anhydrous tetrahydrofurane at 0° C. were treated with 17.11 g (100 mmoles) of sodium trifluoromethanesulfonamide CF$_3$SO$_2$NHNa. After 1 hour at 0° C., and 24 hours at room temperature, the solvent was evaporated and the product was reclaimed in 50 ml of water. An addition of 3.73 g of anhydrous potassium chloride KCl (50 mmoles) resulted in the appearance of a precipitate which was recrystallized, and recovered by filtration and fmally dried. 9.37 g of potassium trifluoromethanesulfonyl(butanesulfonyl)imide (61% yield) C$_4$H$_9$SO$_2$NKSO$_2$CF$_3$ were thus obtained in the form of a crystallized white powder, having a purity determined by a fluorine and proton RMN higher than 99%.

Microanalysis has given: H, 2.75; (2.95); C, 19.01; (19.54); N, 4.98; (4.56); F, 18.21; (18.54); S, 20.25; (20.86); K, 12.56; (12.72).

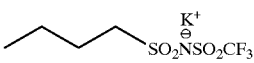

Potassium trifluoromethanesulfonyl(octylsulfonyl)imide (I) and potassium trifluoromethanesulfonyl (dodecylsulfonyl)imide (II) were obtained under identical conditions respectively from octylsulfonyl chloride and dodecylsulfonyl chloride.

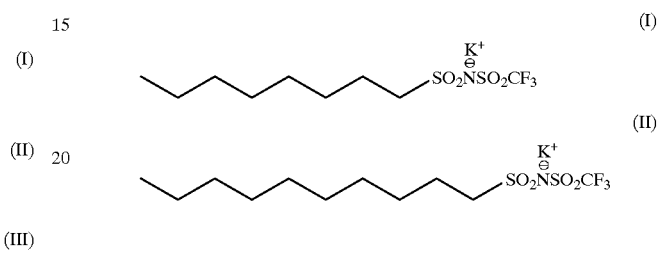

The lithium salts of these three derivatives were prepared in quantitative yield by ionic exchange between the potassium salt and lithium chloride in anhydrous tetrahydrofurane. The lithium salt of trifluoromethanesulfonyl (dodecylsulfonyl)imide dissolved in a matrix of poly (ethylene oxide) at a concentration O/Li=16/1 has a cationic transport number of about 0.55. The result is that when this compound is used as an electrolyte in a polymer electrolyte lithium battery, the gradients of concentration which appear during the operation of the battery are decreased substantially. Performances during calls for power are thus improved.

EXAMPLE 40

Octylsulfonyl(fluorosulfonyl)imide 5.16 g (25 mmoles) of octylsulfonyl chloride C$_8$H$_{17}$SO$_2$Cl in solution in 20 ml of anhydrous tetrahydrofurane at 0° C. were treated with 6.86 g (50 mmoles) of potassium fluorosulfonamide. After 1 hour at 0° C. and 24 hours at room temperature, the solvent was evaporated and the product was recrystallized in 15 ml of water. After filtration and drying, 5.64 g of potassium fluorosulfonyl (butanesulfonyl) imide C$_8$H$_{17}$SO$_2$NKSO$_2$F (72% yield) having a purity determined by a fluorine and proton RMN higher than 99% was recovered. The lithium salt was prepared by ionic exchange (metathesis) between the potassium salt and lithium chloride in anhydrous tetrahydrofurane.

Microanalysis has given: H, 5.27; (5.47); C, 30.98; (30.66); N, 4.78; (4.47); F, 6.52; (6.06); S, 20.96; (20.46); K, 12.01; (12.47).

The lanthanum salt of fluorosulfonyl(butanesulfonyl) imide C$_8$H$_{17}$SO$_2$NKSO$_2$F may be used as catalyst for Diels-Alder reactions, in particular in dichloromethane.

These salts possess plasticizing properties.

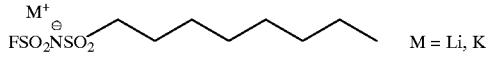

EXAMPLE 41

Triisopropylsulfonyl(fluorosulfonyl)imide 3.96 g of fluorosulfonamide FSO$_2$NH$_2$ (40 mmoles) and 12.11 g of 2,4,6-triisopropylbenzenesulfonyl chloride (40 mmoles, commercially available from Aldrich), were stirred in 40 ml of anhydrous tetrahydrofirane at 0° C. in the presence of 8.49 g of anhydrous potassium phosphate $K_3PO_4$. After 3 hours at 0° C., and 48 hours at room temperature, the solvent was evaporated and the product was reclaimed in 24 ml of cold water. The addition of 2.98 g of anhydrous potassium chloride gave a precipitate which was recrystallized, recovered by filtration, and dried. There is thus obtained 11.78 g of potassium fluorosulfonyl fluorosulfonyl (2,4,6-triisopropyl-benzenesulfonyl)imide (73% yield) having a purity determined by a fluorine and proton RMN higher than 98%.

Microanalysis has given: H, 5.58; (5.98); C, 44.14; (44.53); N, 3.78; (3.46); F, 5.02; (4.7); S, 15.23; (15.85); K, 10.21; (9.66).

The lithium salt was prepared by ionic exchange (metathesis) between the potassium salt and lithium chloride in anhydrous tetrahydrofurane.

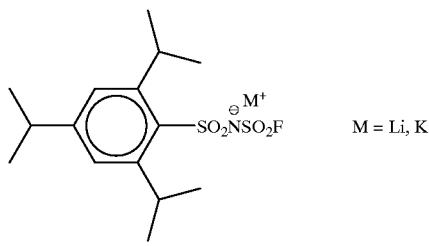

EXAMPLE 42

1-dodecyl-1,1,1,3,3,3-hexafluoro-2-propanoxysulfonyl(trifluoromethanesulfonyl)imide By operating in a glove box under argon, 18.96 g (50 mmoles) of trifluoromethanesulfonyl(1,1,1,3,3,3-hexafluoro-2-propanoxy-sulfonyl)imide prepared as in Example 37, were placed in solution in 20 ml of anhydrous tetrahydrofurane. After having brought this solution to −20°

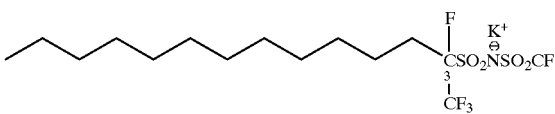

The lithium salt was obtained in quantitative yield by treating the potassium salt in anhydrous tetrahydrofurane by a stoichiometric quantity of anhydrous lithium chloride, filtration of the reaction mixture, evaporation of the solvent and drying under vacuum.

These salts may be used as additives for laminating lithium and for the extrusion of polymers, in particular the extrusion of poly (ethylene oxide). They have plasticizing properties.

EXAMPLE 43

Igepal® CA-520-propylsulfonyl (trifluoromethanesulfonyl)imide

In 30 ml of tetrahydrofurane, 4.27 g of Igepal® CA-520 (10 mmoles, commercially available from Aldrich) were treated with 3.28 (10 mmoles) of trifluoromethanesulfonyl (3-chloropropanesulfonyl)-imide obtained as in Example 8, in the presence of 4.24 g of potassium phosphate $K_3PO_4$ (20 mmoles). After 72 hours under stirring at 60° C., the reaction mixture was filtered so as to remove potassium phosphate and potassium chloride formed during the reaction. After evaporation of the solvent and drying, 7.18 g of potassium Igepal(® CA-520-propyl-sulfonyl (trifluoromethanesulfonyl)imide having a purity determined by proton and fluorine RMN higher than 96% were recovered.

Microanalysis has given: H, 6.89; (6.6); C, 46.45; (46.85); N, 1.69; (1.95); F, 7.66; (7.94); S, 8.72; (8.93); K, 5.75; (5.45).

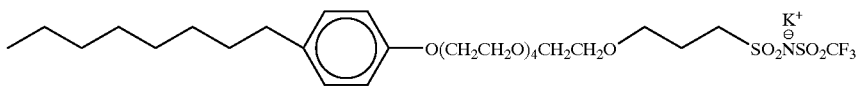

C., 10 ml of a 1 M solution of potassium tert-butoxide $(CH_3)_3COK$ (100 mmoles, commercially is available from Aldrich) in tetrahydrofurane were added slowly. After 15 minutes, 12.46 g of 1-bromododecane (50 mmoles) were added. The reaction is continued for 2 hours at −20° C., then during 24 hours at room temperature. After 48 hours, the solvent was evaporated and the residue was recrystallized in 50 ml of water containing 7.46 g (100 mmoles) of potassium chloride KCl. After filtration and drying, there is obtained potassium 1-dodecyl-1,1,1,3,3,3-hexafluoro-2-propanoxysulfonyl-(trifluoromethanesulfonyl)imide of a purity characterized by a proton and fluorine RMN higher than 99%.

Microanalysis has given: H, 4.8; (4.5); C, 34.5; (34.1); N, 2.8; (2.3); F, 28.1; (28.5); S, 10.1; (10.7); K, 6.1; (6.5).

This salt is an excellent additive for the extrusion of poly (ethylene oxide). It also enables to plasticize a large number of polymers containing polar units (ether, amide, nitrile, ester . . . ), while giving them a high ionic conductivity.

EXAMPLE 44

Toluenesulfonyl(trifluoromethanesulfonyl)imide

By operating in a glove box under argon, 3.23 g of dichlorotriphenylphosphorane $(C_6H_5)_3PCl_2$ (10 mmoles) were added by portions to a solution of 2.24 g (20 mmoles) of DABCO and 1.49 g of trifluoromethanesulfonamide $CF_3SO_2NH_2$ (10 mmoles) in 20 ml of acetonitrile. After 3 hours under stirring, the reaction mixture was filtered to remove the precipitate of DABCO chloride formed, and the solvent was evaporated. There was recovered a quantitative yield of triphenylphosphoranylidene-sulfonyl-trifluoromethyl $CF_3SO_2N=P(C_6H_5)_3$ in quantitative yield. Then, this compound was reacted with 1.94 g (10 mmoles)

of the sodium salt of p-toluenesulfonic acid in 10 ml of dimethylformamide at 60° C. After 48 hours under sting, the solvent was evaporated and the residue was recrystallized in 10 ml of water containing 1 g of potassium chloride KCl. After filtration and drying, 2.46 g of sodium p-toluenesulfonyl(trifluoromethanesulfonyl)imide (76% yield) having a purity determined by a proton and fluorine RMN higher than 99% were recovered.

Microanalysis has given: H, 2.07; (2.17); C, 29.88; (29.54); N, 4.01; (4.31); F, 17.23; (17.52); Na, 7.15; (7.07); S, 19.21; (19.71).

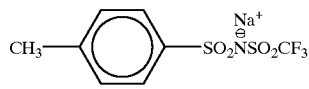

EXAMPLE 45

O,O'-[propylsulfonyl-(trifluoromethanesulfonyl)imide]polyethylene glycol

A sulfonated oligomer of poly (ethylene oxide) was prepared as follows: 12 g of poly(ethylene glycol) of molecular weight 600 (≈40 mmoles of hydroxyl functions) were dried by azeotropic distillation with benzene and by lyophilization. After addition of 50 ml of anhydrous tetrahydrofurane, the terminal hydroxyl groups were metal substituted with potassium-naphthalene. The stoichiometry was determined by colorimetry, and the end of the reaction was indicated by a persistence of an intense green color of the anion radical of naphthalene. Then, 4.89 g of 1,3-propane sultone (40 mmoles) were added. After evaporation of the solvent, the αω-disulfonated polymer was obtained in the form of powder and the residual naphthalene was removed by washing with hexane. 8.44 g of the product thus formed (≈20 mmoles of —$SO_3H$), in suspension in 20 ml of anhydrous acetonitrile, were treated with 2.82 g of (chloromethylene)dimethylammonium chloride [$(CH_3)_2N=CHCl$]$^+$, Cl$^-$ (22 mmoles, commercially available from Aldrich). A precipitate of potassium chloride was formed after about 1 h. 3.28 g of trifluoromethanesulfonamide (22 mmoles) and 2.47 g of DABCO (22 mmoles) were added to this suspension. After filtration, the reaction mixture was stirred in the presence of 3.4 g of lithium phosphate $Li_3PO_4$ during 24 hours. A new filtration followed by a reprecipitation in 200 ml ether at 0° C. has enabled to recover a viscous fluid which is very lightly colored, characterized by a proton and fluorine RMN as in the case of the di-lithium salt of poly(ethylene glycol) α,ω-trifluoromethanesulfonyl-(propanesulfonyl)imide:

This salt is soluble in most polar organic solvents (acetonitrile, tetrahydroflirane, DMF, . . . ) and it may be used to plasticize a large number of polymers containing polar units (ether, amide, nitrile, ester . . . ), while giving them a high ionic conductivity.

EXAMPLE 46

Trifluoromethanesulfonyl(R(-)-1-phenyl-2,2,2-trifluoroethanoxysulfonyl)imide 5.96 g (40 mmoles) of trifluoromethanesulfonamide and 9.9 ml of pyridine in 60 ml of anhydrous dichloromethane were cooled to -15° C. 0.4 g (40 mmoles) of sulfiuyl chloride diluted in 10 ml of anhydrous dichloromethane were then added drop-wise, followed by 7.05 g (40 mmoles) of R(-)-1-phenyl-2,2,2-trifluoroethanol (commercially available from Fluka). The mixture was stirred for 1 hour at -15° C., and for 4 hours at room temperature (25° C.) The reaction mixture was filtered and the solvent was removed with a rotary evaporator. The product which was recovered was reclaimed in 20 ml of ethanol. A precipitate is formed after the addition of 3.93 g (40 mmoles) of potassium acetate. After recrystallization, filtration and drying, there is obtained 12.25 g of potassium trifluoromethanesulfonyl(R (-)-1-phenyl-2,2,2-trifluoroethanoxysulfonyl)imide (72% yield) having a purity characterized by a fluorine and proton RMN higher than 98%.

Microanalysis has given: H, 1.65;(1.42); C, 25.21; (25.41); N, 3.55; (3.29), F, 26.21; (26.8); S, 15.65; (15.07); K, 9.56; (9.19).

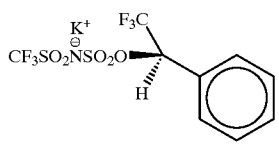

In the same manner, potassium trifluoromethanesulfonyl-(S(+)-1-phenyl-2,2,2-trifluoroethanoxysulfonyl)imide (66% yield) was obtained from R(-)-1-phenyl-2,2,2,-trifluoroethanol.

Lithium salts were obtained by ionic exchange (metathesis) in tetrahydrofurane with lithium chloride.

Lanthanum salts were obtained by treating potassium salts with a stoichiometric quantity of lanthanum perchlorate $La(ClO_4)_3,6H_2O$ in a mixture of acetonitrile and isopropyl orthoformate intended to remove the water of crystallation from the salt of lanthanum. After filtration to remove the precipitate of potassium perchlorate $KClO_4$ and evaporation of the solvent, the lanthanum salts of the two enantiomers of trifluoromethanesulfonyl-(1-phenyl-2,2,2-trifluoroethanoxysulfonyl)imide were recovered in quantitative yield.

These salts are soluble in most polar organic solvents (acetonitrile, tetrahydrofurane, DMF, . . . ) and in aprotic solvating polymers.

EXAMPLE 47

Trifluoromethanesulfonyl(N-methoxybutyl-N-2-butyl-3-methyl)aminosulfonyl)imide

The two enantiomers of the potassium salt of trifluoromethanesulfonyl(N-methoxybutyl-N-2-butyl-3-methyl)aminosulfonyl)-imide were obtained by a process similar to the one described in Example 28, from N-methoxybutyl-N-2-butyl-2-methylamine (commercially available from Air Products) with a purity higher than 99% and a yield of 62%.

By the same process, potassium salts of the two enantiomers of fluorosulfonyl(N-methoxybutyl-N-2-butyl-3-methyl)-aminosulfonyl)imide were also obtained.

The lithium salts are obtained by ionic exchange (metathesis) in tetrahydroflirane with lithium chloride.

By a process similar to the one described in Example 46, lanthanum salts of the two enantiomers of trifluoromethanesulfonyl-(N-methoxybutyl-N-2-butyl-3- methyl)aminosulfonyl)-(N-methoxybutyl-N-2-butyl-3-methyl)aminosulfonyl)imide and the two enantiomers of fluorosulfonyl-(N-methoxybutyl-N-2-butyl-3-methyl)amino-sulfonyl imide were obtained.

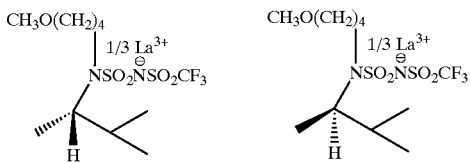

These salts are soluble in most polar organic solvents (acetonitrile, tetrahydrofiirane, DMF, . . . ) and in aprotic solvating polymers.

EXAMPLE 48

Camphorsulfonyl(trifluoromethanesulfonyl)imide

According to a process similar to the one described in Example 39, the potassium salt of (1R)-(−)-10-camphorsulfonyl(trifluoromethanesulfonyl)imide was obtained from (1R)-(−)-10-camphorsulfonyl (commercially available from Aldrich), and potassium (1S)-(+)-10-camphorsulfonyl(trifluoromethanesulfonyl)-imide was obtained from (1S)-(+)-10-camphorsulfonyl chloride (commercially available from Aldrich) with yields higher than 70%. The purity of the compounds obtained, determined by proton and fluorine RMN, is higher than 99%.

The potassium salt of (1r)-(−)-10-camphorsulfonyl (perfluorobutane-sulfonyl)imide and (1S)-(+)-10-camphorsulfonyl(perfluorobutanesulfonyl)imide were obtained from perfluorobutanesulfonamide $C_4F_9SO_2NH_2$ obtained in Example 4.

Lithium salts were obtained by ionic exchange (metathesis) in tetrahydrofuran with lithium chloride.

By a process similar to the one described in Example 46, lanthanum salts of (1R)-(−)-10-camphorsulfonyl (perfluorobutane-sulfonyl)imide and of (1s)-(+)-10-camphorsulfonyl(perfluorobutanesulfonyl)imide were obtained:

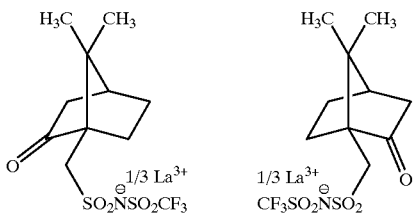

These salts are soluble in most polar organic solvents (acetonitrile, tetrahydrofurane, DMF, . . . ) and in aprotic solvating polymers.

EXAMPLE 49

N-(1S-(+)-ketopinic-acetylmethylsulfonyl (trifluoromethanesulfonyl)imide

By operating in a glove box under argon, 2.8 g (10 mmoles) of the potassium salt of trifluoromethanesulfonyl (N-methyl-sulfonyl) imide $CF_3SO_2NKSO_2NH(CH_3)$ obtained in Example 10, in solution in 5 ml of anhydrous tetrahydrofurane, there is slowly added 10 ml of a 1 M solution in tetrahydrofurane of potassium tert-butoxide $(CH_3)_3COK$ (10 mmoles).

At the same time, to 1.82 g (10 mmoles) of (1S)-(+)-ketopinic acid (commercially available from Aldrich) in solution in 10 ml of anhydrous acetonitrile, there is added 80 mg of lithium hydride LiH (10 mmoles), and after a few minutes, 1.27 g of oxalyl chloride ClCOCOCl (10 mmoles). After centrifugation, the solution of THF was poured into this solution. The reaction was continued 24 hours at room temperature. The reaction mixture was then filtered to remove the precipitate of potassium chloride, and the solvent was evaporated and the product recrystallized in 6 ml of water. After filtration and drying, 2.76 g of potassium trifluoromethanesulfonyl(N-(1S)-(+)-ketopinic-acetyl-N-methyl-sulfonyl)imide (62% yield) were obtained with a purity characterized by a proton and fluorine RMN higher than 99%.

The scandium salt was obtained by treating the potassium salt with a stoichiometric quantity of scandium tetrafluoroborate $Sc(BF_4)_3$ in acetonitrile. After ffiltration to remove the precipitate of potassium tetrafluoroborate $KBF_4$ and evaporation of the solvent, after drying, the scandium salt of trifluoromethanesulfonyl(N-(1S)-(+)-ketopinic-acetyl-N-methylsulfonyl)imide was recovered in quantitative yield.

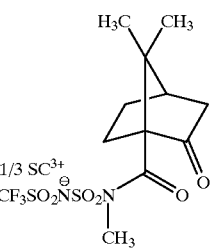

EXAMPLE 50

Dialkylaminosulfonyl(trifluoromethanesulfonyl) imide-diphenyliodonium 1.58 g (5 mmoles) of diphenyliodonium chloride $(C_6H_5)_2ICl$ and 1.89 g of potassium trifluoromethanesulfonyl (dibutyl-aminosulfonyl)imide $(C_4H_9)_2NSO_2NKSO_2CF_3$ (5 mmoles) were stiffed together during 24 hours in water. By extraction of the aqueous phase with dichioromethane, after evaporation is of dichloromethane and drying, 3.01 g of the diphenyliodonium salt of trifluoromethanesulfonyl (dibutylaminosulfonyl)imide (97% yield) were obtained with a purity characterized by a proton and fluorine RMN higher than 99%.

By the same process, the diphenyliodonium salt of trifluoromethanesulfonyl(N,N-di-3-ethylhexyl-aminosulfonyl)imide was prepared with a yield of 98% and with a purty characterized by a proton and fluorine RMN higher than 99%.

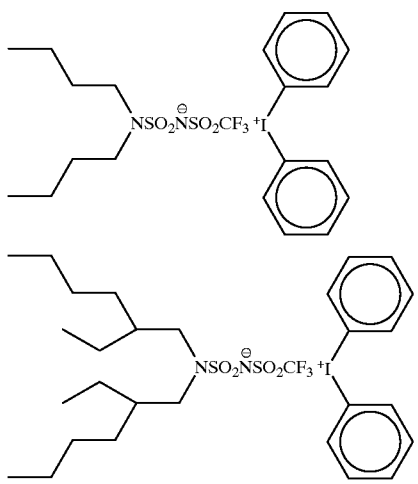

These salts enable to initiate under the action of actinic radiation (light, γ rays, electron beams) a cationic cross-linking reaction of monomers rich in electrons (vinyl ethers, alkyl vinyl ethers).

They are soluble in most usual organic solvents (tetrahydrofurane, acetonitrile, dimethylformamide, ethyl acetate, glymes, . . . ) and in aprotic solvating polymers such as poly (ethylene oxide). They are also soluble to an extent of 10% by weight in reactive solvents such as triethyleneglycol divinyl ether. The properties of photo-initiation of these salts were tested by irradiating with U.V. radiation at 254 nm, a power of 1,900 mW/cm$^2$, a solution of triethyleneglycol divinyl ether containing same at 1% by weight. After a few seconds under irradiation, the reactive solvent has solidified, this reaction being very exothermal.

EXAMPLE 51

(4-butoxybenzene)-[trifluoromethanesulphonyl-(4-phenylsulfonyl)imide)]-iodonium

To a solution of 4.49 g (40 mmoles) of DABDO and 2.98 g of trifluoromethanesulfonamide $CF_3SO_2NH_2$ (20 mmoles), in 10 ml of anhydrous tetrahydrofurane at 0° C., there is added 6.05 g of 4-iodobenzenesulfonyl chloride $IC_6H_4SO_2Cl$ (20 mmoles, Aldrich) diluted in 5 ml of anhydrous tetrahydrofurane. After 2 hours at 0° C., the reaction was continued during 24 hours at room temperature. The DABCO hydrochloride formed during the reaction was removed by filtration on a fritted glass of porosity No. 4. After evaporation of acetonitrile from the filtered solution, the product was reclaimed in 15 ml of cold water and there was slowly added 1.49 g of anhydrous potassium chloride (20 mmoles) in solution in 5 ml of water. A precipitate appeared which was collected by filtration on a fritted glass of porosity No. 4. After drying, 7.89 g of potassium trifluoromethanesulfonyl(4-iodobenzenesulfonyl)imide (87% yield) having a purity characterized by a proton and fluorine RMN higher than 99% were recovered.

This compound was oxidized into $CF_3SO_2NKSO_2C_6H_4I$ $(O_2CCH_3)_2$ (iodosoacetate) with a mixture of acetic acid, acetic anhydride and hydrogen peroxide according to the method of Yamada & al (Die Makromolecular Chemie, (1972), 152, 153–162). 5.71 g of the compound thus prepared (10 mmoles) were suspended in a mixture of 15 ml of methanesulfonic acid and 4.51 g of butoxybenzene (30 mmoles) kept at 0° C. during 4 hours. The reaction product was poured into 300 ml ether and the precipitate was separated by filtration, washed with ether and dried. There is thus obtained 4.62 g (82% yield) of a zwitterion of (4-butoxybenzene)-[trifluoromethanesulfonyl-(4-phenylsulfonyl)-imide] iodonium $[CF_3SO_2N^-SO_2C_6H_4I^+$ $C_6H_4OC_4H_9]$ having a purity characterized by a proton and fluorine RMN higher than 97%.

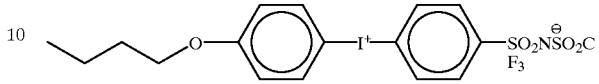

By a similar process, the compound (4-butoxybenzene)-[pentafluoroethanesulfonyl-4(4-phenylsulfonyl)imide] iodonium was obtained from pentafluoroethanesulfonamide and (4-butoxy-benzene)-[perfluorobutanesulfonyl-(4-phenyl-sulfonyl)imide]iodonium from perfluorobutanesulfonamide. These compounds have analogous properties to those of the compounds of Example 50 and may be used for the same application.

EXAMPLE 52

Tetrakis(acetonitrile)palladium(II) trifluoromethanesulfonyl(N,N-di-2-ethylhexylaminosulfonyl)imide 2.22 g (5 mmoles) of tetrakis(acetonitrile)palladium tetrafluoroborate(II) $(CH_3CN)_4Pd(BF_4)_2$ (commercially available from Aldrich), in 30 ml of tetrahydrofurane were treated with 4.91 g of potassium trifuoromethanesulfonyl(N,N-di-2-ethylhexylaminosulfonyl)imide (10 mmoles) obtained in Example 28. After 24 hours under stirring, the reaction mixture was ifiltered to remove the precipitate of potassium tetrafluoroborate KBF4, and the solvent was evaporated. Trifluoromethanesulfonyl-(N,N-di-2-ethylhexylaminosulfonyl)imide of tetrakis-(acetonitrile) palladium(II) was obtained in quantitative yield.

This salt is useful as catalyst for the vinyl polymerization of norbornene. Thus, norbomene was polymerized at room temperature in nitromethane in the presence of 300 ppm of this salt. After 2 hours, the reaction mixture was reprecipitated in methanol. Polynorbornene was obtained with a number average molecular weight of 420,000 with a yield of 82%.

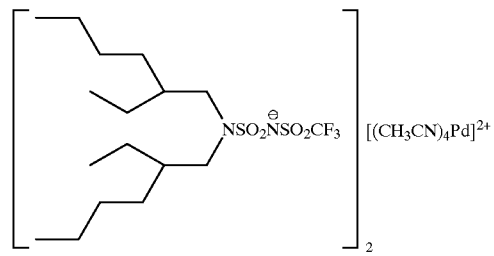

EXAMPLE 53

5-dimethylamino-1-naphthalenesulfonyl(trifluoromethanesulfonyl)imide

In 20 ml of anhydrous acetonitrile, 5.39 g (20 mmoles) of 5-dimethyl-amino-1-naphthalenesulfonyl chloride (commercially available from Aldrich) was reacted with 2.98 g (20 mmoles) of trifluoromethane-sulfonamide $CF_3SO_2NH_2$ 4.49 g (40 mmoles) of DABCO. After 24 hours under stirring at room temperature, the reaction mixture was filtered to remove the DABCO hydrochloride formed, and acetonitrile was evaporated. The product obtained was recrystallized in 20 ml of water containing 2.98 g (40 mmoles) of potassium chloride. After filtration and drying, 5.63 g of potassium trifluoromethane-sulfonyl(5-dimethylamino-1-naphthalenesulfonyl)imide (69% yield) was recovered with a purity characterized by a fluorine and proton RMN higher than 99%.

Microanalysis has given: H, 2.96; (2.88); C, 37.23; (37.14); N, 6.41; (6.66); F, 13.98; (13.56); S, 15.65; (15.25); K, 9.46; (9.3).

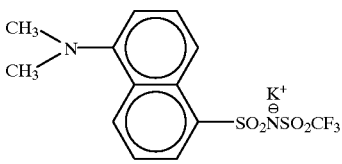

This fluorescent salt is soluble in most polar organic solvents (acetonitrile, tetrahydrofinane, DMF, . . . ).

EXAMPLE 54

N-trifluoromethanesulfonyl-2-aminoacridine

Using a process similar to the one described in Example 34, the magnesium salt of N-trifluorometianesulfonyl-2-aminoacridine was obtained by action of trfluoromethane-sulfonyl chloride on magnesium 2-aminoacridine in tetrahydrofurane. After evaporation of the solvents, the product was reclaimed in water and treated with tetraethylammonium (10% in excess) in water, and a precipitate then appeared. After filtration and drying, N-trifluoromethanesulfonyl-2-aminoacridine tetraethylammonium (66% yield) was obtained with a purity determined by a proton and fluorine RMN higher than 99%.

Microanalysis has given: H, 6.11; (6.39); C, 59.25; (59.85); N, 6.89; (6.34); F, 12.25; (12.91); S, 7.95; (7.26).

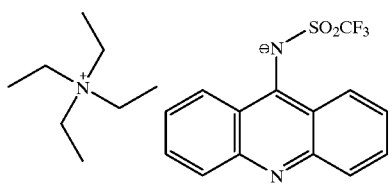

In the same manner, N-fluorosulfonyl-2-aminoacridine tetraethylammonium was obtained from fluorosulfonamide.

This salt is soluble in most usual organic solvents (tetrahydrofurane, acetonitrile, dimethylformamide, ethyl acetate, glymes, . . . ) and in aprotic solvating polymers such as poly (ethylene oxide), as well as in polymers with low polarity such as methyl polymethacrylate.

These salts have a very substantial fluorescence. A dichloroethane solution of polymethylmethacrylate (PMM) and of either of these ammonium salts (97:3) was prepared. Fluorescent deposits were obtained on a number of supports (glass, polymer, . . . ).

EXAMPLE 55

1,3-phenylsulfonamide-N,N'-perfluoro-1-butane-sulfonyl rhodamine B

To 2.9 g of sulforhodamine B (5 mmoles, commercially available from Aldrich) in 50 ml of anhydrous dimethylformamide, there is added 941 mg of the potassium salt of trifluoromethanesulfonic acid $CF_3SO_3K$ (5 mmoles). After 2 hours under stirring, 1.27 g of oxalyl chloride ClCOCOCl (10 mmoles) in solution in 10 ml of anhydrous dichloromethane was added slowly. The reaction was continued overnight under argon, and 6.74 g of potassium perfluoro-1-butanesulfonamide $C_4F_9SO_2NHK$ (20 mmoles) were added. After 48 hours, dimethylformamide was evaporated and the residue was recrystallized in 40 ml of water. After filtration and drying, there is obtained 4.11 g (71% yield) of the potassium salt of 1,3-phenyl-sulfonamide-N, N'-(perfluoro-2-butanesulfonyl) rhodamine B having a purity characterized by a proton and fluorine RMN higher than 99%.

Microanalysis has given: H, 2.76; (2.52); C, 36.56; (36.27); N, 4.96; (4.83); F, 29.99; (29.51); S, 11.55; (11.07); K, 3.17; (3.37).

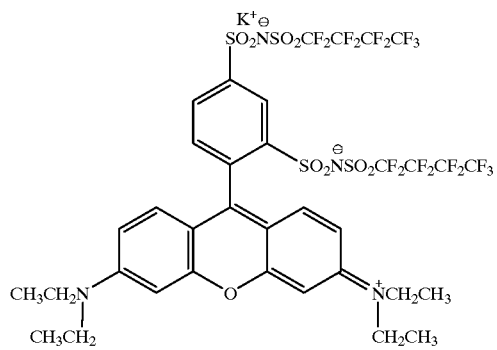

By the same process, the di-potassium salt of 1,3-phenylsulfonamide-N,N'-fluorosulfonyl rhodamine B was obtained from the potassium salt of fluorosulfonamide, the di-potassium salt of 1,3-phenylsulfonamide-N,N'-trifluoromethanesulfonyl rhodamine B was obtained from the potassium salt of trifluoromethanesulfonamide and the di-potassium salt of 1,3-phenylsulfonamide-N,N'-pentafluoroethane-sulfonyl rhodamine B was obtained from pentafluorosulfonamide.

Lithium salts were obtained by metathesis with lithium chloride in tetrahydrofurane.

These zwitterions have intense dying properties. They are soluble in polar polymers and permit the production of colorants containing lasers. The sulfonimide groups also enable them to be adsorbed on oxides, in particular nanoparticular titanium dioxide; they then act as a sensitizer towards visible radiation, in particular in applications to photovoltaic cells.

EXAMPLE 56

Trifluoromethanesulfonyl(anthracenyl-9-ethanesulfonyl)imide

In a Parr chemical reactor, there is introduced a solution of 9.36 g of the potassium salt of trifluoromethanesulfonamide $CF_3SO_2NHK$ (50 mmoles) and of 264 of crown ether, 18-Crown-6 (acting as complexing agent of the potassium cation), in 60 ml of anhydrous acetonitrile. After closing the reactor, the reactor was flushed with argon during 15 minutes before isolating it. There is then introduced 6.41 g of sulfur dioxide $SO_2$ (50 mmoles, commercially available from Fluka) and, after 10 minutes, 10.21 g of 9-vinylanthracene (50 mmoles, commercially available from Lancaster) in solution in 20 ml of anhydrous dichloromethane. After 6 hours at room temperature, the temperature of the reactor was set at 50° C. and kept therein during 48 hours, and the solvent was evaporated and the product was dried. The potassium salt of trifluoromethanesulfonyl (anthracenyl-9-ethanesulfonyl)imide was recovered in quantitative yields with a purity characterized by a fluorine and proton RMN higher than 99%.

Microanalysis has given: H, 2.78; (2.88); C, 44.53; (44.83); N, 3.33; (3.07); F, 12.01; (12.51); S, 14.36; (14.08); K, 8.99; (8.58).

Using the same process, the potassium salt of flurosulfonyl(anthracenyl-9-ethanesulfonyl)imide was obtained.

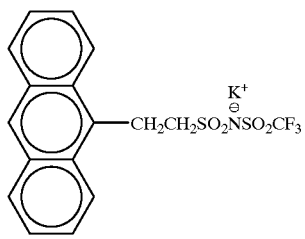

This salt is soluble in most usual organic solvents (tetrahydrofurane, acetonitrile, dimethylfonnamnide, ethyl acetate, glymes, ...) and in polar polymers.

EXAMPLE 57

N,N',N'',N'''-perfluorobutanesulfonyl-nickel(II) phtalocyaninetetrasulfonamide

To 4.9 g of the sodium salt of Nickel(II) phthalocyaninetetrasulfonic acid (5 mmoles, commercially available from Aldrich) in 40 ml of anhydrous dimethylformamide, there is slowly added 2.54 g of oxalyl chloride ClCOCOCl (20 mmoles) in solution in 10 ml of anhydrous dichloromethane. After 4 hours under stirring, the reaction mixture was centrifuged, the liquid floating on the surface was removed, and the decanted product was reclaimed in 40 ml of anhydrous dimethylformamide. Then, 13.5 g of the potassium salt of perfluoro-1-butanesulfonamide $C_4F_9SO_2NHK$ (40 mmoles) were added. After 48 hours, the dimethylformamide was evaporated and the residue was recrystallized in 50 ml of water containing 1.49 g (20 mmoles) of anhydrous potassium chloride. After filtration and drying, there is obtained 9.54 g (81% yield) of the potassium salt of N,N', N'',N'''-perfluorobutanesulfonyl-Nickel(II) phtalocyaninetetrasulfonamide having a purity characterized by a proton and fluorine RMN higher than 99%.

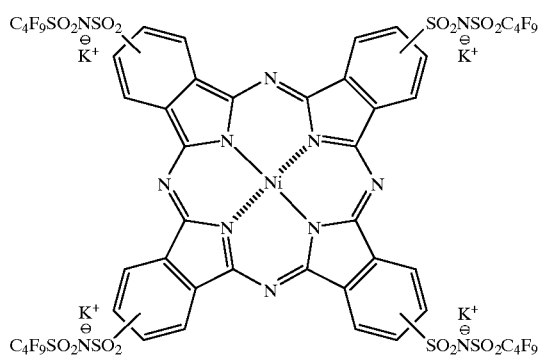

This salt is soluble in most usual organic solvents (tetrahydrofurane, acetonitrile, dimethylformamide, ethyl acetate, glymes, ...) and in polar polymers to which it gives an intense blue color and which is stable towards light. This salt, as well as analogous nickel, iron or manganese salts are useful as catalysts for the reduction of oxygen.

EXAMPLE 58

In 30 ml of THF, 6.76 g of pentafluoropyridine (40 mmoles, commercially available from Aldrich) are reacted with 7.49 g (40 mmoles) of the potassium salt trifluoromethanesulfonamide $CF_3SO_2NHK$ in the presence of 4.49 g (40 mmoles) of DABCO. After 48 hours under stirring, the solvent was evaporated and the residue was recrystallized in 20 ml of water. After filtration and drying, 8.03 g of the potassium salt of trifluoromethanesulfonyl(4-azapentafluoropyridine)amide (76% yield) were obtained, having a purity determined by a fluorine RMN higher than 99%.

According to the same process, the potassium salt of trifluoromethanesulfonyl((4,6-dinitro-2-trifluoromethyl)phenyl)amide was obtained from 10.82 g of 2-chloro-3,5-dinitrobenzo-trifluoride (40 mmoles, commercially available from Aldrich), having a purity determined by a fluorine, proton and carbon RMN higher than 99%.

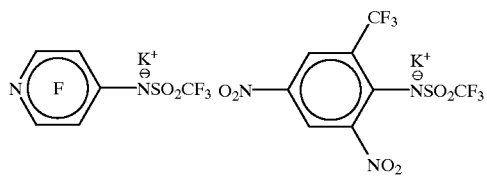

Lithium salts were obtained by ionic exchange with lithium chloride in THF.

These salts are soluble in most of the usual organic solvents (tetrahydrofurane, acetonitrile, dimethylformamide, ethyl acetate, glymes, ...) and in aprotic solvating polymers.

EXAMPLE 59

N,N'-trifluoromethanesulfonyl-3,4-amino-3-cyclobutene-1,2-dione

In a glove box under argon, 5.61 g (30 mmoles) of trifluoromethanesulfonamide in solution in 40 ml of anhydrous tetrahydrofurane at −30° C., there is added drop-wise 30 ml of a 1 M solution of dibutylmagnesium $(C_4H_9)_2Mg$ (30 mmoles, commercially available from Aldrich) in heptane. After 4 hours at −30° C., there is slowly added 2.55 g (15 mmoles) of 3,4-diethoxy-3-cyclobutene-1,2-dione. The reaction was continued during 2 hours at −30° C. and for 24 hours at room temperature. The solvents were then evaporated, the product was reclaimed in water and extracted with ether after acidification of the aqueous solution. The compound obtained after evaporation of ether was sublimated under secondary vacuum at 40° C., and after 24 hours 5.02 g of N,N'-trifluoromethanesulfonyl-3,4-amino-3-cyclobutene-1,2-dione (89% yield) were recovered on a cold finger.

Microanalysis has given: H, 0.78; (0.54); C, 18.89; (19.16); N, 7.04; (7.45); F, 29.88; (30.3); S, 16.71; (17.04).

The lithium salt was obtained by treating the acid with lithium carbonate $Li_2CO_3$ in water.

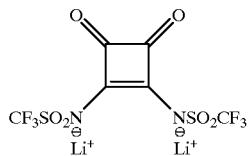

These salts are soluble in most of the usual organic solvents (tetrahydrofurane, acetonitrile, dimethylformamide, ethyl acetate, glymes, . . . ) and in polar polymers.

These salts have two reversible redox couples, they are reoxidized to is neutral state at the potential of oxidation of $LiCoO_2$ at the end of the charge. By dissolution in a liquid, gel or polymer electrolyte, they provide for a protection during overcharge, thus acting as a redox shuttle. They also make it possible to produce electrochrome systems with colorants.

EXAMPLE 60

1,1'-(propylsulfonamide-N-trifluoromethanesulfonyl)ferrocene

During a first step, a ferrocene dilithium complexed with tetramethylethylenediamine (TMEDA) was prepared in the following manner: by operating in a glove box under argon, 37 ml of TMEDA (247 mmoles) freshly distilled and 40 ml of anhydrous hexane were placed in a 1 litre flask. Then, 154 ml of a 1.6 M solution of butyllithium in hexane (247 mmoles, commercially available from Aldrich) were added drop-wise. After 10 minutes, 18.6 g of ferrocene (100 mmoles) in solution in 500 ml of anhydrous hexane were added drop-wise while maintaining a strong stirring of the solution. After standing overnight, orange crystals appeared in the solution, which were recovered by filtration of the solution on a fritted glass of porosity No. 4. After drying under vacuum, there is obtained 28.4 g of 1,1'-dilithio-ferrocene•2 TMEDA (66% yield) which are kept under argon.

8.61 g of this compound (20 mmoles) in 30 ml of anhydrous acetonitrile were thereafter treated with 4.89 g of 1,3-propane sultone (40 mmoles) in a glove box. After 24 hours at room temperature, 2 drops of dimethylformamide were added into the reaction mixture, and 5.08 g of oxalkyl chloride ClCOCOCl (40 mmoles) in solution in 15 ml of anhydrous dichloromethane were added slowly. After 4 hours at room temperature, 14.97 g of the potassium salt of trifluoromethanesulfonamide (80 mmoles) were added. The reaction continued for 24 hours, then the solvent was evaporated. The compound collected was then recrystallized in 30 ml of water containing 3 g of potassium chloride. After filtration and drying, 10.2 g of a di-potassium salt of 1,1'-(propylsulfonamide-N-trifluoromethane-sulfonyl) ferrocene (66% yield) were recovered, in which the purity is characterized by a proton and fluorine RMN higher than 97%.

Microanalysis has given: H, 2.38 (2.62); C, 28.72 (28.13); N, 3.13 (3.64); F, 15.16 (14.83); S, 17.12 (16.68); K, 10.56 (10.17); Fe, 7.65 (7.27).

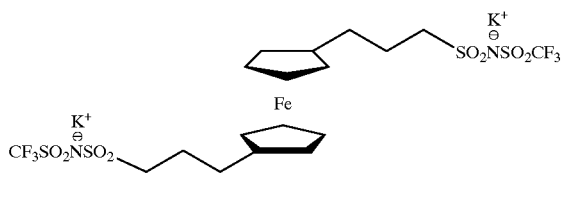

By a similar process, the di-potassium salt of 1,1'-(propylsulfonamide-N-fluorosulfonyl)ferrocene was obtained.

Lithium salts were obtained by treating the acid with lithium carbonate $Li_2CO_3$ in water.

These salts are soluble in most of the usual organic solvents (tetrahydrofurane, acetonitrile, dimethylformamide, ethyl acetate, glymes, . . . ) and in polar polymers.

These salts have a reversible redox couple. In poly (ethylene oxide) a reversible potential ≈3.4 V towards a lithium electrode was determined on a platinum electrode having a diameter of 125 μm.

By dissolution into a liquid, gel or polymer electrolyte, the salts gave protection during overcharge, thus acting as a redox shuttle. They also enable to produce electrochrome systems with colorants.

EXAMPLE 61

9-10-(propylsulfonamide-N-trifluoromethane-sulfonyl) phenazine

By operating in a glove box under argon, there is introduced into a Nalgene 30 ml flask 1.8 g of phenazine (10 mmoles) and 139 mg of metallic lithium. Then, there is added 20 ml of anhydrous tetrahydrofurane and agate balls. After closing the flask, it was rotated upon itself, outside the glove box, on the shaft of a motor. Tetrahydrofurane rapidly turned to a dark purple color, which characterizes monolithium phenazine. After 24 hours, there is obtained in suspension an orange precipitate of 9,10-di-Li-dihydrophenazine. 6.56 g of the potassium salt of trifluoromethanesulfonyl(3-chloropropanesulfonyl)imide (20 mmoles), obtained in Example 8, were then added under argon. The flask was then again rotated upon itself during 24 hours, and the reaction mixture was filtered under argon to remove the precipitate of potassium chloride which is formed during the reaction, and the balls of agate.

After evaporation of the solvent, 6.52 g of the di-lithium salt of 9-10-(propylsulfonamide-N-trifluoromethanesulfonyl)phenazine were recovered.

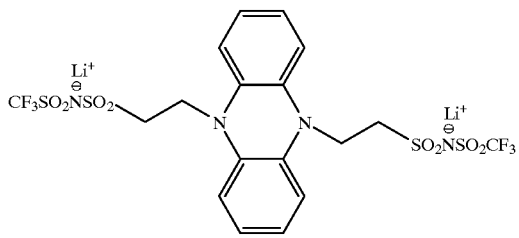

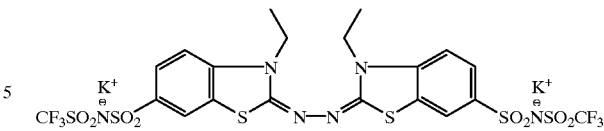

This salt is soluble in most of the usual organic solvents (tetrahydrofurane, acetonitrile, dimethylformamide, ethyl acetate, glymes, . . . ) and in polar polymers.

This salt has two reversible redox couples. In poly (ethylene oxide), on a platinum electrode of a diameter of 125 μm, it was shown that there is a first redox couple having a potential ≈3.2 V and a second redox couple having a potential ≈3.8 V, these potentials being measured towards a lithium electrode.

By dissolution in a liquid, gel or polymer electrolyte, this salt provides protection in overcharge, thus acting as a redox shuttle.

This salt may also be used in electrochrome systems with colorants. It was thus possible to produce an electrochrome glass pane by depositing on a glass plate covered with a conductive layer of ITO (indium and tin oxide), a solution in acetone of this compound and poly(benzodiimide-co-oxide of ethylene) having a molecular weight ≈1,100 g/mole. After evaporation of the solvent and drying, in a glove box, there is deposited on the layer of copolymer, a second glass electrode covered with a conductive layer of ITO (indium and tin oxide). After having sealed the assembly to make it impervious, a potential of 1,250 mV was applied on the outside by means of a potentiostat. The system was then colored in intense blue. By applying a potential of −500 mV, a relatively rapid discoloration of the system (lower than 60 s) was noted.

Such an electrochrome system is easy to prepare, even for large size systems (larger than m$^2$) which use either a glass or a polymer which is suitably treated as a conductive transparent electrode. Moreover, the energy required to maintain the coloration is relatively low, i.e. lower than 1 W/m$^2$.

EXAMPLE 62

2,2'-Azinobis(3-ethylbenzothiazoline-6(sulfonyl (trifluoromethanesulfonyl)imide)

First, the di-sodium salt of 2,2'-azinobis(3-ethylbenzothiazoline-6-sulfonic) acid was prepared from its di-ammonium salt (commercially available from Aldrich), by treating it with a titrated solution of sodium hydroxide. After evaporation and drying, the di-sodium salt was recovered in quantitative yield. To 1.12 g of this compound (2 mmoles) in 10 ml of anhydrous acetonitrile, there is is slowly added 508 mg of oxalkyl chloride ClCOCOCl (4 mmoles) in solution in 1 ml of anhydrous dichloromethane. After 4 hours under stiring, there is added 2.7 g of the potassium salt of perfluoro-1-butanesulfonamide $C_4F_9SO_2NHK$ (4 mmoles). After 48 hours, the acetonitrile was evaporated and the residue was recrystallized in 10 ml of water. After filtration and drying, there is obtained 1.81 g of the following compound:

The di-tetraethylammonium salt was prepared by treating this product with tetraethylammonium chloride in water. The di-tetraethylammonium salt was thereafter recovered by extraction with dichloromethane.

By oxidation, this compound gives a radical and a biradical which are stable zwitterions. In addition, this compound is usefull as oxidation catalyst between an oxygenated aqueous phase and a non-miscible organic phase containing the species to be oxidized.

EXAMPLE 63

Poly(N-2-trifluoromethanesulfonyl-aniline)

To 21.63 g of 1,2-phenylenediamine $C_6H_4(NH_2)_2$ (200 mmoles), in 200 ml of anhydrous dichloromethane at −20° C., there is added drop-wise 56.42 g of tifluoromethanesulfonic anhydride $(CF_3SO_2)_2O$ (200 mmoles) in solution in 50 ml of anhydrous dichloromethane. After standing overnight at −20° C. and 4 hours at room temperature, the dichloromethane was evaporated. The residue was then recrystallized in 10 ml of a 4 M solution of potassium hydroxide KOH. After filtration and drying, 47.87 g of the potassium salt of N-2-trifluoromethanesulfonyl-1,2-phenylenediamine was recovered (86% yield). This compound (172 mmoles) was then stirred in 86 ml of a 2 M solution of hydrochloric acid. After 24 hours, and after filtration and drying, 26.85 g (65% yield) of the ammonium salt of N-2-trifluoromethanesulfonyl-1,2-phenylenediamine $C_6H_4(NSO_2CF_3)(NH_3^+)$ were recovered. 12.01 g of this compound (50 mmoles) were then dissolved in 200 ml of water, 136 mg of silver nitrate (800 μmoles) were added, and the solution was brought to 0° C. A solution of 11.4 g of ammonium persulfate $(NH_4)_2S_2O_8$ (50 mmoles) in 100 ml of water was also prepared and this solution was brought to a temperature of 0° C. Then the persulfate solution was added under stirring for a few minutes to a solution of the aniline salt. After about 10 minutes, the solution is started to assume a color. After 3 hours at a temperature lower than 5° C., the solution was concentrated to a volume ≈100 ml and 3.73 g of potassium chloride were added. The precipitate present in the solution was then recovered by filtration. After drying, 5.9 g of the following black powder was obtained:

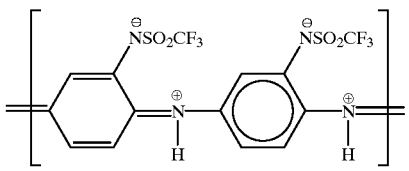

This electronically conductive polymer has an electronic conductivity determined by the method of four peaks of 8.7 S.cm$^{-1}$. This conductivity is stable even when the material is exposed to air.

EXAMPLE 64

1-dodecyl-1,1,1,3,3,3-hexafluoro-2-propanoxysulfonyl(trifluoromethanesulfonyl)imide To 18.11 g (100 mmoles) of 6-bromo-1-hexanol and 11.22 g (100 mmoles) of DABCO in 100 ml of anhydrous THF at −20° C. there is slowly added 19.06 g (100 mmoles) of tosyl chloride. After 24 hours under stirring at −20° C., the reaction mixture was filtered to remove the precipitate of DABCO hydrochloride. After evaporation of the solvent, 6-bromo-1-hexanol tosylate $CH_3\Phi SO_2O(CH_2)_6Br$ was recovered quantitatively. This compound was thereafter dissolved in 200 ml of THF with 40 g of aniline $\Phi NH_2$ and this solution was brought to reflux overnight. After cooling, 300 ml of water were added and the organic phase was extracted with ether. After washing with water, the ether phase was dried with magnesium sulfate. There is obtained, after evaporation and drying, 23 g of N-(6-bromohexyl)aniline.

By operating in a glove box under argon, 18.96 g (50 mmoles) of trifluoromethanesulfonyl(1,1,1,3,3,3-hexafluoro-2-propanoxysulfonyl)imide, prepared as in Example 37, were put in solution in 10 ml of anhydrous tetrahydrofurane. After having brought this solution to −20° C., 50 ml of a 1 M solution in tetrahydrofurane of potassium tert-butoxide $(CH_3)_3COK$ (50 mmoles, commercially available from Aldrich) were slowly added. After 15 minutes, 12.81 g (50 mmoles) of N-(6-bromohexyl)aniline were added. The reaction was continued during 2 hours at −20° C., then for 24 hours at room temperature. After 48 hours under stirring, the solvent was evaporated and the residue was recrystallized in 30 ml of water. After filtration and drying, the potassium salt of 1-(6-anilino-1- hexyl)-1,1,1,3,3,3-hexafluoro-2-propanoxysulfonyl (trifluoromethanesulfonyl)imide was obtained, which has a purity characterized by a proton, carbon and fluorine RMN higher than 97%.

12.13 g of this compound (20 mmoles) were thereafter dissolved in 20 ml of water, 68 mg of silver nitrate (400 μmoles) were added, and the temperature of the solution was brought to 0° C. Also, a solution of 4.56 g of ammonium persulfate $(NH_4)_2S_2O_8$ (20 mmoles) in 100 ml of water was prepared and this solution was brought to 0° C. Then, the solution of persulfate was added during a few minutes to the solution of the salt of aniline under stirring. After about 10 minutes, the solution started to turn to a bluish green color. After 3 hours at a temperature lower than 5° C., the solution was concentrated to a volume 60 ml, and 1.49 g of potassium chloride were added. The precipitate present in the solution was then recovered by filtration. After drying, there is obtained 3.9 g of a black powder of the following compound:

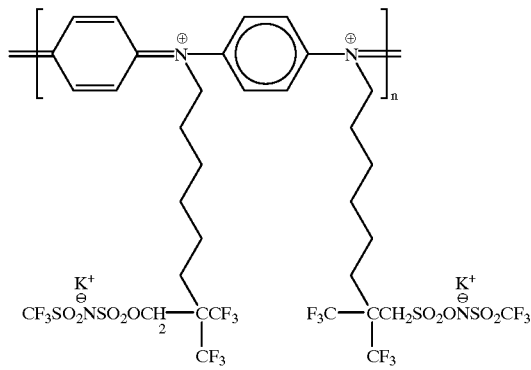

This polymeric compound which comprises a doping anion very delocalized in its structure, has the properties of an electronic conductor (PCE). The low basic character of this anion improves the stability of the polymer, in particular in humid medium. The conductivity determined by a four peaks measurement, before exposing the PCE to a humid atmosphere, was of the order of $4S.cm^{-1}$.

This material was tested as a cathode for a battery. The battery had the following structure:

a composite cathode consisting of 40% by volume of the copolymer obtained in the present example and 60% by volume of poly (ethylene oxide) of molecular weight $3\times10^5$;

an electrolyte consisting of a poly (ethylene oxide) film of molecular weight $5\times10^6$ the lithium salt of trifluoromethanesulfonyl-(butanesulfonyl)imide, obtained in Example 39, at a concentration O/Li=20/1;

a metallic lithium anode.

After mounting the assembly in a button shaped battery casing, the battery obtained was cycled at a temperature of 60° C. between 3 V and 3.9 V. More than 1,000 cycles of charge/discharge were carried out while preserving 80% of the capacity of the first cycle.

In addition, the polymeric compound of the present example is a good corrosion inhibitor of ferrous metals in acid or chloride media. The treatment of surfaces to be protected is simply carried out by depositing a solution of PCE in a mixture of water and dimethylformamide, in the form of a paint, followed by drying and thermal treatment at 100° C. This polymeric compound gives adherent conductive deposits whose conductivity is stable in air on plastics treated by Corona effect.

EXAMPLE 65

Poly(2-[2-(3-thienyl)ethoxy]ethanesulfonyl (trifluoromethanesulfonyl)imide)

By a process similar to the one used for the synthesis of 7,8-octene-3,6-oxa-1-sulfonyl-(trifluoromethanesulfonyl) imide (Example 15), the potassium salt of 2-[2-3(3-thienyl) ethoxy]-ethane-sulfonyl(trifluoromethanesulfonyl)imide was synthesized from 2-(3-thienyl)ethanol. The product obtained has a purity determined by a carbon and proton RMN higher than 98%.

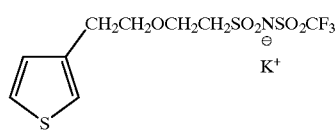

10 ml of a $5\times10^{-2}$ M solution of the salt in acetonitrile was prepared and electropolymerization was carried out in the anode compartment of an electrochemical cell on an electrode of platinum. There is obtained a conductive flexible film of:

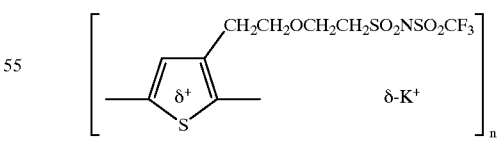

in which the doping (oxidation) is ensured by cation and electron exchange with the exterior. The conductivity of this material is of the order of 10 $S.cm^{-1}$ and it is stable at ambient atmosphere and in humid medium. An electropolymerization carried out in the presence of non-substituted pyrrol or having oxyethylene chains in N or 3 position gives copolymers which are also stable in which the change of color may be used for preparing electrochrome system.

EXAMPLE 66

Doped Polyaniline

In 100 ml of water there is suspended 2.54 g of polyaniline chloride (AC&T, St Égrève, France):

To 9.81 g of the potassium salt of trifluoromethanesulfonyl(di-2-ethylhexylaminosulfonyl) imide obtained in Example 28 were then added:

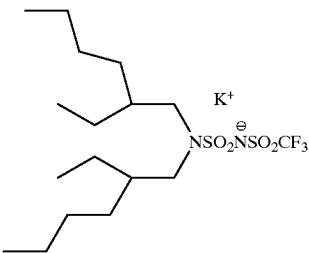

After 48 hours under stifling, the polyaniline doped with trifluoromethanesulfonyl)di-2-ethylhexylaminosulfonyl) imide was recovered. In this form, it is soluble in toluene. A toluene solution of the doped polyaniline was used to produce a film which is an electronically conductive polymer in which the conductivity, measured by the method the four peaks, is 6 S/cm, with a good stability in humid medium.

From this solution, there is also prepared a film on a support of polypropylene (PP) treated by Corona effect. After drying under vacuum at 60° C. during 48 hours, there is obtained a deposit of polyaniline which is conductive and adherent and has a thickness lower than 1 micron. This type of treatment on plastic materials is particularly interesting to produce flexible electrical contactors or systems of electromagnetic protections.

EXAMPLE 67

Poly(4-styrenesulfonyl (trifluroro methane sulfonyl) imide)

20.62 g of poly(sodium-4-styrenesulfonate) having an average molecular weight of $10^6$ g/mole (100 mmoles of $-SO_3Na$), (commercially available from Aldrich) in suspension in 100 ml of anhydrous dimethylformamide were treated with 14.08 g (110 mmoles) of (chloromethylene) dimethylammonium chloride (commercially available from Aldrich) at room temperature. After 72 hours, the solution became viscous, and the poly(4-styrenesulfonyl chloride) goes into solution in dimethylformamide. To the reaction mixture there is then added 16.4 g (110 mmoles) of trifluoromethanesulfonamide and 24.68 g (220 mmoles) of 1 (DABCO). After 24 hours, the solvent was evaporated, the product obtained was reclaimed in 50 ml of water, and treated with 8.2 g of anhydrous potassium chloride. After 24 hours, the reaction mixture was filtered and the product thus recovered was recrystallized in 50 ml of water. After drying, there is obtained 26.1 g of the potassium salt of poly(4-styrenesulfonyl(trifluoromethanesulfonyl)-imide) (74% yield) having a purity characterized by a proton and fluorine RMN higher than 99%.

The corresponding lithium salt was prepared quantitatively by ionic exchange (metathesis) between the potassium salt and lithium chloride in anhydrous tetrahydrofurane.

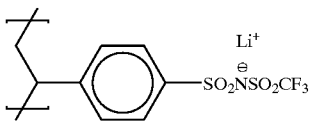

This polyelectrolyte is soluble in most of the usual organic solvents (tetrahydrofurane, acetonitrile, dimethylformamide, ethyl acetate, glymes) and in polar polymers.

By utilizing an appropriate cation, this polyelectrolyte may constitute a doping agent of conjugated electronically conductive polymers such as polypyrrol or polyaniline.

EXAMPLE 68

Catalysis of an Aidol Condensation

Diethylaminosulfonyl(trifluoromethanesulfonyl)imide was prepared from its potassium salt, obtained in Example 28, according to a process similar to the one used in Example 29 to give dimethylaminosulfonyl (trifluoromethanesulfonyl)imide. Following this, 2.84 g of this acid (10 mmoles) were treated with 657 mg of ytterbium oxide $Yb_2O_3$ (1.67 mmoles) in 20 ml of water. After 24 hours of sttirring, the solution was lyophilized, and the product obtained was dried under vacuum during 48 hours at 60° C. The ytterbium salt of diethylaminosulfonyl (trifluoromethanesulfonyl)imide ($Yb(DETFSI)_3$) was obtained in quantitative yield.

This salt was used as a catalyst for an aldol condensation in the following manner:

To 410 mg of $Yb(DETFSI)_3$ (0.4 mmoles, 10% molar) in dichloromethane there is added a mixture of 1.05 g (6 mmoles) of 1-ene-3-methyl-1-silylacetal-1-methoxypropene $(CH_3)_2C=C(OSiMe_3)OMe$ and 420 mg (4 mmoles) of benzaldehyde in 10 ml of dichloromethane. After 16 hours under stirring at room temperature, water was added and the product was extracted with dichloromethane. The organic phase was washed with three fractions of 100 ml of water, and dichloromethane was evaporated. The residue was then treated with a mixture tetrahydrofurane/HCl 1 M (20:1) during 0.5 hours at 0° C. After diluting with hexane, a saturated solution of sodium bicarbonate was added, and the product was extracted with dichloromethane. The organic phase was washed with a saturated solution of sodium chloride, and dried with sodium sulfate. After evaporation of the solvents, the raw product was chromatographed on a silica gel. Methyl-3-hydroxy-2,2-dimethylphenylpropionate was obtained with a yield of 89%.

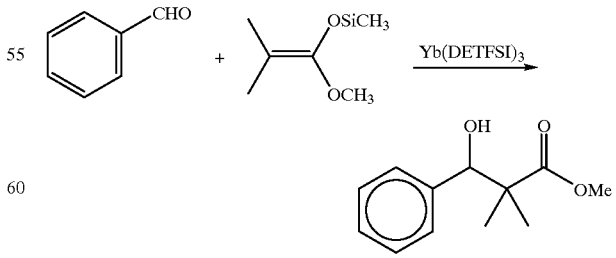

The same reaction was carried out with a quantity of catalysts which is decreased by a factor near 10, without decreasing the yield of the compound methyl-3-hydroxy-2, 2-dimethyl-phenylpropionate. This result is due to the good solubility in dichloromethane of the ytterbium salt of diethylaminosulfonyl(trifluoromethanesulfonyl)imide.

EXAMPLE 69

Catalysis of a Michael Addition

The ytterbium salt of diethylaminosulfonyl (trifluoromethanesulfonyl)imide, obtained in Example 40, was used as a catalyst in a Michael addition in the following manner: To 410 mg of Yb(DETFSI)$_3$ (0.4 mmoles, 10% molar), obtained in Example 65 in 15 ml of dichloromethane, there is added a mixture of 1.05 g of 1-ene-2-methyl-1-silylacetal-1-methoxypropane (CH$_3$)$_2$C=C(OSiMe$_3$)OMe (6 mmoles) and 840 mg of chalcone (4 mmoles) in 10 ml of dichloromethane. After 12 hours under stirring, water is added and the product was extracted with dichloromethane. The organic phase was washed with three fractions of 100 ml of water, and dichloromethane was evaporated. The residue was then treated with a mixture of tetrahydrofurane/HCl 1 M (20:1) during 0.5 hours at 0° C. After diluting with hexane, there is added a saturated solution of sodium bicarbonate, the product was extracted with dichloromethane. The organic phase was washed with a saturated solution of sodium chloride, and dried with sodium sulfate. After evaporation of the solvents, the raw product was chromatographed on a silica gel. The compound 1,5-dicarbonyl was obtained with a yield of 87%.

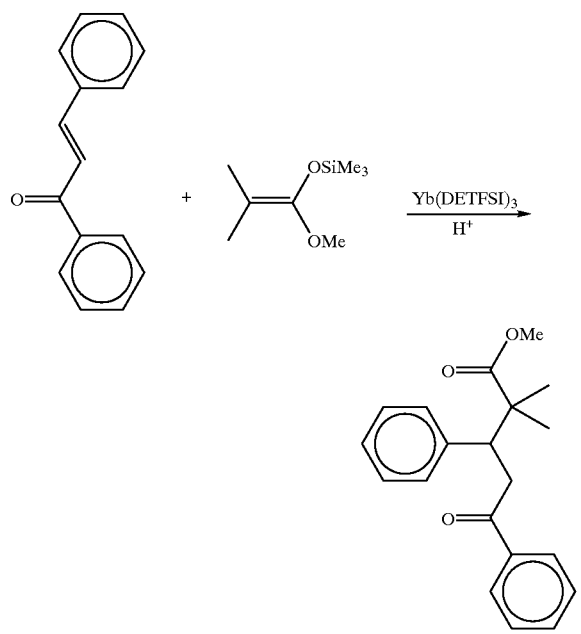

The same reaction was carried out with a quantity of catalyst which is decreased by a factor close to 10, without decreasing the yield of the 1,5-dicarbonyl compound. This result is due to the good solubility in dichloromethane of the ytterbium salt of diethylaminosulfonyl (trifluoromethanesulfonyl)imide.

EXAMPLE 70

Catalysis of a Friedel-Crafts Acylation Reaction

To 10 ml of a 1 M solution of triethylaluminum (C$_2$H$_5$)$_3$Al (10 mmoles) (commercially available from Aldrich in toluene, there is slowly added under argon 2.84 g of trifluoromethanesulfonyl(diethylaminosulfonyl)imide (C$_2$H$_5$)$_2$NSO$_2$NHSO$_2$CF$_3$ (10 mmoles) in solution in 10 ml of toluene, hereinafter designated HDETFSI, previously prepared from the corresponding potassium salt by extraction with ether. After 2 hours under stirring, the solvent was evaporated and the corresponding aluminum salt was dried and stored in a glove box.

This compound was used as catalyst for a Friedel-Crafts acylation reaction in the following manner; in 40 ml of anhydrous nitromethane, there is added 616 mg of Al(DETFSI)$_3$ (700 μmoles), and 1.08 g of anisol (10 mmoles) and 2.04 g of acetic anhydride. After stirring for 5 minutes at 21° C., the reaction nmixture was diluted with 50 ml of ether and the reaction was inhibited with 100 ml of a saturated solution of sodium bicarbonate NaHCO$_3$. After filtration on Celite, the solution was extracted with three fractions of 50 ml of ether, and the ether phase which was collected was washed with a saturated solution of potassium chloride. After drying the ether phase with magnesium sulfate and evaporation, 1.46 g of p-methoxyacetophenone (97% yield) were recovered with a purity characterized by a proton RMN higher than 99%.

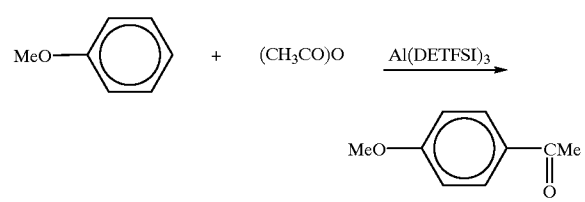

EXAMPLE 71

Catalysis of a Diels & Alder Reaction

Various salts according to the invention were used as catalysts of a Diels Alder reaction, namely the reaction of methylvinylketone with cyclopentadiene.

The salts used are the lanthanum salt of trifluoromethanesulfonyl(R(-)-1-phenyl-2,2,-trifluoroethanoxysulfonyl)imide (LAPTETFSI) prepared according to Example 46, the lanthanum salt of (1R)-(-)-10-camphorsulfonyl)perfluorobutanesulfonyl)imide (LaCSTFSI) prepared according to Example 48, the lanthanum salt of (1R)-(-)-trifluoromethanesulfonyl(N-methoxybutyl-N- 2-butyl-3-methyl)aminosulfonyl)imide (LaMBBMTFSI) prepared according to Example 47 and the scandium salt of trifluoromethanesulfonyl (N-(1S)-(+)-ketopinic-acetyl-N-methylsulfonyl)imide (ScKANTFSI) prepared according to Example 49.

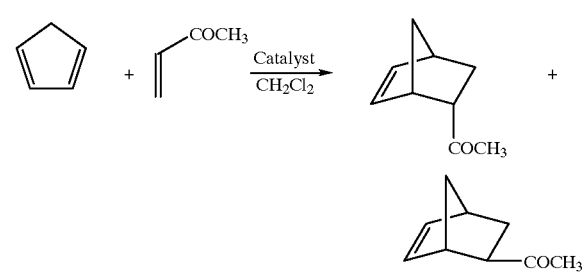

For each of the above salt, the following process was used.

To a solution of 651 mg of freshly distilled cyclopentadiene (10 mmoles) and 701 mg of methylvinylketone in 10 ml of dichloromethane, there are added 200 μmoles of the lanthanum or scandium salt of chiral. After 24 hours at room temperature, the reaction mixture was filtered to remove the catalyst in suspension. In all cases, there is obtained a yield, determined by chromatography in gaseous phase, higher than 90%. After separating the different reaction products on a chiral column, the enantiomeric excesses were determined by RMN. These salts enable to obtain a chiral catalysis which is made obvious by the enantiomeric excesses given in the following table.

| Chiral Catalyst | Enantiomeric Excesses |
|---|---|
| LaPTETFSI | 69% |
| LaCSTFSI | 76% |
| LaMBBMTFSI | 72% |
| ScKANTFSI | 67% |

EXAMPLE 72

Acrylonitrile/4styrenesulfonyl (trifluoromethanesulfonyl)imide copolymer

A solution of 19.27 g of the lithium salt of 4-styrenesulfonyl(trifluoromethanesulfonyl)imide (60 mmoles), 2.12 g (40 mmoles) of acrylonitrile and 100 mg of 1,1'-azobis)cyclohexanecarbonitrile) (1 mmoles) in 100 ml of anhydrous tetrahydrofurane was degassed by flushing with dry argol Then, under argon, copolymerization of acrylonitrile with the styrene derivative was carried out by heating the reaction mixture at 60° C. during 48 hours. After cooling, the solution was concentrated, and the polymer was recovered by reprecipitation in ether. After filtration and drying, 17.54 g of the lithium salt of poly(acrylonitrile-co-4-styrenesulfonyl-(trifluoromethanesulfonyl)imide (PANSDTFSI) were recovered with a yield of 82%.

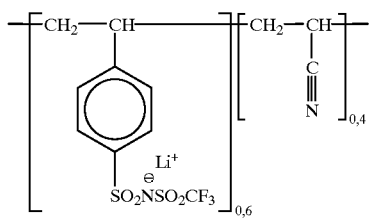

This polymer may be used for preparing gelled polymer electrolytes with fixed anions, the polymer ensuring a double matrix functionality enabling to obtain the polyelectrolyte gel.

A gel electrolyte consisting of 30 weight per cent of polyelectrolyte, 35% of ethylene carbonate and 35% of propylene carbonate was prepared. This gel has good mechanical properties and a conductivity of $9.6 \times 10^{-4}$ S.cm$^{-1}$ at 30° C. The number of cationic transport in this electrolyte is 0.85. An electrochemical generator was prepared comprising an anode consisting of coke carbon (80% in volume) mixed with the copolymer (PANSDTFSI) as binder (20% by volume), the above gelled electrolyte, and a composite cathode consisting of carbon black (6% by volume), $LiNiO_2$ (75% by volume) and the copolymer (PANSDTFSI) (20% by volume). This generator has good performances in cycling at 25° C. (1,000 cycles of charge/discharge between 3 and 4.2 V by maintaining a capacity higher than 80% of the capacity during the first cycle). Also, it has very good performances during calls for power due to the fact of the utilization of fixed anions. The utilization of fixed anions has also enabled to improve the evolution of the resistance of the interface.

EXAMPLE 73

Acrylonitrile/4-styrenesulfonyl (trifluoromethanesulfonyl)imide copolymer

According to a process similar to the one used in Example 72, a copolymer of acrylonitrile (3% molar) and of the lithium salt of 4-styrenesulfonyl(trifluoromethanesulfonyl)-imide (97% molar) was synthesized.

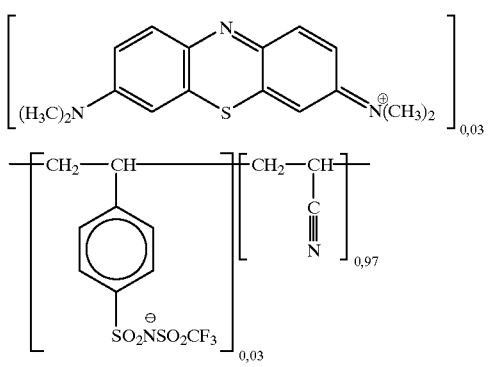

This copolymer has antistatic properties, contrary to polyacrylonitrile (PAN) which, in the form of alkaline or ammonium salt, is widely used in the form of textile fibre. Moreover, spinning of this copolymer is easier than with non-modified PAN.

The copolymer has very good interaction with cationic coloring matters such as methylene blue, which makes it a material of interest for colored textile fibres, the stability of the color being clearly improved with respect to the known copolymer of acrylonitrile and methalkylsulfonate.

EXAMPLE 74

Vinylidene fluoride/2,2-fluorovinylsulfonyl-(trifluoromethanesulfonyl)imide copolymer In a chemical reactor, there is introduced a solution of 8.43 g (30 mmoles) of 2,2-fluorovinylsulfonyl (trifluoromethanesulfonyl)imide obtained in Example 24 and 100 mg of 1,1'-azobis(cyclohexane-carbonitrile) in 100 ml of anhydrous tetrahydrofurane. After flushing the reactor under argon, there is introduced with a sieve, 4.48 g of vinylidene fluoride $CF_2CH_2$ (70 mmoles, commercially available from Air Liquide). Copolymerization was then carried out under argon by heating the reaction mixture at 60° C. during 48 hours. After cooling, the solution was concentrated, and the polymer was recovered by reprecipitation in ether. After filtration and drying, 10.2 g of the lithium salt of poly(vinylidenefluoride-co-2,2-ethanesulfonyl(trifluoromethane-sulfonyl)imide (PFVESTFSI) were recovered with a yield of 79%.

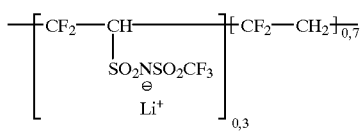

This polymer enables production of gelled polymer electrolytes with fixed anions, the polymer ensuring a double functionality of matrix enabling to obtain the gel of polyelectrolytes.

There is prepared a battery of the same type as the one described in Example 72 and analogous performances were obtained.

EXAMPLE 75

AGE/Epoxy-half TFSI/OE Copolymer

In a chemical reactor, there is introduced a solution of 15.37 g (50 mmoles) of the potassium salt of 3,4-epoxybutane-1-sulfonyl(trifluoromethanesulfonyl)imide, prepared as in Example 13, and 685 mg (6 mmoles) of alkylglycidylether in 100 ml of anhydrous tetrahydrofurane. After flushing the reactor with argon, there are introduced with a sieve 6.34 g (146 mmoles) of 1,2-epoxide in 100 $\mu$l of a $10^{-2}$ M solution of potassium t-butoxide in THF. Polymerization was then carried out under argon by heating the reaction mixture at 60° C. during 48 hours. After cooling, the solution was concentrated, and the polymer was recovered by reprecipitation in ether. After filtration and drying, 15.9 g (71% yield) of the potassium salt of poly(oxyethylene-co-3,4-epoxybutanesulfonyl-(trifluoromethanesulfonyl)imide-co-alkylglycidyl-ether) were recovered.

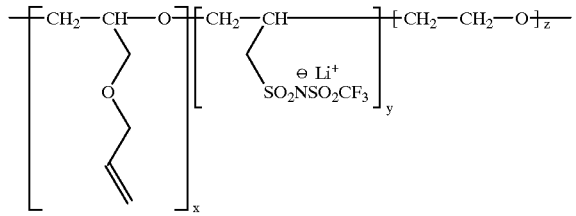

This polymer enables to prepare gelled polymer electrolytes with fixed anions, the polymer ensuring a double matrix functionality enabling to obtain the gel of polyelectrolytes. It may be crosslinked during the process of preparing an electrochemical system containing same.

With this polyelectrolyte, a battery similar to the one described in Example 22 was prepared, which has given similar performances.

EXAMPLE 76

Polysiloxane with Fixed Anions

In a three-neck flask provided with a cooler, a mechanical stirrer and a neutral gas inlet (Argon), 9.5 g of a copolymer of dimethylsiloxane and (hydrogeno) (methyl)-siloxane (HMS 301 25% SiH, $M_W$ 1900 Gelest Inc., Tullytown, Pa., USA) were placed in solution in tetrahydrofurane; 9.13 g of the lithium salt of vinylsulfonyl(trifluoromethanesulfonyl)imide and 70 mg of chloroplatinic acid $H_2PtCl_6$. were then added. The mixture was heated to reflux during 4 hours. The polymer was then reprecipitated in ethanol.

A copolymer of dimethylsiloxane and of the lithium salt of (N-trifluoromethanesulfonyl-ethylsulfonamide) (methyl)-siloxane was thus obtained.

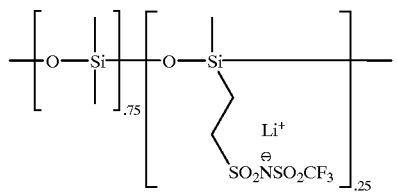

This polymer is soluble in most of the organic solvents, including in amounts >2% in oils or silicon materials, thus giving them antistatic properties.

EXAMPLE 77

Li/POENV$_2$O$_5$ Battery

The lithium salt of dimethylaminosulfonyl-(trifluoromethanesulfonyl)imide, prepared according to Example 25, was tested in an electrochemical generator according to the lithium-polymer technology. The generator was prepared by superposing the following layers:

a stainless steel current collector having a thickness of 2 mm;

a cathode consisting of a button shaped film of composite material having a thickness of 89 $\mu$m and consisting of vanadium dioxide (45% by volume), Shawinigan black (5% by volume) and a polyethylene oxide of molecular weight Mw=3.10$^5$ (50% by volume);

an electrolyte consisting of a button shaped film of polyethylene oxide of molecular weight Mw=5.10$^6$ containing the lithium salt of dimethylamino-sulfonyl (trifluoromethanesulfonyl)imide at a concentration O/Li=15/1;

an anode consisting of a sheet of metallic lithium having a thickness of 50 $\mu$m;

a current collector similar to the above mentioned collector.

The button shaped members constituting the electrodes and the electrolyte were cut in a glove box and piled in the order indicated above. The collectors were then placed on both sides of the pile obtained.

The assembly was sealed in a button shaped battery casing, which simultaneously enables to protect the generator from the atmosphere and to exercise a mechanical stress on the films. The battery was then placed in an enclosure under argon mounted in a dryer at a temperature of 60° C. It was then cycled between 1.8 and 3.3 V at a rate of charge and discharge of C/10 (charged or discharged nominal capacity in 10 hours).

The cycling curve is given in FIG. 1. In this figure, the use, U, expressed in % is given in ordinate, and the number of cycles C is given in abscissae.

EXAMPLE 78

Extrusion

In a Warner & Pfilder extruder, there is introduced under an argon atmosphere, poly (ethylene oxide) of a molecular weight $M_W$=10$^5$ in the form of button shaped members 2 mm in diameter and a mixture of the lithium salt of dodecylsulfonyl(trifluoromethanesulfonyl)imide prepared according to a process analogous to the one of Example 39, the potassium salt of Igepal® CA-520-propylsulfonyl (trifluoromethanesulfonyl)imide prepared by a process analogous to the one of Example 43, vanadium oxide $V_2O_5$ crushed to a particle size smaller than 5 µm, and carbon black. The mixture of components was then introduced in such proportions that vanadium oxide represents 40% of the total volume, Shawinigan black 5%, the potassium salt of Igepal® CA-520-propylsulfonyl(trifluoromethanesulfonyl) imide 2%, and the mixture poly (ethylene oxide)/lithium salt of dedecylsulfonyl(trifluoromethanesulfonyl)imide 53%, the lithium salt being at a concentration O/Li=15/1. The mixture was then extruded at a temperature of 100° C. in the form of a band 14 cm wide and a thickness of 63 µm. This film which can be used as cathode, was directly placed on a sheet of stainless steel 8 µm thick.

This film of composite cathode was itself covered with a filn of electrolyte 30 µm thick obtained by extrusion of a mixture of poly (ethylene oxide) of molecular weight $M_W=3.10^5$ and a lithium salt of dodecylsulfonyl (trifluoromethanesulfonyl)imide at a concentration O/Li= 45/1.

The mixture was then laminated with a film of lithium 20 µm thick. There is thus obtained an electrochemical generator according to the lithium-polymer technology.

Figure 2:
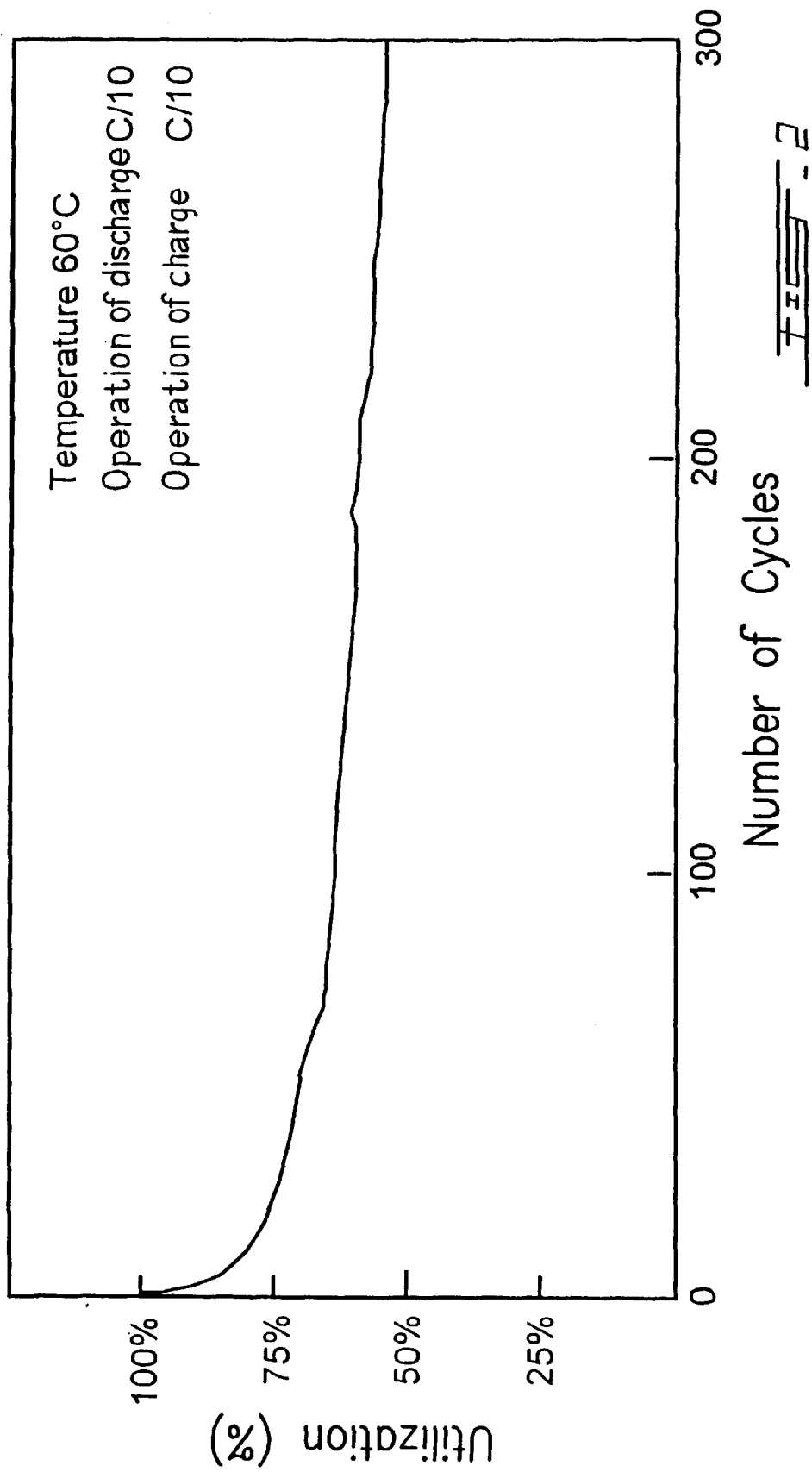

The cycling curve of this generator at a rate of charge and discharge iblx of C/10 is represented in FIG. 2. In this figure, the use, U, expressed in % is given in ordinate, and the number of cycles C is given is abscissae.

The salts of the present invention contain long alkyl chains such as the potassium salt of Igepal® CA-520-propylsulfonyl(trifluoromethanesulfonyl)imide or the lithium salt of dedecylsulfonyl(trifluoromethanesulfonyl) imide, enabling to plasticize poly (ethylene oxide). They also facilitate the extrusion of films of cathodes or electrolytes used during the manufacture of batteries according to the technology of lithium-polymer in thin film. Their electrochemical stability also enables to obtain good performances during the cycling of these batteries.

What is claimed is:

1. Electrochemical generator comprising a negative electrode and a positive electrode both separated by an electrolyte, characterized in that the electrolyte is a material comprising an ionic compound in a solvent, wherein said ionic compound consists of an amide or salts thereof, comprising an anionic part associated with at least one cationic part $M^{+m}$ in sufficient number to ensure an electronic neutrality thereto, characterized in that M is a hydroxonium, a nitrosonium $NO^+$, an amionium $—NH_4^+$, a metallic cation having a valency m, an organic onium cation having a valency m or an organo-metallic cation having a valency m and in that the anionic part corresponds to the formula $R_F$—$SO_X$—$N^-$—$Z$ in which:

the group —$S(O)_X$— represents a sulfonic group —$SO_2$— or a sulfinyl group —SO—;

$R_F$ is a halogen or a perhalogenated alkyl, alkylaryl, oxa-alkyl, aza-alkyl or thia-alkyl radical, or a radical corresponding to one of the formulae $R_ACF_2$—, $R_ACF_2CF_2$—, $R_ACF_2CF(CF_3)$— or $CF_3C(R_A)F$— in which $R_A$— represents a non-perhalogenated organic radical;

Z represents an electro-attractor radical having a Hammett parameter at least equal to that of a phenyl radical, selected from:

j) —CN, —$NO_2$, —SCN, —$N_3$, —$CF_3$, R'$_F$$CH_2$—(R'$_F$ being a perfluorinated radical) or a fluoroalkylthioxy radical, jj) radicals comprising one or more aromatic nuclei optionally containing at least one hydrogen, oxygen, sulfur or phosphorus atom, said nuclei optionally being condensed nuclei and/or said nuclei optionally carrying at least one substituent selected from halogens, —CN, —$NO_2$, —SCN, —$N_3$, —$CF_3$, $CF_3CH_2$—, $CF_2$=CF—O—, $CF_2$=CF—S—, perfluoroalkyl groups, fluoroalkyloxy groups, fluoroalkylthioxy groups, alkyl, alkenyl, oxa-alkyl, oxa-alkenyl, aza-alkyl, aza-alkenyl, thia-alkyl, thia-alkenyl radicals, polymer radicals, radicals having at least one cationic ionophoric group and/or at least one anionic ionophoric group;

with the proviso that a substituent Z may be a monovalent radical, part of a multivalent radical carrying a plurality of groups $R_F$—$S(O)_X$—N—, or a polymer segment; or Z is a radical $R_D$—Y— in which Y is a sulfonyl, sulfinyl or phosphonyl group and $R_D$ is a radical selected from the group consisting of:

a) alkyl or alkenyl radicals, aryl, arylalkyl, alkylaryl or alkenylaryl radicals, alicyclic, heterocyclic radicals, or polycyclic radicals;

b) alkyl or alkenyl radicals comprising at least one functional ether, thioether, amine, imine, carboxyl, carbonyl, hydroxy, silyl, isocyanate or thioisocyanate group;

c) aryl, arylalkyl, arylalkenyl, alkylaryl or alkenylaryl radicals, in which the aromatic nuclei and/or at least one substituent of the nucleus comprises heteroatoms selected from nitrogen, oxygen, sulfur;

d) radicals comprising condensed aromatic cycles which optionally comprise at least one heteroatom selected from nitrogen, oxygen, sulfur;

e) halogenated alkyl, alkenyl, aryl, arylalkyl, alkylaryl or alkenylaryl radicals in which the number of carbon atoms carrying at least one halogen is at most equal to the number of non-halogenated carbon atoms, the carbon in α position of group Y not being halogenated when Y is —$SO_2$—, said radicals optionally comprising functional ether, thioether, amine, imine, carboxyl, carbonyl, hydroxy, silyl, isocyanate or thioisocyanate groups;

f) radicals $R_CC(R')(R")$—O— in which $R_C$ is an alkyl perfluorinated radical and R' and R" are independently from one another, an hydrogen atom or a radical as defined in a), b), c) or d) above;

g) radicals $(R_B)_2N$—, in which the $R_B$, identical or different, as defined in a), b), c), d) and e) above, one of the $R_B$ may be a hydrogen atom, or the two radicals $R_B$ together form a bivalent radical which forms a cycle with N;

h) radicals consisting of a polymer chain;

i) radicals having one or more cationic ionophoric groups and/or one or more anionic ionophoric groups;

with the proviso that a substituent $R_D$ may be a monovalent radical, part of a multivalent radical carrying a plurality of groups $R_FS(O)_X$—N—Y—, or a segment of a polymer;

with the proviso that, when Y is a sulfonyl and $R_D$ is a radical such as defined in a), $R_F$ is $R_ACF_2$—, $R_ACF_2CF_2$—, $R_ACF_2CF(CF_3)$—, $CF_3C(R_A)F$— or a perhaloalkyl radical having 1 to 2 carbon atoms.

2. Generator according to claim 1, characterized in that the negative electrode consists of metallic lithium, or an alloy thereof, optionally in the form of nanometric dispersion in lithium oxide, or a double nitride of lithium and a transition metal, or an oxide with low potential having the general formula $Li_{1+y+x/3}Ti_{2-x/3}O_4$ ($0 \leq x \leq 1$, $0 \leq y \leq 1$), or carbon and carbon products originating from pyrolysis of organic materials.

3. Generator according to claim 1, characterized in that the positive electrode is selected from vanadium oxides $VO_x$ ($2 \leq x \leq 2.5$), $LiV_3O_8$, $Li_yNi_{1-x}Co_xO_2$, ($0 \leq x \leq 1$; $0 \leq y \leq 1$), spinels of manganese $Li_yMn_{1-x}M_xO_2$ (M=Cr, Al, V, Ni, $0 \leq x \leq 0,5$; $0 \leq y \leq 2$), organic polydisulfides FeS, $FeS_2$, iron sulfate $Fe_2(SO_4)_3$, phosphates and phophosilicates of iron and lithium of olivine structure, or substituted products where iron is substituted by manganese, used alone or in admixtures.

4. Generator according to claim 1, characterized in that the collector of the cathode is made of aluminum.

5. An ionically conducting material according to claim 1, characterized in that the cation M is a metallic cation selected from the group consisting of cations of alkali metals, cations of alkali-earth metals, cations of transiton metals, cations of trivalent metals, cations of rare earth metals and organometallic cations.

6. An tonically conducting material according to claim 1, characterized in that $R_F$ is a fluorine atom or a perhalogenated alkyl radical having 1 to 12 carhon atoms, or a perhalogenated alkylaryl radical having 6 to 9 carbon atoms.

7. An tonically conducting material according to claim 1, characterized in that $R_D$ is sclocted from alkyl, alkenyl, oxa-alkyl, oxa-alkenyl, aza-alkyl, aza-alkenyl, thia-alkyl or thia-alkenyl radicals having 1 to 24 carbon atoms, or from aryl arylalkyl, alkylaryl or alkenylaryl radicals having 5 to 24 carbon atoms in which the lateral chains and/or the aromatic nuclei comprise heteroatoms.

8. An ionically conducting material according to claim 1, characterized in that $R_D$ is selected from alkyl or alkenyl radicals having 1 to 12 carbon atoms and optionally comprising at least one heterostom O, N or S in the main chain or in a lateral chain, and/or optionally carrying a hydroxy group, a carbonyl group, an aminc group, a carboxyl group, an isocyanate group or a thloisocyanate group.

9. An ionically conducting material according to claim 1, characterized in that $R_D$ is part of a poly(oxyalkylene) radical or a polystyrene radical.

10. An ionically conducting maerial according to claim 1, characterized in that the solvent is either an aprotic liquid solvent, selected from linear others and cyclic ethers, esters, nitriles, nitro derivatives, amides, sulfones, sulfolanes, alkylsulfamides and partially halogenated hydrocarbons, or a polar polymer, or a mixture thereof.

11. A supercapacitor using at least one carbon electrode with high specific surface, or at least an electrode containing a redox polymer, with an electrolyte material, in which the electrolyte is a material comprising an ionic compound in a solvent, wherein said ionic compound consists of an amide or salts thereof, comprising an anionic part associated with at least one cationic part $M^{+m}$ in sufficient number to ensure an electronic neutrality thereto, characterized in that M is a hydroxonium, a nitrosonium $NO^+$, an ammonium $—NH_4^+$, a metallic cation having a valency m, an organic onium cation having a valency m or an organo-metallic cation having a valency m and in that the anionic part corresponds to the formula $R_F—SO_X—N^-—Z$ in which:

the group $—S(O)_X—$ represents a sulfonic group $—SO_2—$ or a sulfinyl group $—SO—$;

$R_F$ is a halogen or a perhalogenated alkyl, alkylaryl, oxa-alkyl, aza-alkyl or thia-alkyl radical, or a radical corresponding to one of the formulae $R_ACF_2—$, $R_ACF_2CF_2—$, $R_ACF_2CF(CF_3)—$ or $CF_3C(R_A)F—$ in which $R_A—$ represents a non-perhalogenated organic radical;

Z represents an electro-attractor radical having a Hammett parameter at least equal to that of a phenyl radical, selected from:

j) $—CN$, $—NO_2$, $—SCN$, $—N_3$, $—CF_3$, $R'_F CH_2—$ ($R'_F$ being a perfluorinated radical) or a fluoroalkylthioxy radical, jj) radicals comprising one or more aromatic nuclei optionally containing at least one hydrogen, oxygen, sulfur or phosphorus atom, said nuclei optionally being condensed nuclei and/or said nuclei optionally carrying at least one substituent selected from halogens, $—CN$, $—NO_2$, $—SCN$, $—N_3$, $—CF_3$, $CF_3CH_2—$, $CF_2=CF—O—$, $CF_2=CF—S—$, perfluoroalkyl groups, fluoroalkyloxy groups, fluoroalfylthioxy groups, alkyl alkenyl oxa-alkyl, oxa-alkenyl, aza-alkyl, aza-alkenyl, thia-alkyl, thia-alkenyl radicals, polymer radicals, radicals having at least one cationic ionophoric group and/or at least one anionic ionophoric group;

with the proviso that a substituent Z may be a monovalent radical, part of a multivalent radical carrying a plurality of groups $R_F—S(O)_X—N—$, or a polymer segment; or Z is a radical $R_D—Y—$ in which Y is a sulfonyl, sulfinyl or phosphonyl group and $R_D$ is a radical selected from the group consisting of:

a) alkyl or alkenyl radicals, aryl, arylalkyl, alkylaryl or alkenylaryl radicals, alicyclic, heterocyclic radicals, or polycyclic radicals;

b) alkyl or alkenyl radicals comprising at least one functional ether, thioether, amine, imine, carboxyl, carbonyl, hydroxy, silyl, isocyanate or thioisocyanate group;

c) aryl, arylalkyl, arylalkenyl, alkylaryl or alkenylaryl radicals, in which the aromatic nuclei and/or at least one substituent of the nucleus comprises heteroatoms selected from nitrogen, oxygen, sulfur;

d) radicals comprising condensed aromatic cycles which optionally comprise at least one heteroatom selected from nitrogen, oxygen, sulfur, e) halogenated alkyl, alkenyl, aryl, arylalkyl, alkylaryl or alkenylaryl radicals in which the number of carbon atoms carrying at least one halogen is at most equal to the number of non-halogenated carbon atoms, the carbon in α position of group Y not being halogenatod when Y is $—SO_2—$, said radicals optionally comprising functional ether, thioether, amine, imine, carboxyl, carbonyl, hydroxy, silyl, isocyanate or thioisocyanate groups;

f) radicals $R_CC(R')(R")—O—$ in which $R_C$ is an alkyl perfluorinated radical and R' and R" are independently from one another, an hydrogen atom or a radical as defined in a), b), c) or d) above;

g) radicals $(R_B)_2N—$, in which the $R_B$, identical or different, as defined in a), b), c), d) and a) above, one of the $R_B$ may be a hydrogen atom, or the two radicals $R_B$ together form a bivalent radical which forms a cycle with N;

h) radicals consisting of a polymer chain;

i) radicals having one or more catonic ionophoric groups and/or one or more anionic ionophoric groups;

with the proviso that a substituent $R_D$ may be a monovalent radical, part of a multivalent radical carrying a plurality of groups $R_F$—S(O)x—N—Y—, or a segment of a polymer;

with the proviso that, when Y is a sulfonyl and $R_D$ is a radical such as defined in a), $R_F$ is $R_ACF_2$—, $R_ACF_2CF_2$—, $R_ACF_2CF(CF_3)$—, $CF_3C(R_A)F$— or a perhaloalkyl radical having 1 to 2 carbon atoms.

12. An ionically conducting material according to claim 11, characterized in that M is an organic onium cation selected from the group consisting of $R_3O^+$(oxonium), $NR_4^+$ (ammonium), $RC(NHR_2)_2^+$(amidinium), $C(NHR_2)_3^+$ (guanidinium), $C_5R_6N^+$(pyridinium), $C_3R_5N_2^+$ (imidazolium), $C_2R_4N_3^+$(triazolium), $C_3R_7N_2^+$ (imidazolinium), $SR_3^+$(sulfonium), $PR_4^+$(phosphonium), $IR_2^+$(iodonium), $(C_6R_5)_3C^+$(carbonium), the radicals R independently representing H or a radical selected from the group consisting of alkyl, alkenyl, oxa-alkyl, oxa-alkenyl, aza-alkyl, aza-alkenyl, thia-alkyl, thia-alkenyl, sila-alkyl, sila-alkenyl, aryl, arylalkyl, alkylaryl, alkenylaryl radicals, dialkylamino radicals and dialkylazo radicals;

cyclic or heterocyclic radicals optionally comprising at least one lateral chain comprising heteroatoms such as nitrogen, oxygen, sulfur;

cyclic or heterocyclic radicals optionally comprising heteroatoms in the aromatic nuclei;

groups comprising a plurality of aromatic or heterocyclic, condensed or non-condensed nuclei, optionally containing at least one nitrogen, oxygen, sulfur or phosphorus atom;

with the proviso that a plurality of radicals R may together form aliphatic or aromatic cycles optionally enclosing the center carrying tile cationic charge.

13. An ionically conductingmaterial accotding to claim 11, characterized in that the cation M is a metallic cation selected from the group consisting of cations of alkali metals, cations of alkali-earth metals, cations of transition metals, cations of trivalent metals, cations of rare earth metals and organometallic cations.

14. An ionically conducting material according to claim 11, characterized in that the solvent is either an aprotic liquid solvent, selected from linear ethers and cyclic ethers, esters, nitriles, nitro derivatives, amides, sulfones, sulfolanes, alkylsulfamides and partially halogenated hydrocatons, or a polar polymer, or a mixture thereof.

15. Use of a material comprising an ionic compound in a solvent, wherein said ionic compound consists of an amide or salts thereof, comprising an anionic part associated with at least one cationic part $M^{+m}$ in sufficient number to ensure an electronic neutrality thereto, characterized in that M is a hydroxonium, a nitrosonium $NO^+$, an ammonium —$NH_4^+$, a metallic cation having a valency m, an organic onium cation having a valency m or an organo-metallic cation having a valency m and in that the anionic part corresponds to the formula $R_F$—$SO_X$—$N^-$—Z in which:

the group —S(O)$_X$— represents a sulfonic group —$SO_2$— or a sulfinyl group —SO—;

$R_F$ is a halogen or a perhalogenated alkyl, alkylaryl, oxa-alkyl, aza-alkyl or thia-alkyl radical, or a radical corresponding to one of the formulae $R_ACF_2$—, $R_ACF_2CF_2$—, $R_ACF_2CF(CF_3)$— or $CF_3C(R_A)F$— in which $R_A$— represents a non-perhalogenated organic radical;

Z represents an electro-attractor radical having a Hammett parameter at least equal to that of a phenyl radical, selected from:

j) —CN, —$NO_2$, —SCN, —$N_3$, —$CF_3$, $R'_F$CH$_2$—($R'_F$ being a perfluorinated radical) or a fluoroalkylthioxy radical, jj) radicals comprising one or more aromatic nuclei optionally containing at least one hydrogen, oxygen, sulfur or phosphorus atom, said nuclei optionally being condensed nuclei and/or said nuclei optionally carrying at least one substituent selected from halogens, —CN, —$NO_2$, —SCN, —$N_3$, —$CF_3$, $CF_3CH_2$—, $CF_2$=CF—O—, $CF_2$=CF—S—, perfluoroalkyl groups, fluoroalkyloxy groups, fluoroalkylthioxy groups, alkyl, alkenyl, oxa-alkyl, oxa-alkenyl, aza-alkyl, aza-alkenyl, thia-alkyl, thia-alkenyl radicals, polymer radicals, radicals having at least one cationic ionophoric group and/or at least one anionic ionophoric group;

with the proviso that a substituent Z may be a monovalent radical, part of a multivalent radical carrying a plurality of groups $R_F$—S(O)$_X$—N—, or a polymer segment; or Z is a radical $R_D$—Y— in which Y is a sulfonyl, sulfinyl or phosphonyl group and $R_D$ is a radical selected from the group consisting of:

a) alkyl or alkenyl radicals, aryl, arylalkyl, alkylaryl or alkenylaryl radicals, alicyclic, heterocyclic radicals, or polycyclic radicals;

b) alkyl or alkenyl radicals comprising at least one functional ether, thioether, amine, imine, carboxyl, carbonyl, hydroxy, silyl, isocyanate or thioisocyanate group;

c) aryl, arylalkyl, arylalkenyl, alkylaryl or alkenylaryl radicals, in which the aromatic nuclei and/or at least one substituent of the nucleus comprises heteroatoms selected from nitrogen, oxygen, sulfur;

d) radicals comprising condensed aromatic cycles which optionally comprise at least one heteroatom selected from nitrogen, oxygen, sulfur;

e) halogenated alkyl, alkenyl, aryl, arylalkyl, alkylaryl or alkenylaryl radicals in which the number of carbon atoms carrying at least one halogen is at most equal to the number of non-halogenated carbon atoms, the carbon in α position of group Y not being halogenated when Y is —$SO_2$—, said radicals optionally comprising functional ether, thioether, amine, imine, carboxyl, carbonyl, hydroxy, silyl, isocyanate or thioisocyanate groups;

f) radicals $R_C$C(R')(R'')—O— in which $R_C$ is an alkyl perfluorinated radical and R' and R'' are independently from one another, an hydrogen atom or a radical as defined in a), b), c) or d) above;

g) radicals $(R_B)_2N$—, in which the $R_B$, identical or different, as defined in a), b), c), d) and e) above, one of the $R_B$ may be a hydrogen atom, or the two radicals $R_B$ together form a bivalent radical which forms a cycle with N;

h) radicals consisting of a polymer chain;

i) radicals having one or more cationic ionophoric groups and/or one or more anionic ionophoric groups;

with the proviso that a substituent $R_D$ may be a monovalent radical, part of a multivalent radical carrying a plurality of groups $R_F$S(O)$_X$—N—Y—, or a segment of a polymer;

with the proviso that, when Y is a sulfonyl and $R_D$ is a radical such as defined in a), $R_F$ is $R_ACF_2$—, $R_ACF_2CF_2$—, $R_ACF_2CF(CF_3)$—, $CF_3C(R_A)F$— or a perhaloalkyl radical having 1 to 2 carbon atoms;

wherein the material is used for p or n doping of an electronically conductive polymer, by addition to at least a halogenated hydrocarbon and sulfonic anhydride solution.

16. An ionically conducting material acording to claim 15, characterized in that M is an organic onium cation seleted from the group consisting of $R_3O^+$(oxonium), $NR_4^+$ (ammonium), $RC(NHR_2)_2^+$(amidinium), $C(NHR_2)_3^+$ (guanidinium), $C_5R_6N^+$(pyridinium), $C_3R_5N_2^+$ (imidazolium), $C_2R_4N_3^+$(triazolium), $C_3R_7N_2^+$ (imidazolinium), $SR_3^+$(sulfonium), $PR_4^+$(phosphonium) $IR_2^+$(iodonium), $(C_6R_5)_3C^+$(carbonium), the radicals R independently representing H or a radical selected from the group consisting of:

alkyl, alkenyl, oxa-alkyl, oxa-alkenyl, aza-alkyl, aza-alkenyl, thia-alkyl, thia-alkenyl, sila-alkyl, sila-alkenyl, aryl, arylalkyl, alkylaryl, alkenylaryl radicals, dialkylamino radicals and dialkylazo radicals;

cyclic or heterocyclic radicals optionally comprising at least one lateral chain comprising heteroatoms such as nitrogen, oxygen, sulfur;

cyclic or heterocyclic radicals optionally comprising heteroatoms in the aromatic nuclei;

groups comprising a plurality of aromatic or heterocyclic, condensed or non-condensed nuclei, optionally containing at least one nitrogen, oxygen, sulfur or phosphorus atom;

with the proviso that a plurality of radicals R may together form aliphatic or aromatic cycles optionally enclosing the center carrying the cationic charge.

17. An ionically conducting material according to claim 15, characterized in that the cation M is a metallic cation selected from the group consisting of cations of alkali metals, cations of alkali-earth metals, cations of transition metals, cations of trivalent metals, cations of rare earth metals and organometallic cations.

18. An ionically conducting material according to claim 15, characterized in that $R_F$ is a fluorine atom or a perhalogenad alkyl radical having 1 to 12 carbon atoms, or a perhalogenated alkylaryl radical having 6 to 9 carbon atoms.

19. An ionically conducting material according to claim 15, characterized in that $R_D$ is selected from alkyl, alkenyl, oxa-alkyl, oxa-alkenyl, aza-alkyl, aza-alkenyl, thia-alkyl or thia-alkenyl radicals having 1 to 24 carbon atoms, or from aryl, arylalkyl, alkylaryl or alkenylaryl radicals having 5 to 24 carbon atoms in which the lateral chains and/or the aromatic nuclei comprise heteroatoms.

20. An ionically conducting material according to claim 15, characterized in that $R_D$ is selected from alkyl or alkenyl radicals having 1 to 12 carbon atoms and optionally comprising at least one heteroatom O, N or S in the main chain or in a lateral chain, and/or optionally carrying a hydroxy group, a carbonyl group, an amino group, a carboxyl group, an isocyanate group or a thioisocyanate group.

21. An ionically conducting material according to claim 15, characterized in that $R_D$ is part of a poly(oxyalkylene) radical or a polystyrene radical.

22. Electrochrome device in which the electrolyte is a material comprising an ionic compound in a solvent, wherein said ionic compound consists of an amide or salts thereof, comprising an anionic part associated with at least one cationic part $M^{+m}$ in sufficient number to ensure an electronic neutrality thereto, characterized in that M is a hydroxonium, a nitrosonium $NO^+$, an ammonium $—NH_4^+$, a metallic cation having a valency m, an organic onium cation having a valency m or an organo-metallic cation having a valency m and in that the anionic part corresponds to the formula $R_F—SO_X—N^-—Z$ in which:

the group $—S(O)_X—$ represents a sulfonic group $—SO_2—$ or a sulfinyl group $—SO—$;

$R_F$ is a halogen or a perhalogenated alkyl, alkylaryl, oxa-alkyl, aza-alkyl or thia-alkyl radical, or a radical corresponding to one of the formulae $R_ACF_2—$, $R_ACF_2CF_2—$, $R_ACF_2CF(CF_3)—$ or $CF_3C(R_A)F—$ in which $R_A—$ represents a non-perhalogenated organic radical;

Z represents an electro-attractor radical having a Hammett parameter at least equal to that of a phenyl radical, selected from:

j) $—CN, —NO_2, —SCN, —N_3, —CF_3, R'_FCH_2—$ ($R'_F$ being a perfluorinated radical) or a fluoroalkylthioxy radical, jj) radicals comprising one or more aromatic nuclei optionally containing at least one hydrogen, oxygen, sulfur or phosphorus atom, said nuclei optionally being condensed nuclei and/or said nuclei optionally carrying at least one substituent selected from halogens, $—CN, —NO_2, —SCN, —N_3, —CF_3$, $CF_3CH_2—$, $CF_2=CF—O—$, $CF_2=CF—S—$, perfluoroalkyl groups, fluoroalkyloxy groups, fluoroalkylthioxy groups, alkyl, alkenyl, oxa-alkyl, oxa-alkenyl, aza-alkyl, aza-alkenyl, thia-alkyl, thia-alkenyl radicals, polymer radicals, radicals having at least one cationic ionophoric group and/or at least one anionic ionophoric group;

with the proviso that a substituent Z may be a monovalent radical, part of a multivalent radical carrying a plurality of groups $R_F—S(O)_X—N—$, or a polymer segment; or Z is a radical $R_D—Y—$ in which Y is a sulfonyl, sulfinyl or phosphonyl group and $R_D$ is a radical selected from the group consisting of:

a) alkyl or alkenyl radicals, aryl, arylalkyl, alkylaryl or alkenylaryl radicals, alicyclic, heterocyclic radicals, or polycyclic radicals;

b) alkyl or alkenyl radicals comprising at least one functional ether, thioether, amine, imine, carboxyl, carbonyl, hydroxy, silyl, isocyanate or thioisocyanate group;

c) aryl, arylalkyl, arylalkenyl, alkylaryl or alkenylaryl radicals, in which the aromatic nuclei and/or at least one substituent of the nucleus comprises heteroatoms selected from nitrogen, oxygen, sulfur;

d) radicals comprising condensed aromatic cycles which optionally comprise at least one heteroatom selected from nitrogen, oxygen, sulfur;

e) halogenated alkyl, alkenyl, aryl, arylalkyl, alkylaryl or alkenylaryl radicals in which the number of carbon atoms carrying at least one halogen is at most equal to the number of non-halogenated carbon atoms, the carbon in α position of group Y not being halogenated when Y is $—SO_2—$, said radicals optionally comprising functional ether, thioether, amine, imine, carboxyl, carbonyl, hydroxy, silyl, isocyanate or thioisocyanate groups;

f) radicals $R_CC(R')(R'')—O—$ in which $R_C$ is an alkyl perfluorinated radical and R' and R" are independently from one another, an hydrogen atom or a radical as defined in a), b), c) or d) above;

g) radicals $(R_B)_2N—$, in which the $R_B$, identical or different, as defined in a), b), c), d) and e) above, one of the $R_B$ may be a hydrogen atom, or the two radicals $R_B$ together form a bivalent radical which forms a cycle with N;

h) radicals consisting of a polymer chain;

i) radicals having one or more cationic ionophoric groups and/or one or more anionic ionophoric groups;

with the proviso that a substituent $R_D$ may be a monovalent radical, part of a multivalent radical carrying a plurality of groups $R_FS(O)_X$—N—Y—, or a segment of a polymer;

with the proviso that, when Y is a sulfonyl and $R_D$ is a radical such as defined in a), $R_F$ is $R_ACF_2$—, $R_ACF_2CF_2$—, $R_ACF_2CF(CF_3)$—, $CF_3C(R_A)F$— or a perhaloalkyl radical having 1 to 2 carbon atoms.

23. An ionically conducting material according to claim 22, characterized in that M is an organic onium cation selected from the group consisting of $R_3O^+$(oxonium), $NR_4^+$ (ammonium), $RC(NHR_2)_2^+$(amidinium), $C(NHR_2)_3^+$ (guanidinium), $C_5R_6N^+$(pyridinium), $C_3R_5N_2^+$ (imidazolium), $C_2R_4N_3^+$(triazolium), $C_3R_7N_2^+$ (imidazolinium), $SR_3^+$(sulfonium), $PR_4^+$(phosphonium), $IR_2^+$(iodonium), $(C_6R_5)_3C^+$(carbonium), the radicals R independently representing H or a radical selected from the group consisting of:

alkyl, alkenyl, oxa-alkyl, oxa-alkenyl, aza-alkyl aza-alkenyl, thia-alkyl, thia-alkenyl, sila-alkyl, sila-alkenyl, aryl, arylalkyl, alkylaryl, alkenylaryl radicals, dialkylamino radicals and dialkylazo radicals;

cyclic or heterocyclic radicals optionally comprising at least one lateral chain comprising heteroatoms such as nitrogen, oxygen, sulfur;

cyclic or heterocyclic radicals optionally comprising heteroatoms in the aromatic nuclei;

groups comprising a plurality of aromatic or heterocyclic, condensed or non-condensed nuclei, optionally containing at least one nitrogen, oxygen, sulfur or phosphorus atom;

with the proviso that a plurality of radicals R may together form aliphatic or aromatic cycles optionally enclosing the center carrying the cationic charge.

24. An ionically conducting material according to claim 22, characterized in that the cation M is a metallic cation selected from the group consisting of cations of alkali metals, cations of alkali-earth metals, cations of transition metals, cations of trivalent metals, cations of rare earth metals and organometallie cations.

25. An ionically conducting material according to claim 22, characterized in that $R_F$ is a fluorine atom or a perhalogenated alkyl radical having 1 to 12 carbon atoms, or a perhalogenated alkylaryl radical having 6 to 9 carbon atoms.

26. An ionically conducting material according to claim 22, characterized in that $R_D$ selected from alkyl, alkenyl, oxa-alkyl, oxa-alkenyl, aza-alkyl, aza-alkenyl, thia-alkyl or thia-alkenyl radicals having 1 to 24 carbon atoms, or from aryl, arylalkyl, alkylaryl or alkenylaryl radicals having 5 to 24 carbon atoms in which the lateral chains and/or the aromatic nuclei comprise heteroatoms.

27. An ionically conducting material according to claim 22, characterized in that $R_D$ is selected from alkyl or alkenyl radicals having 1 to 12 carbon atoms and optionally comprising at least one heteroatom O, N or S in the main chain or in a lateral chain, and/or optionally carryig a hydroxy group, a carbonyl group, an amine group, a carboxyl group, an isocyanate group or a thioisocyanate group.

28. An ionically conducting material according to claim 22, characterized in that $R_D$ is part of a poly(oxyalkylene) radical or a polystyrene radical.

29. An ionically conducting material according to claim 22, characterized in that the solvent is either an aprotic liquid solvent, selected from linear ethers and cyclic ethers, esters, nitriles, nitro derivatives, amides, sulfones, sulfolanes, alkylsulfamides and partially halogenated hydrocarbons, or a polar polymer, or a mixture thereof.

30. Electronically conductive material comprising an ionic compound in a solvent, wherein said ionic compound consists of an amide or salts thereof, comprising an anionic part associated with at least one cationic part $M^{+m}$ in sufficient number to ensure an electronic neutrlty thereto, characterized in that M is a hydroxonium, a nitrosonium $NO^+$, an ammonium —$NH_4^+$, a metallic cation having a valency m, an organic onium cation having a valency m or an organo-metallie cation having a valency m and in that the anionic part corresponds to the formula $R_F$—$SO_X$—$N^-$—Z in which:

the group —$S(O)_X$— represents a sulfonic group —$SO_2$— or a sulfinyl group —SO—;

$R_F$ is a halogen or a perhalogenated alkyl alkylaryl, oxa-alkyl, aza-alkyl or thia-alkyl radical, or a radical corresponding to one of the formulae $R_ACF_2$—, $R_ACF_2CF_2$—, $R_ACF_2CF(CF_3)$— or $CF_3C(R_A)F$— in which $R_A$— represents a non-perhalogenated organic radical;

Z represents an electro-attractor radical having a Hammett parameter at least equal to that of a phenyl radical, selected from:

j) —CN, —$NO_2$, —SCN, —$N_3$, $CF_3$, $R'_FCH_2$— ($R'_F$ being a perfluorinated radical) or a fluoroalkylthioxy radical, jj) radicals comprising one or more aromatic nuclei optionally containing at least one hydrogen, oxygen, sulfur or phosphorus atom, said nuclei optionally being condensed nuclei and/or said nuclei optionally carrying at least one substituent selected from halogens, —CN, —$NO_2$, —SCN, —$N_3$, —$CF_3$, $CF_3CH_2$=, $CF_2$—CF—O—, $CF_2$=CF—S—, perfuoroalkyl groups, fluoroalkyloxy groups, fluoroalkylthioxy groups, alkyl, alkenyl, oxa-alkyl, oxa-alkenyl, aza-alkyl, aza-alkenyl, thia-alkyl, thia-alkenyl radicals, polymer radicals, radicals having at least one cationic ionophoric group and/or at least one anionic ionophoric group;

with the proviso that a substituent Z may be a monovalent radical, part of a multivalent radical carrying a plurality of groups $R_F$—$S(O)_X$—N—, or a polymer segment; or Z is a radical $R_D$—Y— in which Y is a sulfonyl, sulfinyl or phosphonyl group and $R_D$ is a radical selected from the group consisting of:

a) alkyl or alkenyl radicals, aryl, arylalkyl, alkylaryl or alkenylaryl radicals, alicyclic, heterocyclic radicals, or polycyclic radicals;

b) alkyl or alkenyl radicals comprising at least one functional ether, thioether, amine, imine, carboxyl, carbonyl hydroxy, silyl, isocyanate or thioisocyanate group;

c) aryl, arylalkyl, arylalkenyl, alkylaryl or alkenylaryl radicals, in which the aromatic nuclei and/or at least one substituent of the nucleus comprises heteroatoms selected from nitrogen, oxygen, sulfur;

d) radicals comprising condensed aromatic cycles which optionally comprise at least one heteroatom selected from nitrogen, oxygen, sulfur;

c) halogenated alkyl, alkenyl, aryl, arylalkyl, alkylaryl or alkenylaryl radicals in which the number of carbon atoms carrying at least one halogen is at most equal to the number of non-halogenated carbon atoms, the carbon in α position of group Y not being halogenated when Y is —SO$_2$—, said radicals optionally comprising functional others thioether, amine, imine, carboxyl, cabonyl, hydroxy, silyl, isocyanate or thioisocyanate groups;

f) radicals R$_C$C(R')(R")—O— in which R$_C$ is an alkyl perfluorinated radical and R' and R" are independently from one another, an hydrogen atom or a radical as defined in a), b), c) or d) above;

g) radicals (R$_B$)$_2$N—, in which the R$_B$, identical or different, as defined in a), b), c), d) and e) above, one of the R$_B$ may be a hydrogen atom, or the two radicals R$_B$ together form a bivalent radical which forms a cycle with N;

h) radicals consisting of a polymer chain;

i) radicals having one or more cationic ionophoric groups and/or one or more anionic ionophoric groups;

with the proviso that a substituent R$_D$ may be a monovalent radical, part of a multivalent radical carrying a plurality of groups R$_F$S(O)X—N—Y—, or a segment of a polymer;

with the proviso that, when Y is a sulfonyl and R$_D$ is a radical such as defined in a), R$_F$ is R$_A$CF$_2$—, R$_A$CF$_2$CF$_2$—, R$_A$CF$_2$CF(CF$_3$)—, CF$_3$C(R$_A$)F— or a perhaloalkyl radical having 1 to 2 carbon atoms, characterized in that the cationic part of the ionic compound is a polycation consisting of a doped conjugated polymer "p".

31. An ionically conducting material according to claim 30, charactedzed in that the solvent is either an aprotic liquid solvent, selected from linear ethers and cyclic ethers, esters, nitriles, nitro derivatives, amides, sulfones, sulfolanes, alkylsulfamides and parlially halogenated hydrocarbons, or a polar polymer, or a mixture thereof.

32. Electronically conductive material comprising an ionic compound in a solvent, wherein said ionic compound consists of an amide or salts thereof, comprising an anionic part associated with at least one cationic part M$^{+m}$ sufficicent number to ensure an electronic neutrality thereto, characterized in that M is a hydroxonium, a nitrosonium NO$^{30}$, an ammonium —NH$^+$, a metallic cation having a valency m, an organic onium cation having a valency m or an organometallic cation having a valency m and in that the anionic part corresponds to the formula R$_F$—SO$_X$—N$^-$—Z in which:

the group —S(O)$_X$— represents a sulfonic group —SO$_2$— or a sulfinyl group —SO—;

R$_F$ is a halogen or a perhalogenated alkyl alkylaryl, oxa-alkyl, aza-alkyl or thia-alkyl radical, or a radical corresponding to one of the formulae R$_A$CF$_2$—, R$_A$CF$_2$CF$_2$—, R$_A$CF$_2$CF(CF$_3$)— or CF$_3$C(R$_A$)F— in which R$_A$— represents a non-perhalogenated organic radical;

Z represents an elcctro-attractor radical having a Hammett parameter at least equal to that of a phenyl radical, selected from:

j) —CN, —NO$_2$, —SCN, —N$_3$, —CF$_3$, R'$_F$CH$_2$— (R'$_F$ being a perfluorinated radical) or a fluoroalkylthioxy radical, jj) radicals comprising one or more aromatic nuclei optionally containing at least one hydrogen, oxygen, sulfur or phosphorus atom, said nuclei optionally being condensed nuclei and/or said nuclei optionally carrying at least one substituent selected from halogens, —CN, —NO$_2$, —SCN, —N$_3$, —CF$_3$, CF$_3$CH$_2$—, CF$_2$=CF—O—, CF$_2$=CF—S—, perfluoroalkyl groups, fluoroalkyloxy groups, fluoroalkylthioxy groups, alkyl, alkenyl, oxa-alkyl, oxa-alkenyl, aza-alkyl, aza-alkenyl, thia-alkyl thiaalkenyl radicals, polymer radicals, radicals having at least one cationic ionophoric group and/or at least one anionic ionophoric group;

with the proviso that a substituent Z may be a monovalent radical part of a multivalent radical carrying a plurality of groups R$_F$—S(O)$_X$—N—, or a polymer segment; or Z is a radical R$_D$—Y— in which Y is a sulfonyl, sulfinyl or phosphonyl group and R$_D$ is a radical selected from the group consisting of:

a) alkyl or alkenyl radicals, aryl, arylalkyl alkylaryl or alkenylaryl radicals, alicyclic, heterocyclic radicals, or polycyclic radicals;

b) alkyl or alkenyl radicals comprising at least one functional ether, thioether, amine, imine, carboxyl, carbonyl, hydroxy, silyl, isocyanate or thioisocyanate group;

c) aryl arylkyl, arylalkenyl, alkylaryl or alkenylaryl radicals, in which the aromatic nuclei and/or at least one substituent of the nucleus comprises heteroatoms selected from nitrogen, oxygen, sulfur;

d) radicals comprising condensed aromatic cycles which optionally comprise at least one heteroatom selected from nitrogen, oxygen, sulfur;

e) halogenated alkyl, alkenyl, aryl, arylalkyl, alkylaryl or alkenylaryl radicals in which the nunmber of carbon atoms carrying at least one halogen is at most equal to the number of non-halogenated carbon atoms, the carbon in α position of group Y not being halogenated when Y is —SO$_2$—, said radicals optionally comprising functional ether, thioether, amine, imine, carboxyl, carbonyl, hydroxy, silyl, isocyanate or thioisocyanate groups;

f) radicals R$_C$C(R')(R")—O— in which R$_C$ is an alkyl perfluorinated radical and R' and R" are indepedently from one another, an hydrogen atom or a radical as defined in a), b), c) or d) above;

g) radicals (R$_B$)$_2$N—, in which the R$_B$, identical or different, as defined in a), b), c), d) and e) above, one of the R$_B$ may be a hydrogen atom, or the two radicals R$_B$ together form a bivalent radical which forms a cycle with N;

h) radicals consisting of a polymer chain;

i) radicals having one or more cationic ionophoric groups and/or one or more anionic ionophoric groups;

with the proviso that a substituent R$_D$ may be a monovalent radical, part of a multivalent radical carrying a plurity of groups R$_F$S(O)X—N—Y—, or a segment of a polymer;

with the proviso that, when Y is a sulfonyl and R$_D$ is a radical such as defined in a), R$_F$ is R$_A$CF$_2$—, R$_A$CF$_2$CF$_2$—, R$_A$CF$_2$CF(CF$_3$)—, CF$_3$C(R$_A$)F— or a perhaloalkyl radical having 1 to 2 carbon atoms, characterized in that the substituent Z of the ionic compound comprises an alkyl chain having 6 to 20 carbon atoms.

33. An ionically conducdng material comprising an ionic compound in a solvent, wherein said ionic compound consists of an amide or salts thereof, comprising an anionic part associated with at least one cationic part M$^{+m}$ in sufficient number to ensure an electronic neutrality thereto, characterized in that M is a hydroxonium, a nitrosonium $NO^+$, an ammonium $—NH_4^+$, a metallic cation having a valency m, an organic onium cation having a valency m or an organo-metallic cation having a valency m and in that the anionic part corresponds to tho formula $R_F—SO_XN^-—Z$ in which:

the group $—S(O)_X—$ represents a sulfonic group $—SO_2—$ or a salfinyl group $—SO—$;

$R_F$ is a halogen or a perhalogenated alkyl, alkylaryl, oxa-alkyl, aza-alkyl or thia-alkyl radical, or a radical corresponding to one of the formulae $R_ACF_2—$, $R_ACF_2CF_2—$, $R_ACF_2CF(CF_3)—$ or $CF_3C(R_A)F—$ in which $R_A—$ represents a non-perhalogenated organic radical;

Z represents an electro-attractor radical having a Hammett parameter at least equal to that of a phenyl radical, selected from:

j) $—CN$, $—NO_2$, $—SCN$, $—N_3$, $—CF_3$, $R'_FCH_2—$ ($R'_F$ being a perfluorinated radical) or a fluoroalkylthioxy radical, jj) radicals comprising one or more aromatic nucli optionally containing at least one hydrogen, oxygen, sulfur or phosphorus atom, said nuclei optionally being condensed nuclei and/or said nuclei optionally carrying at least one substituent selected from halogens, $—CN$, $—NO_2$, $—SCN$, $—N_3$, $—CF_3$, $CF_3CH_2—$, $CF_2=CF—O—$, $CF_2=CF—S—$, perfluoroalkyl groups, fluoroalkyloxy groups, fluoro-alkylthioxy groups, alkyl, alkeniyl, oxa-alkyl, oxa-alkenyl, aza-alkyl, aza-alkenyl, thia-alkyl, thia-alkenyl radicals, polymer radicals, radicals having at least one cationic ionophoric group and/or at least one anionic ionophoric group;

with the proviso that a substituent Z may be a monovalont radical, part of a multivalent radical carying a plurality of groups $R_F—S(O)_X—N—$, or a polymer segment; or Z is a radical $R_D—Y—$ in which Y is a sulfonyl, sulfinyl or phosphonyl group and $R_D$ is a radical selected from the group consisting of:

a) alkyl or alkenyl radicals, aryl, arylalkyl, alkylaryl or alkenylaryl radicals, alicyclic, heterocyclic radicals, or polycyclic radicals;

b) alkyl or alkenyl radicals comprising at least one functional ether, thioether, amine, imine, carboxyl, carbonyl, hydroxy, silyl, isocyanate or thioisocyanate group;

c) aryl, arylalkyl, arylalkenyl, alkylaryl or alkenylaryl radicals, in which the aromatic nuclei and/or at least one substituent of the nucleus comprises heteroatoms selected from nitrogen, oxygen, sulfur;

d) radicals comprising condensed aromatic cycles which optionally comprise at least one hetoroatom selected from nitrogen, oxygen, sulfur;

e) halogenated alkyl, alkenyl, aryl, arylalkyl, alkylaryl or alkenylaryl radicals in which the number of carbon atoms carrying at least one halogen is at most equal to the number of non-halogenated carbon atoms, the carbon in α position of group Y not being halogenated when Y is $—SO_2—$, said radicals optionally comprising functional ether, thioether, amine, imino, carboxyl, caibonyl, hydroxy, silyl, isocyanate or thioisocyanate groups;

f) radicals $R_CC(R')(R")—O—$ in which $R_C$ is an alkyl perfluorinatcd radical and R' and R" are independently from one mother, an hydrogen atom or a radical as defined in a), b), c) or d) above;

g) radicals $(R^B)_2N—$, in which the $R_B$, identical or different, as defined in a), b), c), d) and e) above, one of the $R_B$ may be a hydrogen atom, or the two radicals $R_B$ together fonn a bivalent radical which forms a cycle with N;

h) radicals consisting of a polymer chain;

i) radicals having one or more cationic ionophoric groups and/or one or more anionic ionophoric groups;

with the proviso that a substituent $R_D$ may be a monovalent radical, part of a multivalent radical carrying a plurality of groups $R_FS(O)_X—N—Y—$, or a segment of a polymer;

with the proviso that, when Y is a sulfonyl and $R_D$ is a radical such as defined in a), $R_F$ is $R_ACF_2—$, $R_ACF_2CF_2—$, $R_ACF_2CF(CF_3)—$, $CF_3C(R_A)F—$ or a perhaloalkyl radical having 1 to 2 carbon atoms, characterized in that M is an organic onium cation selected from the group consisting of $R_3O^+$(oxonium), $NR_4^+$ (ammonium), $RC(NHR_2)_2^+$(amidinium), $C(NHR_2)_3^+$ (guanidinium), $C_5R_6N^+$(pyridinium), $C_3R_5N_2^+$ (imidazolium), $C_2R_4N_3^+$(triazolium), $C_3R_7N_2^+$ (imidazolinium), $SR_3^+$(sulfonium), $PR_4^+$(phosphonium), $IR_2^+$(iodonium), $(C_6R_5)_3C^+$(carbonium), the radicals R independently representing H or a radical selected from the group consisting of:

alkyl, alkenyl, oxa-alkyl oxa-alkenyl, aza-alkyl, aza-alkenyl, thia-alkyl, thia-alkenyl, sila-alkyl, sila-alkenyl, aryl, arylalkyl, alkylaryl, alkenylaryl radicals, dialkylamino radicals and dialkylazo radicals;

cyclic or heterocyclic radicals optionally comprising at least one lateral chain comprising heteroatoms such as nitrogen, oxygen, sulfur;

cyclic or heterocyclic radicals optionally comprising heteroatoms in the aromatic nuclei;

groups comprising a plurality of aromatic or heterocyclic, condensed or non-condensed nuclei, optionally containing at least one nitrogen, oxygen, sulfur or phosphorus atom;

with the proviso that a plurality of radicals R may together form aliphatic or aromatic cycles optionally enclosing the center carrying the cationic charge and characterized in that M is an organic onium cation that is part of a recurring unit of a polymer.

34. An ionically conducting material comprising an ionic compound in a solvent, wherein said ionic compound consists of an amide or salts therof, comprising an anionic pat associated with at least one calionic part $M^{+m}$ in sufficient number to ensure an electronic neutrality thereto, characterized in that M is a hydroxonium, a nitrosonium $NO^+$, an ammonium $—NH_4^+$, a metallic cation having a valency m, an organic onium cation having a valency m or an organo-metallic cation having a valency m and in that the anionic part corresponds to the formula $R_F—SO_X—N^-—Z$ in which:

the group $—S(O)_X—$ represents a sulfonic group $—SO_2—$ or a sulfinyl group $—SO—$;

$R_F$ is a halogen or a perhalogenated alkyl, alkylaryl, oxa-alkyl, aza-alkyl or thia-alkyl radical, or a radical corresponding to one of the formulae $R_ACF_2—$, $R_ACF_2CF_2—$, $R_ACF_2CF(CF_3)—$ or $CF_3C(R_A)F—$ in which $R_A—$ represents a non-perhalogenated organic radical;

Z represents an electro-attractor radical having a Hammett parameter at least equal to that of a phenyl radical, selected from:

j) —CN, —NO$_2$, —SCN, —N$_3$, —CF$_3$, R'$_F$CH$_2$— (R'$_F$ being a perfluorinated radical) or a fluoroalkylthioxy radical, jj) radicals comprising one or more aromatic nuclei optionally containing at least one hydrogen, oxygen, sulfur or phosphorus atom, said nuclei optionally being condensed nuclei and/or said nuclei optionally carrying at least one substituent selected from halogens, —CN, —NO$_2$, —SCN, —N$_3$, —CF$_3$, CF$_3$CH$_2$—, CF$_2$=CF—O—, CF$_2$=CF—S—, perufloroaklyl groups, fluoroalkyloxy groups, fluoroalkylthioxy groups, alkyl, alkenyl, oxa-alkyl, oxa-alkenyl, aza-alkyl, aza-alkenyl, thia-alkyl, thia-alkenyl radicals, polymer radicals, radicals having at least one cationic ionophoric group and/or at least one anionic ionophoric group;

with the proviso that a substituent Z may be a monovalent radical, part of a multivalent radical carrying a plurality of groups R$_F$—S(O)$_X$—N—, or a polymer segment; or Z is a radical R$_D$—Y— in which Y is a sulfonyl, sulfinyl or phosphonyl group and R$_D$ is a radical selected from the group consisting of:

a) alkyl or alkenyl radicals, aryl, arylalkyl, alkylaryl or alkenylaryl radicals, alicyclic, heterocyclic radicals, or polycyclic radicals;

b) alkyl or alkenyl radicals comprising at least one functional ether, thioether, amine, iminee, carboxyl, carbonyl, hydroxy, silyl, isocyanate or thioisocyanate group;

c) aryl, arylalkyl, arylalkenyl, alkylaryl or alkenylaryl radicals, in which the aromatic nuclei and/or at least one substituent of the nucleus comprises heteroatoms selected from nitrogen, oxygen, sulfur;

d) radicals comprising condensed aromatic cycles which optionally comprise at least one heteroatom selected from nitrogen, oxygen, sulfur;

e) halogenated alkyl, alkenyl, aryl, arylalkyl alkylaryl or alkenylaryl radicals in which the number of carbon atoms carrying at least one halogen is at most equal to the number of non-halogenated carbon atoms, the carbon in α position of group Y not being halogenated when Y is —SO$_2$—, said radicals optionally comprising functional ether, thioether, amine, imine, carboxyl, carbonyl, hydroxy, silyl, isocyanate or thioisocyanato groups;

f) radicals R$_C$-C(R')(R")—O— in which R$_C$ is an alkyl perfluorinated radical and R' and R" are indpdently from one another, an hydrogen atom or a radical as defined in a), b), c) or d) above;

g) radicals (R$_B$)$_2$N—, in which the R$_B$, identical or different, as defined in a), b), c), d) and e) above, one of the R$_B$ may be a hydrogen atom, or the two radicals R$_B$ together form a bivalent radical which forms a cycle with N;

h) radicals consisting of a polymer chain;

i) radicals having one or more cationic ionophoric groups and/or one or more anionic ionophoric groups;

with the proviso that a substituent R$_D$ may be a monovalent radical, part of a multivalent radical carrying a plurality of groups R$_F$S(O)X—N—Y—, or a segment of a polymer;

with the proviso that, when Y is a sulfonyl and R$_D$ is a radical such as defined in a), R$_F$ is R$_A$C$_2$—, R$_A$CF$_2$CF$_2$—, R$_A$CF$_2$CF(CF$_3$)—, CF$_3$C(R$_A$)F— or a perhaloalkyl radical having 1 to 2 carbon atoms, characterized that M is an organic onium cation selected from the group consisting of R$_3$O$^+$(oxonium), NR$_4^+$(ammonium), RC(NHR$_2$)$_2^+$(amidinium), C(NHR$_2$)$_3^+$(guanidinium), C$_5$R$_6$N$^+$(pyridinium), C$_3$R$_5$N$_2^+$(imidazolium), C$_2$R$_4$N$_3^+$(triazolium), C$_3$R$_7$N$_2^+$(imidazolinium), SR$_3^+$(sulfonium), PR$_4^+$ (phosphonium), IR$_2^+$(iodonium), (C$_6$R$_5$)$_3$C$^+$ (carbonium), the rdicals R independently representing H or a radical selected from the group consisting of:

alkyl, alkenyl, oxa-alkyl, oxa-alkenyl, aza-alkyl, aza-alkenyl, thia-alkyl, thia-alkenyl, sila-alkyl, sila-alkenyl, aryl, arylalkyl, alkylaryl, alkenylaryl radicals, dialkylamino radicals and dialkylazo radicals;

cyclic or heterocyclic radicals optionally comprising at least one lateral chain comprising heteroatoms such as nitrogen, oxygen, sulfur, cyclic or heterocyclic radicals optionally comprising heteroatoms in the aromatic nuclei;

groups comprising a plurality of aromatic or heterocyclic, condensed or non-condensed nuclei, optionally containing at least one nitrogen, oxygen, sulfur or phosphorus atom;

with the proviso that a plurality of radicals R may together form aliphatic or aromatic cycles optionally enclosing the center carrying the cationic charge and characterized in that the cation M is a group having a bond —N=N—, —N=N$^+$, a sulfonium group, an iodonium group, or a substituted or non-substituted arene-ferocenium cation, optionally incorporated in a polymer network.

35. An ionically conducting material comprising an ionic compound in a solvent, wherein said ionic compound consists of an amide or salts thereof, comprising an anionic part associated with at least one cationic part M$^{+m}$ in sufficient number to ensure an electronic neutrality thereto, characterzed in that M is a hydroxonium, a nitrosonium NO$^+$, an ammonium —NH$_4^+$, a metallic cation having a valency m, an organic onium cation having a valency m or an organometallic cation having a valency m and in that the anionic part corresponds to the formula R$_F$—SO$_X$—N$^-$—Z in which:

the group —S(O)$_X$— represents a sulfonic group —SO$_2$— or a sulfinyl group —SO—;

R$_F$ is a halogen or a perhalogenated alkyl, alkylaryl, oxa-alkyl, aza-alkyl or thia-alkyl radical, or a radical corresponding to one of the formulae R$_A$CF$_2$—, R$_A$CF$_2$CF$_2$—, R$_A$CF$_2$CF(CF$_3$)— or CF$_3$C(R$_A$)F— in which R$_A$— represents a non-perhalogenated organic radical;

Z represents an electro-attractor radical having a Hammett parameter at least equal to that of a phenyl radical, selected from:

j) —CN, —NO$_2$, —SCN, —N$_3$, —CF$_3$, R'$_F$CH$_2$— (R'$_F$ being a perfluorinated radical) or a fluoroalkylthioxy radical, jj) radicals comprising one or more aromatic nuclei optionally containing at least one hydrogen, oxygen, sulfur or phosphoms atom, said nuclei optionally being condensed nuclei and/or said nuclei optionally carrying at least one substituent selected from halogen, —CN, —NO$_2$, —SCN, —N$_3$, —CF$_3$, CF$_3$CH$_2$—, CF$_2$=CF—O—, CF$_2$=CF—S—, perfluoroalkyl groups, fluoroalkyloxy groups, fluoroalkylthioxy groups, alkyl, alkenyl, oxa-alkyl, oxa-alkenyl, aza-alkyl, aza-alkenyl, thia-alkyl, thia-alkenyl radicals, polymer radicals, radicals having at least one cationic ionophonic group and/or at least one anionic ionophoric group;

with the proviso that a substituent Z may be a monovalent radical, part of a multivalent radical carrying a plurality of groups $R_F$—S(O)$_X$—N—, or a polymer segment; or Z is a radical $R_D$—Y— in which Y is a sulfonyl, sulfinyl or phosphonyl group and $R_D$ is a radical selected from the group consisting of:
  a) alkyl or alkenyl radicals, aryl, arylalkyl, alkylaryl or alkenylaryl radicals, alicyclic, heterocyclic radicals, or polycyclic radicals;
  b) alkyl or alkenyl radicals comprising at least one functional ether, thioether, amine, imine, carboxyl, carbonyl, hydroxy, silyl, isocyanate or thioisocyanate group;
  c) aryl, arylalkyl, arylalkenyl, alkylaryl or alkenylaryl radicals, in which the aromatic nuclei and/or at least one substituent of the nucleus comprises heteroatoms selected from nitrogen, oxygen, sulfur;
  d) radicals corprising condensed aromatic cycles which optionally comprise at least one heteroatom selected fronn nitrogen, oxygen, sulfur;
  e) halogenated alkyl, alkenyl, aryl, alylalkyl alkylaryl or alkenylaryl radicals in which the number of carbon atoms carryng at least one halogen is at most equal to the number of non-halogenated carbon atoms, the carbon in α position of group Y not being halogenated when Y is —SO$_2$—, said radicals optionally comprising functional other, thioether, amine, imine, carboxyl, carbonyl, hydroxy, silyl, isocyanate or thioisocyanate groups;
  f) radicals $R_CC(R')(R'')$—O— in which $R_C$ is an alkyl perfluorinated radical and R' and R" are independently from one another, an hydrogen atom or a radical as defined in a), b), c) or d) above;
  g) radicals $(R_B)_2N$—, in which the $R_B$, identical or different, as defined in a), b), c), d) and e) above; one of the $R_B$ may be a hydrogen atom, or the two radicals $R_B$ together form a bivalent radical which forms a cycle with N;
  h) radicals consisting of a polymer chain;
  i) radicals having one or more cationic ionophoric groups and/or one or more anionic ionophoric groups;

with the proviso that a substituent $R_D$ may be a monovalent radical, part of a multivalent radical carrying a plurality of groups $R_FS(O)x$—N—Y—, or a segment of a polymer;

with the proviso that when Y is a sulfonyl and $R_D$ is a radical such as defined in a), $R_F$ is $R_ACF_2$—, $R_ACF_2CF_2$—, $R_ACF_2CF(CF_3)$—, $CF_3C(R_A)F$— or a perhaloalkyl radical having 1 to 2 carbon atoms, characterized in that M is an organic onium cation selected from the group consisting of $R_3O^+$(oxonium), $NR_4^+$(ammonium), $RC(NHR_2)_2^+$(amidinium), $C(NHR_2)_3^+$(guanidinium), $C_5R_6N^+$(pyridinium), $C_3R_5N_2^+$(imidazolium), $C_2R_4N_3^+$(triazolium), $C_3R_7N_2^+$(imidazolinium), $SR_3^+$(sulfonium), $PR_4^+$ (phosphonium), $IR_2^+$(iodonium), $(C_6R_5)_3C^+$ (carbonium), the radicals R independently representing H or a radical selected from the group consisting of:
  alkyl, alkenyl, oxa-alkyl, oxa-alkenyl, aza-alkyl, aza-alkenyl, thia-alkyl, thia-alkenyl, sila-alkyl, sila-alklenyl, aryl, arylalkyl, alkylaryl, alkenylaryl radicals, dialkylamino radicals and dialkylazo radicals;
  cyclic or heterocyclic radicals optionally comprising at least one lateral chain comprising heteroatoms such as nitrogen, oxygen, sulfur;
  cyclic or heterocyclic radicals optionally comprising heteroatoms in the aromatic nuclei;
  groups comprising a plurality of aromatic or heterocyclic, condensed or non-condensed nuclei, optionally containing at least one nitrogen, oxygen, sulfur or phosphorus atom;
  with the proviso that a plurality of radicals R may together forn aliphatic or aromatic cycles optionally enclosing the center carrying the cationic charge and characterized in that M is a cation that is a diaryliodonium cation, a dialkylaryliodonium cation, a triarylsulifonium cation, a trialkylaryl sulfonium cation, or a substituted or non-substituted phenacyl-alkyl sulfonium cation.

36. An ionically conducting material according to claim 35, chacterized in that M is a cation that is part of a polymer chain.

37. An ionically conducting material comprising an ionic compound in a solvent, wherein said ionic compound consists of an amide or salts thereof, comprising an anionic part associated with at least one cationic part $M^{+m}$ in sufficient number to ensure an electronic neutrality thereto, characterized in that M is a hydroxonium, a nitrosonium $NO^+$, an ammonium —$NH_4^+$, a metallic cation having a valency m, an organic onium cation having a valency m or an organometallic cation having a valency m and in that the anionic part corresponds to the fomula $R_F$—SO$_X$—N$^-$—Z in which:
  the group —S(O)$_X$— represents a sulfonic group —SO$_2$— or a sulfinyl group —SO—;
  $R_F$ is a halogen or a perhalogenated alkyl, alkylaryl, oxa-alkyl, aza-alkyl or thia-alkyl radical, or a radical corresponding to one of the formulae $R_ACF_2$—, $R_ACF_2CF_2$—, $R_ACF_2CF(CF_3)$— or $CF_3C(R_A)F$— in which $R_A$— represents a non-perhalogenated organic radical;
  Z represents an electro-attractor radical having a Hammett parameter at least equal to that of a phenyl radical, selected from:
    j) —CN, —NO$_2$, —SCN, —N$_3$, —CF$_3$, R'$_F$CH$_2$— (R'$_F$ being a perfluorinated radical) or a fluoroalkylthioxy radical,
    jj) radicals comprising one or more aromatic nuclei optionally containing at least one hydrogen, oxygen, sulfur or phosphorus atom, said nuclei optionally being condensed nuclei and/or said nuclei optionally carrying at least one substituent selected from halogens, —CN, —NO$_2$, —SCN, —N$_3$, —CF$_3$, CF$_3$CH$_2$—, CF$_2$=CF—O—, CF$_2$=CF—S—, perfluoroalkyl groups, fluoroalkyloxy groups, fluoroalkylthioxy groups, alkyl, alkenyl, oxa-alkyl, oxa-alkenyl, aza-alkyl, aza-alkenyl, thia-alkyl, thia-alkenyl radicals, polymer radical, radicals having at least one cationic ionophoric group and/or at least one anionic ionophoric group;
  with the proviso that a substituent Z may be a monovalent radical, part of a multivalent radical carrying a plurality of groups $R_FS(O)_X$—N—, or a polymer segment; or
  Z is a radical $R_D$—Y— in which Y is a sulfonyl, sulfinyl or phosphonyl group and $R_D$ is a radical selected from the group consisting of:
    a) alkyl or alkenyl radicals aryl, arylalkyl, alkylaryl or alkenylaryl radicals, alicyclic, heterocyclic radicals, or polycyclic radicals;
    b) alkyl or alkenyl radicals comprising at least one functional ether, thioether, amine, imine, carboxyl, carbonyl, hydroxy, silyl, isocyanate or thioisocyanate group;

c) aryl, arylalkyl, arylalkenyl, alkylaryl or alkenylaryl radicals, in which the aromatic nuclei and/or at least one substituent of the nucleus comprises heteroatoms selected from nitrogen, oxygen, sulfur;

d) radicals comprising condensed aromatic cycles which optionally comprise at least one heteroatom selected from nitrogen, oxygen, sulfur;

e) halogenated alkyl, alkenyl, ayl arylalkyl, alkylaryl or alkenylaryl radicals in which the number of carbon atoms carrying at least one halogen is at most equal to the number of non-halogenated carbon atoms, the carbon in α position of group Y not being halogenated when Y is —$SO_2$—, said radicals optionally comprising functional ether, thioether, amine, imine, carboxyl, carbonyl, hydroxy, silyl, isocyanate or thioisocyanate groups;

f) radicals $R_C$C(R')(R") in which $R_C$ is an alkly perfluorinated radical and R' and R" are independently from one another, an hydrogen atom or a radical as defined in a), b), c) or d) above;

g) radicals $(R_B)_2$N—, in which the $R_B$, identical or different, as defined in a), b), c), d) and e) above, one of the $R_B$ may be a hydrogen atom, or the two radicals $R_B$ together fonn a bivalent radical which forms a cycle with N;

h) radicals consisting of a polymer chain;

i) radicals having one or more cationic ionophonic groups and/or one or more anionic ionophoric groups;

with the proviso that a substituent $R_D$ may be a monovalent radical, part of a multivalent radical carring a plurality of groups $R_F$S(O)x—N—Y—, or a segment of a polymer;

with the proviso that when Y is a sulfonyl and $R_D$ is a radical such as defined in a), $R_F$ is $R_A CF_2$—, $R_A CF_2 CF_2$—, $R_A CF_2 CF(CF_3)$—, $CF_3 C(R_A)F$— or a perhaloalkyl radical having 1 to 2 carbon atoms, characterized in that M is an orgmiic onium cation selected from the group consisting of $R_3 O^+$(oxonium), $NR_4^+$(ammonium), $RC(NHR_2)_2^+$(amidinium), $C(NHR_2)_3^+$(guanidinium), $C_5 R_6 N^+$(pyridinium), $C_3 R_5 N_2^+$(imidazolium), $C_2 R_4 N_3^+$(triazolium), $C_3 R_7 N_2^+$(imidazolinium), $SR_3^+$(sulfonium), $PR_4^+$(phosphonium), $IR_2^+$(iodonium), $(C_6 R_5)_3 C^+$(carbonium), the radicals R independently representing H or a radical selected from the group consisting of:

alkyl, alkenyl, oxa-alkyl oxa-alkenyl, aza-alkyl, aza-alkenyl, thia-alkyl, thia-alkenyl, sila-alkyl, sila-alkenyl, aryl, arylalkyl, alkylaryl, alkenylaryl radicals, dialkylamino radicals and dialkylazo radicals;

cyclic or heterocyclic radicals optionally comprising at least one lateral chain comprising heteroatoms such as nitrogen, oxygen, sulfur;

cyclic or heterocyclic radicals optionally comprising heteroatoms in the aromatic nuclei;

groups comprising a plurlity of aromatic or heterocyclic, condensed or non-condensed nuclei, optionally containing at least one nitrogen, oxygen, sulfur or phosphorus atom;

with the proviso that a plurality of radicals R may together fonn aliphatic or aromatic cycles optionally enclosing the center carrying the cationic charge and characterized in that M is an organic cation, incorporating a group 2,2'(azobis(2-2'-imidazolinio-2-yl) propane)$^{2+}$ or 2,2'-2+azobis(2-amidiniopropane)$^{2+}$.

38. An ionically conducting material, comprising an ionic compound in a solvent, wherein said ionic compound consists of an amide or salts thereof, comprising an anionic part associated with at least one cationic part $M^{+m}$ in sufficient number to ensure an electronic neutrality thereto, characterized in that M is a hydroxonium, a nitrosonium $NO^+$, an ammonium —$NH_4^+$, a metallic cation having a valency m, an organic onium cation having a valency m or an organometallic cation having a valency m and in that the anionic part corresponds to the formula $R_F$—$SO_x$—$N^-$—Z in which:

the group —$S(O)_x$— represents a sulfonic group —$SO_2$— or a sulfinyl group —SO—;

$R_F$ is a halogen or a perhalogenated alkyl, alkylaryl, oxa-alkyl, aza-alkyl or thia-alkyl radical, or a radical corresponding to one of the formulae $R_A CF_2$—, $R_A CF_2 CF_2$—, $R_A CF_2 CF(CF_3)$— or $CF_3 C(R_A)F$— in which $R_A$— represents a non-perhalogenated organic radical;

Z represents an electro-attractor radical having a Hammett parameter at least equal to that of a phenyl radical, selected from:

j) —CN, —$NO_2$, —SCN, —$N_3$, —$CF_3$, $R'_F CH_2$— ($R'_F$ being a perfluorinated radical) or a fluoroalkylthioxy radical, jj) radicals comprising one or more aromatic nuclei optionally containing at least one hydrogen, oxygen, sulfur or phosphorus atom, said nuclei optionally being condensed nuclei and/or said nuclei optionally carrying at least one substituent selected from halogens, —CN, —$NO_2$, —SCN, —$N_3$, —$CF_3$, $CF_3 CH_2$—, $CF_2$=CF—O—, $CF_2$=CF—S—, perfluoroalkyl groups, fluoroalkyloxy groups, fluoroalkylthioxy groups, alkyl, alkenyl, oxa-alkyl, oxa-alkenyl, aza-alkyl, aza-alkenyl, thia-alkyl, thia-alkenyl radicals, polymer radicals, radicals having at least one cationic ionophoric group and/or at least one anionic lonophoric group;

with the proviso that a substituent Z may be a monovalent radical, part of a multivalent radical carrying a plurality of groups $R_F$—$S(O)_x$—N—, or a polymer segment; or Z is a radical $R_D$—Y— in which Y is a sulfonyl, sulfinyl or phosphonyl group and $R_D$ is a radical selected from the group consisting of:

a) alkyl or alkenyl radicals, aryl, arylalkyl, alkylaryl or alkenylaryl radicals, alicyclic, heterocyclic radicals, or polycyclic radicals;

b) alkyl or alkenyl radicals comprising at least one functional ether, thioether, amine, imine, carboxyl, carbonyl, hydroxy, silyl, isocyanate or thioisocyanate group;

c) aryl, arylalkyl, arylalkenyl, alkylaryl or alkenylaryl radicals, in which the aromatic nuclei and/or at least one substituent of the nucleus comprises heteroatoms selected from nitrogen, oxygen, sulfur;

d) radicals comprising condensed aromatic cycles which optionally comprise at least one heteroatom selected from nitrogen, oxygen, sulfur;

e) halogenated alkyl, alkenyl, aryl, arylalkyl, alkylaryl or alkenylaryl radicals in which the number of carbon atoms carrying at least one halogen is at most equal to the number of non-halogenated carbon atoms, the carbon in α position of group Y not being halogenated when Y is —$SO_2$—, said radicals optionally comprising functional ether, thioether, amine, imine, carboxyl, carbonyl, hydroxy, silyl, isocyanate or thioisocyanate groups;

f) radicals $R_C$C(R')(R")—O— in which $R_C$ is an alkyl perfluorinated radical and R' and R" are independently from one another, an hydrogen atom or a radical as defined in a), b), c) or d) above;

g) radicals $(R_B)_2N—$, in which the $R_B$, identical or different, as defined in a), b), c), d) and e) above, one of the $R_B$ may be a hydrogen atom, or the two radicals $R_B$ together form a bivalent radical which forms a cycle with N;

h) radicals consisting of a polymer chain;

i) radicals having one or more cationic ionophoric groups and/or one or more anionic ionophoric groups;

with the proviso that a substituent $R_D$ may be a monovalent radical, part of a multivalent radical carrying a plurality of groups $R_FS(O)x—N—Y—$, or a segment of a polymer;

with the proviso that, when Y is a sulfonyl and $R_D$ is a radical such as defined in a), $R_F$ is $R_ACF_2—$, $R_ACF_2CF_2—$, $R_ACF_2CF(CF_3)—$, $CF_3C(R_A)F—$ or a perhaloalkyl radical having 1 to 2 carbon atoms;

further characterized in that the cation is a metallocenium, selected from the group consisting of cations derived from ferrocene, titanocene, zirconocene, indenocenium cations, arene metallocenium cations, cations of transition metals complexed with phosphine ligands optionally having a chirality and organometallic cations having one or more alkyl or aryl groups covalently fixed to an atom or a group of atoms, said cations optionally being part of a polymer chain.

39. An ionically conducting material, comprising an ionic compound in a solvent, wherein said ionic compound consists of an amide or salts thereof, comprising an anionic part associated with at least one cationic part $M^{+m}$ in sufficient number to ensure an electronic neutrality thereto, characterized in that M is a hydroxonium, a nitrosoniurn $NO^+$, an annmonium $—NH_4^+$, a metallic cation having a valency m, an organic onium cation having a valency m or an organometallic cation having a valency m and in that the anionic part corresponds to the formula $R_F—SO_X—N^-—Z$ in which:

the group $—S(O)_X—$ represents a sulfonic group $—SO_2—$ or a sulfinyl group $—SO—$;

$R_F$ is a halogen or a perhalogenated alkyl, alkylaryl, oxa-alkyl, aza-alkyl or thia-alkyl radical, or a radical corresponding to one of the formulae $R_ACF_2—$, $R_ACF_2CF_2—$, $R_ACF_2CF(CF_3)—$ or $CF_3C(R_A)F—$ in which $R_A—$ represents a non-perhalogenated organic radical;

Z represents an electro-attractor radical having a Hammett parameter at least equal to that of a phenyl radical, selected from:

j) $—CN, —NO_2, —SCN, —N_3, —CF_3, R'_FCH_2—$ ($R'_F$ being a perfluorinated radical) or a fluoroalkylthioxy radical, jj) radicals comprising one or more aromatic nuclei optionally containing at least one hydrogen, oxygen, sulfur or phosphorus atom, said nuclei optionally being condensed nuclei and/or said nuclei optionally carrying at least one substituent selected from halogens, $—CN, —NO_2, —SCN, —N_3, —CF_3$, $CF_3CH_2—, CF_2=CF—O—, CF_2=CF—S—$, perfluoroalkyl groups, fluoroalkyloxy groups, fluoroalkylthioxy groups, alkyl, alkenyl, oxa-alkyl, oxa-alkenyl, aza-alkyl, aza-alkenyl, thia-alkyl, thia-alkenyl radicals, polymer radicals, radicals having at least one cationic ionophoric group and/or at least one anionic ionophoric group;

with the proviso that a substituent Z may be a monovalent radical, part of a multivalent radical carrying a plurality of groups $R_F—S(O)_X—N—$, or a polymer segment; or Z is a radical $R_D—Y—$ in which Y is a sulfonyl, sulfinyl or phosphonyl group and $R_D$ is a radical selected from the group consisting of:

a) alkyl or alkenyl radicals, aryl, arylalkyl, alkylaryl or alkenylaryl radicals, alicyclic, heterocyclic radicals, or polycyclic radicals;

b) alkyl or alkenyl radicals comprising at least one functional ether, thioether, amine, imine, carboxyl, carbonyl, hydroxy, silyl, isocyanate or thioisocyanate group;

c) aryl, arylalkyl, arylalkenyl, alkylaryl or alkenylaryl radicals, in which the aromatic nuclei and/or at least one substituent of the nucleus comprises heteroatoms selected from nitrogen, oxygen, sulfur;

d) radicals comprising condensed aromatic cycles which optionally comprise at least one heteroatom selected from nitrogen, oxygen, sulfur;

e) halogenated alkyl, alkenyl, aryl, arylalkyl, alkylaryl or alkenylaryl radicals in which the number of carbon atoms carrying at least one halogen is at most equal to the number of non-halogenated carbon atoms, the carbon in α position of group Y not being halogenated when Y is $—SO_2—$, said radicals optionally comprising functional ether, thioether, amine, imine, carboxyl, carbonyl, hydroxy, silyl, isocyanate or thioisocyanate groups;

f) radicals $R_CC(R')(R'')—O—$ in which $R_C$ is an alkyl perfluorinated radical and R' and R" are independently from one another, an hydrogen atom or a radical as defined in a), b), c) or d) above;

g) radicals $(R_B)_2N—$, in which the $R_B$, identical or different, as defined in a), b), c), d) and e) above, one of the $R_B$ may be a hydrogen atom, or the two radicals $R_B$ together form a bivalent radical which forms a cycle with N;

h) radicals consisting of a polymer chain;

i) radicals having one or more cationic ionophoric groups and/or one or more anionic ionophoric groups;

with the proviso that a substituent $R_D$ may be a monovalent radical, part of a multivalent radical carrying a plurality of groups $R_FS(O)x—N—Y—$, or a segment of a polymer;

with the proviso that, when Y is a sulfonyl and $R_D$ is a radical such as defined in a), $R_F$ is $R_ACF_2—$, $R_ACF_2CF_2—$, $R_ACF_2CF(CF_3)—$, $CF_3C(R_A)F—$ or a perhaloalkyl radical having 1 to 2 carbon atoms;

further characterized in that Z represents a recurring unit of a polymer chain.

40. An ionically conducting material, comprising an ionic compound in a solvent, wherein said ionic compound consists of an amide or salts thereof, comprising an anionic part associated with at least one cationic part $M^{+m}$ in sufficient number to ensure an electronic neutrality thereto, characterized in that M is a hydroxonium, a nitrosonium $NO^+$, an ammonium $—NH_4^+$, a metallic cation having a valency m, an organic onium cation having a valency m or an organometallic cation having a valency m and in that the anionic part corresponds to the formula $R_F—SO_X—N^-—Z$ in which:

the group $—S(O)_X—$ represents a sulfonic group $—SO_2—$ or a sulfinyl group $—SO—$;

$R_F$ is a halogen or a perhalogenated alkyl, alkylaryl, oxa-alkyl, aza-alkyl or thia-alkyl radical, or a radical corresponding to one of the formulae $R_ACF_2$—, $R_ACF_2CF_2$—, $R_ACF_2CF(CF_3)$— or $CF_3C(R_A)F$— in which $R_A$— represents a non-perhalogenated organic radical;

Z represents an electro-attractor radical having a Hammett parameter at least equal to that of a phenyl radical, selected from:

j) —CN, —NO$_2$, —SCN, —N$_3$, —CF$_3$, R'$_F$CH$_2$— (R'$_F$ being a perfluorinated radical) or a fluoroalkylthioxy radical, jj) radicals comprising one or more aromatic nuclei optionally containing at least one hydrogen, oxygen, sulfur or phosphorus atom, said nuclei optionally being condensed nuclei and/or said nuclei optionally carrying at least one substituent selected from halogens, —CN, —NO$_2$, —SCN, —N$_3$, —CF$_3$, CF$_3$CH$_2$—, CF$_2$=CF—O—, CF$_2$=CF—S—, perfluoroalkyl groups, fluoroalkyloxy groups, fluoroalkylthioxy groups, alkyl, alkenyl, oxa-alkyl, oxa-alkenyl, aza-alkyl, aza-alkenyl, thia-alkyl, thia-alkenyl radicals, polymer radicals, radicals having at least one cationic ionophoric group and/or at least one anionic ionophonrc group;

with the proviso that a substituent Z may be a monovalent radical, part of a multivalent radical carrying a plurality of groups $R_F$—S(O)$_X$—N—, or a polymer segment; or Z is a radical $R_D$—Y— in which Y is a sulfonyl, sulfinyl or phosphonyl group and $R_D$ is a radical selected from the group consisting of:

a) alkyl or alkenyl radicals, aryl, arylalkyl, alkylaryl or alkenylaryl radicals, alicyclic, heterocyclic radicals, or polycyclic radicals;

b) alkyl or alkenyl radicals comprising at least one functional ether, thioether, amine, imine, carboxyl, carbonyl, hydroxy, silyl, isocyanate or thioisocyanate group;

c) aryl, arylalkyl, arylalkenyl, alkylaryl or alkenylaryl radicals, in which the aromatic nuclei and/or at least one substituent of the nucleus comprises heteroatoms selected from nitrogen, oxygen, sulfur;

d) radicals comprising condensed aromatic cycles which optionally comprise at least one heteroatom selected from nitrogen, oxygen, sulfur;

e) halogenated alkyl, alkenyl, aryl, arylalkyl, alkylaryl or alkenylaryl radicals in which the number of carbon atoms carrying at least one halogen is at most equal to the number of non-halogenated carbon atoms, the carbon in α position of group Y not being halogenated when Y is —SO$_2$—, said radicals optionally comprising functional ether, thioether, amine, imine, carboxyl, carbonyl, hydroxy, silyl, isocyanate or thioisocyanate groups;

f) radicals $R_CC(R')(R'')$—O— in which $R_C$ is an alkyl perfluorinated radical and R' and R'' are independently from one another, an hydrogen atom or a radical as defined in a), b), c) or d) above;

g) radicals $(R_B)_2N$—, in which the $R_B$, identical or different, as defined in a), b), c), d) and e) above, one of the $R_B$ may be a hydrogen atom, or the two radicals $R_B$ together form a bivalent radical which forms a cycle with N;

h) radicals consisting of a polymer chain;

i) radicals having one or more cationic ionophoric groups and/or one or more anionic ionophoric groups;

with the proviso that a substituent $R_D$ may be a monovalent radical, part of a multivalent radical carrying a plurality of groups $R_FS(O)x$—N—Y—, or a segment of a polymer;

with the proviso that, when Y is a sulfonyl and $R_D$ is a radical such as defined in a), $R_F$ is $R_ACF_2$—, $R_ACF_2CF_2$—, $R_ACF_2CF(CF_3)$—, $CF_3C(R_A)F$— or a perhaloalkyl radical having 1 to 2 carbon atoms;

further characterized in that the substituent Z is selected from the group consisting of —OC$_n$F$_{2n+1}$, —OC$_2$F$_4$H, —SC$_n$F$_{2n+1}$ and —SC$_2$F$_4$H, —OCF=CF$_2$, —SCF=CF$_2$ and C$_n$F$_{2n}$+1CH$_{2-n}$ being a whole number from 1 to 8.

41. Ionically conductive material comprising an ionic compound in a solvent, wherein said ionic compound consists of an amide or salts thereof, comprising an anionic part associated with at least one cationic part M$^{+m}$ in sufficient number to ensure an electrotnic neutrality thereto, characterized in that M is a hydroxonium, a nitrosonium NO$^+$, an ammonium —NH$_4^+$, a metallic cation having a valency m, an organic onium cation having a valency m or an organo-motallic cation having a valency m and in that the anionic part corresponds to the formula $R_F$—SO$_X$—N$^+$—Z in which:

the group —S(O)$_X$— represents a sulfonic group —SO$_2$— or a sulfinyl group —SO—;

$R_F$ is a halogen or a perhalogenated alkyl, alkylaryl oxa-alkyl, aza-akyl or thia-alkyl radical, or a radical corresponding to one of the formulae $R_ACF_2$—, $R_ACF_2CF_2$—, $R_ACF_2CF(CF_3)$— or $CF_3C(R_A)F$— in which $R_A$— represents a non-perhalogenated organic radical;

Z represents an electro-attractor radical having a Hammett parameter at least equal to that of a phenyl radical, selected from:

j) —CN, —NO$_2$, —SCN, —N$_3$, —CF$_3$, R'$_F$CH$_2$— (R$_F$ being a perfluorinated radical) or a fluroalkylthioxy radical, jj) radicals comprising one or more aromatic nuclei optionally containing at least one hydrogen, oxygen, sulfur or phosphorus atom, said nuclei optionally being condensed nuclei and/or said nuclei optionally carrying at least one substituent selected from halogens, —CN, —NO$_2$, —SCN, —N$_3$, —CF$_3$, CF$_3$CH$_2$—, CF$_2$=CF—O—, CF$_2$=CF—S—, perfluoroalkyl groups, fluoroalkyloxy groups, fluoroalkylthioxy groups, alkyl, alkenyl, oxa-alkyl, oxa-alkenyl, aza-alkyl, aza-alkenyl, thia-alkyl, thia-alkenyl radicals, polymer radicals, radicals having at least one cationic ionophoric group and/or at least one anionic ionophoric group;

with the proviso that a substituent Z may be a monovalent radical, part of a multivalent radical carrying a plurality of groups $R_FS(O)_X$—N—, or a polymer segment; or Z is a radical $R_D$—Y— in which Y is a sulfonyl, sulfinyl or phosphonyl group and $R_D$ is a radical selected from the group consisting of:

a) alkyl or alkenyl radicals, aryl, arylalkyl, alkylaryl or alkenylaryl radicals, alicyclic, heterocyclic radicals, or polycyclic radicals;

b) alkyl or alkenyl radicals comprising at least one functional ether, thioether, amine, imine, carboxyl, carbonyl, hydroxy, silyl, isocyanate or thioisocyanate group;

c) aryl, arylalkyl, arylalkenyl, alkylaryl or alkenylaryl radicals, in which the aromatic nuclei and/or at least one substituent of the nucleus comprises heteroatoms selected from nitrogen, oxygen, sulfur,
d) radicals comprising condensed aromatic cycles which optionally comprise at least one heteroatom selected from nitrmgon, oxygen, sulfur;
e) halogenated alkyl, alkenyl, aryl, arylalkyl, alkylaryl or alkenylaryl radicals in which the number of carbon atoms carrying at least one halogen is at most equal to the number of non-halogenated carbon atoms, the carbon in α position of group Y not being halogenated when Y is —$SO_2$—, said radicals optionally comprising functional other, thioether, amine, imine, carboxyl, carbonyl, hydroxy, silyl, isocyanate or thioisocyanate groups;
f) radicals $R_C$C(R')(R")— in which $R_C$ is an alkyl perfluorinated radical and R' and R" are independently from one another, an hydrogen atom or a radical as defined in a), b), c) or d) above;
g) radicals $(R_B)_2$N—, in which the $R_B$, identical or different, as defined in a), b), c), d) and e) above, one of the $R_B$ may be a hydrogen atom, or the two radicals $R_B$ together form a bivalent radical which forms a cycle with N;
h) radicals consisting of a polymer chain;
i) radicals having one or more cationic ionophoric groups and/or one or more anionic ionophoric groups;
with the proviso that a substituent $R_D$ may be a monovalent radical, part of a multivalent radical carrying a plurality of groups $R_F$S(O)x—N—Y—, or a segment of a polymer;
with the proviso that when Y is a sulfonyl and $R_D$ is a radical such as defined in a), $R_F$ is $R_A$$CF_2$—, $R_A$$CF_2$$CF_2$—, $R_A$$CF_2$CF($CF_3$)—, $CF_3$C($R_A$)F— or a perhaloalkyl radical having 1 to 2 carbon atoms;
characterized in that the solvent is a crosslinked or non-cross-linked solvating polymer, which may carry grafted ionic groups.

42. Ionically conductive material according to claim 41, characterized in that the solvating polymer is selected from polyethers of linear structure, comb or blocks, which may form a network, based on poly (ethylene oxide), copolymers containing ethylene oxide, propylene oxide or allylglycidylether units, polyphosphazenes, cross-linked networks based on polyethylene glycol cross-linked with isocyanates, polymer networks obtained by polycondensation and carrying groups which enable the incorporation of cross-linkable groups and block copolymers in which some blocks carry functions which have redox properties.

43. Ionically conductive material, comprising an ionic compound in a solvent, wherein said ionic compound consists of an amide or salts thereof, comprising an anionic part associated with at least one cationic part $M^{+m}$ in sufficient number to ensure an electronic neutrality thereto, characterized in that M is a hydroxonium, a nitrosonium $NO^+$, an ammonium —$NH_4^+$, a metallic cation having a valency m, an organic onium cation having a valency m or an organometallic cation having a valency m and in that the anionic part corresponds to the formula $R_F$—$SO_X$—$N^-$—Z in which:
the group —$S(O)_X$— represents a sulfonic group —$SO_2$— or a sulfinyl group —SO—;
$R_F$ is a halogen or a perhalogenated alkyl, alkylaryl, oxa-alkyl, aza-alkyl or thia-alkyl radical, or a radical corresponding to one of the formulae $R_A$$CF_2$—, $R_A$$CF_2$$CF_2$—, $R_A$$CF_2$CF($CF_3$)— or $CF_3$C($R_A$)F— in which $R_A$— represents a non-perhalogenated organic radical;

Z represents an electro-attractor radical having a Hammett parameter at least equal to that of a phenyl radical, selected from:
j) —CN, —$NO_2$, —SCN, —$N_3$, —$CF_3$, $R'_F$$CH_2$— ($R'_F$ being a perfluorinated radical) or a fluoroalkylthioxy radical,
jj) radicals comprising one or more aromatic nuclei optionally containing at least one hydrogen, oxygen, sulfur or phosphorus atom, said nuclei optionally being condensed nuclei and/or said nuclei optionally carrying at least one substituent selected from halogens, —CN, —$NO_2$, —SCN, —$N_3$, —$CF_3$, $CF_3$$CH_2$—, $CF_2$=CF—O—, $CF_2$=CF—S—, perfluoroalkyl groups, fluoroalkyloxy groups, fluoroalkylthioxy groups, alkyl, alkenyl, oxa-alkyl, oxa-alkenyl, aza-alkyl, aza-alkenyl, thia-alkyl, thia-alkenyl radicals, polymer radicals, radicals having at least one cationic ionophoric group and/or at least one anionic ionophoric group;
with the proviso that a substituent Z may be a monovalent radical, part of a multivalent radical carrying a plurality of groups $R_F$—$S(O)_X$—N—, or a polymer segment; or
Z is a radical $R_D$—Y— in which Y is a sulfonyl, sulfinyl or phosphonyl group and $R_D$ is a radical selected from the group consisting of:
a) alkyl or alkenyl radicals, aryl, arylalkyl, alkylaryl or alkenylaryl radicals, alicyclic, heterocyclic radicals, or polycyclic radicals;
b) alkyl or alkenyl radicals comprising at least one functional ether, thioether amine, imine, carboxyl, carbonyl, hydroxy, silyl, isocyanate or thioisocyanate group;
c) aryl, arylalkyl, arylalkenyl, alkylaryl or alkenylaryl radicals, in which the aromatic nuclei and/or at least one substituent of the nucleus comprises heteroatoms selected from nitrogen, oxygen, sulfur;
d) radicals comprising condensed aromatic cycles which optionally comprise at least one heteroatom selected from nitrogen, oxygen, sulfur;
e) halogenated alkyl, alkenyl, aryl, arylalkyl, alkylaryl or alkenylaryl radicals in which the number of carbon atoms carrying at least one halogen is at most equal to the number of non-halogenated carbon atoms, the carbon in α position of group Y not being halogenated when Y is —$SO_2$—, said radicals optionally comprising functional ether, thioether, amine, imine, carboxyl, carbonyl, hydroxy, silyl, isocyanate or thioisocyanate groups;
f) radicals $R_C$C(R')(R")—O— in which $R_C$ is an alkyl perfluorinated radical and R' and R" are independently from one another, an hydrogen atom or a radical as defined in a), b), c) or d) above;
g) radicals $(R_B)_2$N—, in which the $R_B$, identical or different, as defined in a), b), c), d) and e) above, one of the $R_B$ may be a hydrogen atom, or the two radicals $R_B$ together form a bivalent radical which forms a cycle with N;
h) radicals consisting of a polymer chain;
i) radicals having one or more cationic ionophoric groups and/or one or more anionic ionophoric groups;
with the proviso that a substituent $R_D$ may be a monovalent radical, part of a multivalent radical carrying a plurality of groups $R_F$S(O)x—N—Y—, or a segment of a polymer;
with the proviso that, when Y is a sulfonyl and $R_D$ is a radical such as defined in a), $R_F$ is $R_A$$CF_2$—, $R_ACF_2CF_2$—, $R_ACF_2CF(CF_3)$—, $CF_3C(R_A)F$— or a perhaloalkyl radical having 1 to 2 carbon atoms;

further characterized in that the solvent essentially consists of a liquid aprotic solvent and a polar polymer solvent comprising units containing at least one heteroatom selected from sulfur, oxygen, nitrogen and fluorine.

44. Ionically conductive material according to claim 43, characterized in that the polar polymer mainly contains units derived from acrylonitrile, vinylidene fluoride, N-vinylpyrrolidone or methyl methacrylate.

45. Ionically conductive material, comprising an ionic compound in a solvent, wherein said ionic compound consists of an amide or salts thereof, comprising an anionic part associated with at least one cationic part $M^{+m}$ in sufficient number to ensure an electronic neutrality thereto, characterized in that M is a hydroxonium, a nitrosonium $NO^+$, an ammonium —$NH_4^+$, a metallic cation having a valency m, an organic onium cation having a valency m or an organometallic cation having a valency m and in that the anionic part corresponds to the formula $R_F$—$SO_X$—$N^-$—Z in which:

the group —$S(O)_X$— represents a sulfonic group —$SO_2$— or a sulfinyl group —SO—;

$R_F$ is a halogen or a perhalogenated alkyl, alkylaryl, oxa-alkyl, aza-alkyl or thia-alkyl radical, or a radical corresponding to one of the formulae $R_ACF_2$—, $R_ACF_2CF_2$—, $R_ACF_2CF(CF_3)$— or $CF_3C(R_A)F$— in which $R_A$— represents a non-perhalogenated organic radical;

Z represents an electro-attractor radical having a Hammett parameter at least equal to that of a phenyl radical, selected from:

j) —CN, —$NO_2$, —SCN, —$N_3$, —$CF_3$, $R'_FCH_2$— ($R'_F$ being a perfluorinated radical) or a fluoroalkylthioxy radical, jj) radicals comprising one or more aromatic nuclei optionally containing at least one hydrogen, oxygen, sulfur or phosphorus atom, said nuclei optionally being condensed nuclei and/or said nuclei optionally carrying at least one substituent selected from halogens, —CN, —$NO_2$, —SCN, —$N_3$, —$CF_3$, $CF_3CH_2$—, $CF_2$=CF—O—, $CF_2$=CF—S—, perfluoroalkyl groups, fluoroalkyloxy groups, fluoroalkylthioxy groups, alkyl, alkenyl, oxa-alkyl, oxa-alkenyl, aza-alkyl, aza-alkenyl, thia-alkyl, thia-alkenyl radicals, polymer radicals, radicals having at least one cationic ionophoric group and/or at least one anionic ionophoric group;

with the proviso that a substituent Z may be a monovalent radical, part of a multivalent radical carrying a plurality of groups $R_F$—$S(O)_X$—N—, or a polymer segment; or Z is a radical $R_D$—Y— in which Y is a sulfonyl, sulfinyl or phosphonyl group and $R_D$ is a radical selected from the group consisting of:

a) alkyl or alkenyl radicals, aryl, arylalkyl, alkylaryl or alkenylaryl radicals, alicyclic, heterocyclic radicals, or polycyclic radicals;

b) alkyl or alkenyl radicals comprising at least one functional ether, thioether, amine, imine, carboxyl, carbonyl, hydroxy, silyl, isocyanate or thioisocyanate group;

c) aryl, arylalkyl, arylalkenyl, alkylaryl or alkenylaryl radicals, in which the aromatic nuclei and/or at least one substituent of the nucleus comprises heteroatoms selected from nitrogen, oxygen, sulfur;

d) radicals comprising condensed aromatic cycles which optionally comprise at least one heteroatom selected from nitrogen, oxygen, sulfur;

e) halogenated alkyl, alkenyl, aryl, arylalkyl, alkylaryl or alkenylaryl radicals in which the number of carbon atoms carrying at least one halogen is at most equal to the number of non-halogenated carbon atoms, the carbon in α position of group Y not being halogenated when Y is —$SO_2$—, said radicals optionally comprising functional ether, thioether, amine, imine, carboxyl, carbonyl, hydroxy, silyl, isocyanate or thioisocyanate groups;

f) radicals $R_CC(R')(R'')$—O— in which $R_C$ is an alkyl perfluorinated radical and R' and R" are independently from one another, an hydrogen atom or a radical as defined in a), b), c) or d) above;

g) radicals $(R_B)_2N$—, in which the $R_B$, identical or different, as defined in a), b), c), d) and e) above, one of the $R_B$ may be a hydrogen atom, or the two radicals $R_B$ together form a bivalent radical which forms a cycle with N;

h) radicals consisting of a polymer chain;

i) radicals having one or more cationic ionophoric groups and/or one or more anionic ionophoric groups;

with the proviso that a substituent $R_D$ may be a monovalent radical, part of a multivalent radical carrying a plurality of groups $R_FS(O)x$—N—Y—, or a segment of a polymer;

with the proviso that, when Y is a sulfonyl and $R_D$ is a radical such as defined in a), $R_F$ is $R_ACF_2$—, $R_ACF_2CF_2$—, $R_ACF_2CF(CF_3)$—, $CF_3C(R_A)F$— or a perhaloalkyl radical having 1 to 2 carbon atoms;

further characterized in that it additionally contains at least one second salt.

46. Ionically conductive material, comprising an ionic compound in a solvent, wherein said ionic compound consists of an amide or salts thereof, comprising an anionic part associated with at least one cationic part $M^{+m}$ in sufficient number to ensure an electronic neutrality thereto, characterized in that M is a hydroxonium, a nitrosonium $NO^+$, an ammonium —$NH_4^+$, a metallic cation having a valency m, an organic onium cation having a valency m or an organometallic cation having a valency m and in that the anionic part corresponds to the formula $R_F$—$SO_X$—$N^-$—Z in which:

the group —$S(O)_X$— represents a sulfonic group —$SO_2$— or a sulfinyl group —SO—;

$R_F$ is a halogen or a perhalogenated alkyl, alkylaryl, oxa-alkyl, aza-alkyl or thia-alkyl radical, or a radical corresponding to one of the formulae $R_ACF_2$—, $R_ACF_2CF_2$—, $R_ACF_2CF(CF_3)$— or $CF_3C(R_A)F$— in which $R_A$— represents a non-perhalogenated organic radical;

Z represents an electro-attractor radical having a Hammett parameter at least equal to that of a phenyl radical, selected from:

j) —CN, —$NO_2$, —SCN, —$N_3$, —$CF_3$, $R'_FCH_2$— ($R'_F$ being a perfluorinated radical) or a fluoroalkylthioxy radical, jj) radicals comprising one or more aromatic nuclei optionally containing at least one hydrogen, oxygen, sulfur or phosphorus atom, said nuclei optionally being condensed nuclei and/or said nuclei optionally carrying at least one substituent selected from halogens, —CN, —$NO_2$, —SCN, —$N_3$, —$CF_3$, $CF_3CH_2-$, $CF_2=CF-O-$, $CF_2=CF-S-$, perfluoroalkyl groups, fluoroalkyloxy groups, fluoroalkylthioxy groups, alkyl, alkenyl, oxa-alkyl, oxa-alkenyl, aza-alkyl, aza-alkenyl, thia-alkyl, thia-alkenyl radicals, polymer radicals, radicals having at least one cationic ionophoric group and/or at least one anionic ionophoric group;

with the proviso that a substituent Z may be a monovalent radical, part of a multivalent radical carrying a plurality of groups $R_F-S(O)_X-N-$, or a polymer segment; or Z is a radical $R_D-Y-$ in which Y is a sulfonyl, sulfinyl or phosphonyl group and $R_D$ is a radical selected from the group consisting of:
  a) alkyl or alkenyl radicals, aryl, arylalkyl, alkylaryl or alkenylaryl radicals, alicyclic, heterocyclic radicals, or polycyclic radicals;
  b) alkyl or alkenyl radicals comprising at least one functional ether, thioether, amine, imine, carboxyl, carbonyl, hydroxy, silyl, isocyanate or thioisocyanate group;
  c) aryl, arylalkyl, arylalkenyl, alkylaryl or alkenylaryl radicals, in which the aromatic nuclei and/or at least one substituent of the nucleus comprises heteroatoms selected from nitrogen, oxygen, sulfur;
  d) radicals comprising condensed aromatic cycles which optionally comprise at least one heteroatom selected from nitrogen, oxygen, sulfur;
  e) halogenated alkyl, alkenyl, aryl, arylalkyl, alkylaryl or alkenylaryl radicals in which the number of carbon atoms carrying at least one halogen is at most equal to the number of non-halogenated carbon atoms, the carbon in α position of group Y not being halogenated when Y is $-SO_2-$, said radicals optionally comprising functional ether, thioether, amine, imine, carboxyl, carbonyl, hydroxy, silyl, isocyanate or thioisocyanate groups;
  f) radicals $R_CC(R')(R'')-O-$ in which $R_C$ is an alkyl perfluorinated radical and R' and R'' are independently from one another, an hydrogen atom or a radical as defined in a), b), c) or d) above;
  g) radicals $(R_B)_2N-$, in which the $R_B$, identical or different, as defined in a), b), c), d) and e) above, one of the $R_B$ may be a hydrogen atom, or the two radicals $R_B$ together form a bivalent radical which forms a cycle with N;
  h) radicals consisting of a polymer chain;
  i) radicals having one or more cationic ionophoric groups and/or one or more anionic ionophoric groups;

with the proviso that a substituent $R_D$ may be a monovalent radical, part of a multivalent radical carrying a plurality of groups $R_FS(O)_X-N-Y-$, or a segment of a polymer;

with the proviso that, when Y is a sulfonyl and $R_D$ is a radical such as defined in a), $R_F$ is $R_ACF_2-$, $R_ACF_2CF_2-$, $R_ACF_2CF(CF_3)-$, $CF_3C(R_A)F-$ or a perhaloalkyl radical having 1 to 2 carbon atoms;

further characterized in that it additionally contains a mineral or organic charge in the form of powder or fibres.

* * * * *

UNITED STATES PATENT AND TRADEMARK OFFICE
CERTIFICATE OF CORRECTION

PATENT NO. : 6,319,428 B1
DATED : November 20, 2001
INVENTOR(S) : Michot et al.

It is certified that error appears in the above-identified patent and that said Letters Patent is hereby corrected as shown below:

Column 88,
Line 16, insert a comma between the term "arylalkyl" and the term "alkylaryl" so it reads -- arylalkyl, alkylaryl --,
Line 23, insert a comma between the term "aryl" and the term "arylkyl" so it reads -- aryl, arylkyl --,
Line 31, the term "nunmber" should read -- number --
Line 54, the formula "$R_FS(O)X-N-Y-$" should read -- $R_FS(O)_x-N-Y-$ --,
Line 63, the term "conducdng" should read -- conducting --.

Column 89,
Line 21, the term "nucli" should read -- nuclei --;
Line 29, the term "alkeniyl" should read -- alkenyl --,
Line 55, the term "alkylaryt" should read -- alkylaryl --;
Line 62, the term "caibonyl" should read -- carbonyl --,
Line 65, the term "perfluorinatcd" should read -- perfluorinated --,
Line 66, the term "mother" should read -- another --.

Column 90,
Line 1, the formula "$(R^B)_2N-$" should read -- $(R_B)_2N-$ --;
Line 2, "a), b), c), d) and c) above" should read -- a), b), c), d) and e) above --;
Line 4, the term "fonn" should read -- form --.

Column 91,
Lines 10-11, the term "perufloroaklyl" should read -- perfluoroalkyl --;
Line 28, the term "iminee" should read -- imine --;
Line 40, the term "halogon" should read -- halogen --;
Line 48, the term "indpdently" should read -- independently --;
Line 50, the term "dcfined" should read -- defined --;
Line 54, the term "togother" should read -- together --;
Line 62, the formula "$R_FS(O)X-N-Y-$" should read -- $R_FS(O)_x-N-Y-$ --;
Line 65, the formula "$R_AC_2-$" should read -- $R_ACF_2-$ --.

UNITED STATES PATENT AND TRADEMARK OFFICE
CERTIFICATE OF CORRECTION

PATENT NO.    : 6,319,428 B1
DATED         : November 20, 2001
INVENTOR(S)   : Michot et al.

It is certified that error appears in the above-identified patent and that said Letters Patent is hereby corrected as shown below:

Column 92,
Line 8, the term "rdicals" should read -- radicals --;
Lines 34 and 35, the term "characterzed" should read -- characterized --;
Line 36, the term "ammionium" should read -- ammonium --;
Line 57, the term "phosphoms" should read -- phosphorus --.

Column 93,
Line 20, the term "fronn" should read -- from --;
Line 23, the term "carryng" should read -- carrying --;
Line 27, the term "other" should read -- ether --;
Line 62, the term "alklenyl" should read -- alkenyl --.

Column 94,
Line 8, the term "forn" should read -- from --;
Lines 11 and 12, the term "triarylsulifonium" should read -- triarylsulfonium --;
Line 59, the term "selectcd" should read -- selected --.

Column 95,
Line 8, the term "ayl" should read -- aryl --;
Line 17, the term "alkly" should read -- alkyl --;
Line 23, the term "fonn" should read -- form --;
Line 26, the term "ionophonic" should read -- ionophoric --;
Line 37, the term "orgmiic" should read -- organic --;
Line 56, the term "plurlity" should read -- plurality --;
Line 61, the term "fonn" should read -- form --.

Column 97,
Line 34, the term "nitrosoniurn" should read -- nitrosonium --;
Line 35, the term "annmonium" should read -- ammonium --.

UNITED STATES PATENT AND TRADEMARK OFFICE
CERTIFICATE OF CORRECTION

PATENT NO. : 6,319,428 B1
DATED : November 20, 2001
INVENTOR(S) : Michot et al.

It is certified that error appears in the above-identified patent and that said Letters Patent is hereby corrected as shown below:

<u>Column 99,</u>
Line 24, the term "ionophore" should read -- ionophoric --.

<u>Column 100,</u>
Line 12, the term "$C_nF_{2n}+ 1CH_{2-n}$" should read -- $C_nF_{2n+1}$, n --;
Line 17, the term "electrotnic" should read -- electronic --;
Line 21, the term "motallic" should read -- metallic --;
Line 27, the term "akyl" should read --alkyl --.

<u>Column 101,</u>
Line 5, the term "nitrmegon" should read -- nitrogen --.

Signed and Sealed this

Thirtieth Day of July, 2002

Attest:

JAMES E. ROGAN
*Attesting Officer*     *Director of the United States Patent and Trademark Office*

UNITED STATES PATENT AND TRADEMARK OFFICE
CERTIFICATE OF CORRECTION

| | | |
|---|---|---|
| PATENT NO. | : 6,319,428 B1 | Page 1 of 2 |
| APPLICATION NO. | : 09/125797 | |
| DATED | : November 20, 2001 | |
| INVENTOR(S) | : Christophe Michot et al. | |

It is certified that error appears in the above-identified patent and that said Letters Patent is hereby corrected as shown below:

Column 2, line 51, the term "sulfmyl" should read --sulfimyl--; line 16, the term "arylakyl" should read --arylalkyl--.
Column 77, line 17, the term "filn" should read --film--; line 49, the term "amionium" should read --ammonium--.
Column 79, lines 17, 23, 27, 34, 41, and 44, "An ionically conducting material" should read --The generator--.
Column 79, line 25, the term "carhon" should read --carbon--; line 28, the term "sclocted" should read --selected--; line 31, insert a --,-- between the term "aryl" and the term "arylalkyl" so it reads --aryl, arylalkyl--; line 37, the term "heterostom" should read --heteroatom--; line 39, the term "aminc" should read --amino--; line 46, the term "others" should read --ethers--.
Column 80, line 18, the term "fylthioxy" should read --kylthioxy--; line 49, the term "halogenatod" should read --halogenated--; line 63, the term "catonic" should read --cationic--.
Column 81, lines 7, 32, and 38, "An ionically conducting material" should read --The supercapacitor--.
Column 81, line 14, the term "II" should read --H-- and the term "selecled" should read --selected--; line 32, the term "accotding" should read --according--; line 42, the term "hydrocatons" should read --hydrocarbons--.
Column 83, line 3, the term "acording" should read --according--.
Column 83, lines 3, 30, 36, 40, 47, and 54, "An ionically conducting material" should read --Use of a material comprising an ionic compound in a solvent--.
Column 85, lines 12, 39, 45, 49, 56, 63, and 66, "An ionically conducting material" should read --The electrochrome device--.
Column 85, line 60, the term "carryig" should read --carrying--.
Column 86, line 9, the term "neutrity" should ready --neutrality--; line 13, the term "organo-metallie" should read --organo-metallic--; line 18, insert a --,-- between the term "alkyl" and the term "alkylaryl" so it reads --alkyl, alkylaryl--.
Column 87, line 4, the term "others" should read --ether,--; line 22, the formula "RFS(O)X—N—Y—" should read --RFS(O)x—N—Y— --; line 31, "An ionically conducting material" should read --Electronically conductive material--; line 32, the term "charactcdzed" should Signed and Sealed this
Third Day of July, 2012

David J. Kappos
*Director of the United States Patent and Trademark Office* read --characterized--; line 42, the term "NO30" should read --NO+--; line 57, the term "elcctro-attractor" should read --electro-attractor--.